(12) United States Patent
Yuan et al.

(10) Patent No.: US 7,906,528 B2
(45) Date of Patent: Mar. 15, 2011

(54) PYRROLO-PYRIDINE, PYRROLO-PYRIMIDINE AND RELATED HETEROCYCLIC COMPOUNDS

(75) Inventors: Jun Yuan, Guilford, CT (US); Peter Hrnciar, Hamden, CT (US); Qin Guo, Waterford, CT (US); George D. Maynard, Clinton, CT (US)

(73) Assignee: Novartis International Pharmaceutical Ltd., Hamilton (BM)

( * ) Notice: Subject to any disclaimer, the term of this patent is extended or adjusted under 35 U.S.C. 154(b) by 526 days.

(21) Appl. No.: 11/664,565

(22) PCT Filed: Oct. 5, 2005

(86) PCT No.: PCT/US2005/036126
§ 371 (c)(1),
(2), (4) Date: Feb. 8, 2008

(87) PCT Pub. No.: WO2006/042102
PCT Pub. Date: Apr. 20, 2006

(65) Prior Publication Data
US 2008/0267887 A1    Oct. 30, 2008

Related U.S. Application Data

(60) Provisional application No. 60/616,311, filed on Oct. 5, 2004.

(51) Int. Cl.
C07D 221/02     (2006.01)
C07D 471/02     (2006.01)
C07D 491/02     (2006.01)
C07D 498/02     (2006.01)
A01N 43/42      (2006.01)
A61K 31/44      (2006.01)

(52) U.S. Cl. ......... 514/299; 514/300; 546/112; 546/113
(58) Field of Classification Search ............... 546/112, 546/113, 183; 514/299, 300, 312
See application file for complete search history.

(56) References Cited

U.S. PATENT DOCUMENTS

| | | | |
|---|---|---|---|
| 6,849,641 B1 * | 2/2005 | Tang et al. | 514/300 |
| 2005/0176706 A1 * | 8/2005 | Bekkali et al. | 514/234.5 |
| 2007/0179138 A1 * | 8/2007 | Cai et al. | 514/234.2 |
| 2007/0197478 A1 * | 8/2007 | Jones et al. | 514/81 |
| 2007/0219230 A1 * | 9/2007 | Kim et al. | 514/300 |
| 2009/0099172 A1 * | 4/2009 | Cai et al. | 514/234.2 |
| 2009/0232844 A1 * | 9/2009 | Sutton et al. | 424/209.1 |
| 2009/0325970 A1 * | 12/2009 | Yuan | 514/249 |

FOREIGN PATENT DOCUMENTS
WO    03066586    *    8/2003

OTHER PUBLICATIONS

Database CAPLUS on STN, Chemical Abstracts (Columbus, Ohio, USA), CA 72:21629, Yakhontov, LN et al, 'Azaindole derivatives. XXVII. Closing of a prrroline ring based on 3-(beta-chloroethyl)-4,6-dichloropyridine. Synthesis of 2,3-dihydro-5-azaindoles', abs of Khimiya Geterotsiklicheskikh Soedinenii (1969), (3), pp. 550-554.
Database CAPLUS on STN, Chemical Abstracts (columbus, Ohio, USA), CA 112:198167, El-Dean, et al., 'Synthesis of some new fused thieno- and furopyridines', abs of Phosphorus, Sulfur and Silicon and the Related Elements, (1989), 46(1-2), pp. 1-6.
Database CAPLUS on STN, Chemical Abstracts, (Columbus, Ohio, USA), CA 115:207974, Robinson et al, 'Preparation of azaoxindole-1-carboxamindes as antiinflammatories and analgesics', abs of European Patent Application, 53 pages.

* cited by examiner

Primary Examiner — D. Margaret Seaman
Assistant Examiner — Niloofar Rahmani
(74) Attorney, Agent, or Firm — Peter F. Corless; Dwight D. Kim; Edwards Angell Palmer & Dodge LLP

(57) ABSTRACT

Pyrrolo-pyridine, pyrrolo-pyrimidine and related heterocyclic compounds analogues of the formula:

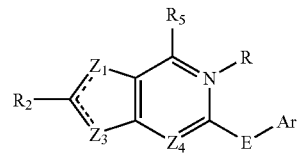

wherein R, $R_2$, $R_5$, E, $Z_1$, $Z_3$, $Z_4$, and Ar are defined herein. Such compounds are ligands of C5a receptors. Preferred pyrrolo-pyridine, pyrrolo-pyrimidine and related heterocyclic compounds of the invention bind to C5a receptors with high affinity and exhibit neutral antagonist or inverse agonist activity at C5a receptors. The present invention also relates to pharmaceutical compositions comprising such compounds, and to the use of such compounds in treating a variety of inflammatory, cardiovascular, and immune system disorders. In addition, the present invention provides labeled pyrrolo-pyridine, pyrrolo-pyrimidine and related heterocyclic compounds, which are useful as probes for the localization of C5a receptors.

25 Claims, No Drawings

PYRROLO-PYRIDINE, PYRROLO-PYRIMIDINE AND RELATED HETEROCYCLIC COMPOUNDS

FIELD OF THE INVENTION

This invention relates generally to pyrrolo-pyridine, pyrrolo-pyrimidine and related heterocyclic compounds that act as modulators of mammalian complement C5a receptors, and to pharmaceutical compositions comprising such modulators. The present invention further relates to the use of such modulators in treating a variety of inflammatory and immune system disorders and as probes for the localization of C5a receptors.

BACKGROUND OF THE INVENTION

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interaction with the C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions (e.g., phagocytosis). Additionally, C5a stimulates the release of inflammatory mediators (e.g., histamines, TNF-α, IL-1, IL-6, IL-8, prostaglandins, and leukotrienes) and the release of lysosomal enzymes and other cytotoxic components from granulocytes. Among its other actions, C5a also promotes the production of activated oxygen radicals and the contraction of smooth muscle.

Considerable experimental evidence implicates increased levels of C5a in a number of autoimmune diseases and inflammatory and related disorders. Agents that block the binding of C5a to its receptor other agents, including inverse agonists, which modulate signal transduction associated with C5a-receptor interactions, can inhibit the pathogenic events, including chemotaxis, associated with anaphylatoxin activity contributing to such inflammatory and autoimmune conditions. The present invention provides such agents, and has further related advantages.

SUMMARY OF THE INVENTION

The present invention provides compounds that modulate, and preferably inhibit, C5a receptor activation and/or C5a receptor-mediated signal transduction. Such C5a receptor modulators are preferably high affinity C5a receptor ligands and act as antagonists (e.g., inverse agonists) of complement C5a receptors, such as human C5a receptors. Within certain aspects, C5a receptor modulators provided herein are pyrrolo-pyridine, pyrrolo-pyrimidine and related heterocyclic compounds of Formula I and Formula II or a pharmaceutically acceptable salt thereof.

Within certain aspects, compounds provided herein are pyrrolo-pyridine, pyrrolo-pyrimidine and related heterocyclic compounds analogues of Formula I:

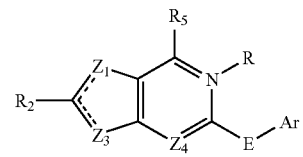

Formula I or a pharmaceutically acceptable salt thereof, wherein:
E is a single bond, O, $S(O)_m$, $NR_6$ or $CR_6R_7$;
$R_6$ and $R_7$ are independently hydrogen or $C_1$-$C_4$alkyl;
m is 0, 1, or 2;
Ar is chosen from:
phenyl which is mono-, di-, or tri-substituted, 1-naphthyl and 2-naphthyl, each of which is optionally mono-, di-, or tri-substituted, and optionally mono-, di-, or tri-substituted heteroaryl, said heteroaryl having from 1 to 3 rings, 5 to 7 ring members in each ring and, in at least one of said rings, from 1 to about 3 heteroatoms selected from the group consisting of N, O, and S;
the group:

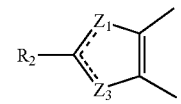

represents an aromatic 5-membered ring system containing exactly one heteroatom, wherein:
$Z_1$ is $CR_1$ or $NR_1''$;
$Z_3$ is $CR_3$ or $NR_3''$;
$R_1$ and $R_1''$ are chosen from $C_1$-$C_{10}$alkyl, $C_2$-$C_{10}$alkenyl, $C_2$-$C_{10}$alkynyl, $C_3$-$C_7$cycloalkyl, $(C_3$-$C_7$cycloalkyl$)C_1$-$C_4$alkyl, three to nine membered heterocycloalkyl, (three to nine membered heterocycloalkyl)$C_1$-$C_4$alkyl, aryl, (aryl)$C_1$-$C_4$alkyl, heteroaryl, (heteroaryl)$C_1$-$C_4$alkyl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$ alkoxy$C_1$-$C_6$alkyl, $C_1$-$C_6$haloalkoxy, $C_5$-$C_7$heteroaryl, mono- and di-$(C_1$-$C_6)$alkylamino, and —$XR_C$;
$R_2$ is chosen from hydrogen, halogen, hydroxy, amino, cyano, nitro, $C_1$-$C_6$alkyl, halo$(C_1$-$C_6)$alkyl, $C_1$-$C_6$alkoxy, amino$(C_1$-$C_6)$alkyl, and mono and di$(C_1$-$C_6)$alkylamino;
$R_3$ and $R_3''$ are independently chosen from $C_4$-$C_{10}$alkyl, halo$(C_4$-$C_{10})$alkyl, $C_4$-$C_{10}$ alkoxy, amino$(C_4$-$C_{10})$alkyl, hydroxy$(C_4$-$C_{10})$alkyl, mono and di$(C_4$-$C_{10})$alkylamino, $C_3$-$C_7$cycloalkyl, $(C_3$-$C_7$cycloalkyl$)C_1$-$C_4$alkyl, three to nine membered heterocycloalkyl, (three to nine membered heterocycloalkyl)$C_1$-$C_4$alkyl, aryl, and heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-$(C_1$-$C_6)$alkylamino, —$XR_C$, and Y;
$Z_4$ is NR or $CR_4$;
R is absent or oxygen;

$R_4$ and $R_5$ are independently chosen from hydrogen, halogen, hydroxy, amino, cyano, $C_1$-$C_{10}$alkyl, $C_2$-$C_{10}$alkenyl, $C_2$-$C_{10}$alkynyl, halo($C_1$-$C_{10}$)alkyl, $C_1$-$C_{10}$alkoxy, amino ($C_1$-$C_{10}$)alkyl, hydroxy($C_1$-$C_{10}$)alkyl, ($C_2$-$C_{10}$)alkoxyalkyl mono and di($C_1$-$C_{10}$)alkylamino, $C_3$-$C_7$cycloalkyl, ($C_3$-$C_7$cycloalkyl)$C_1$-$C_4$alkyl, three to nine membered heterocycloalkyl, (three to nine membered heterocycloalkyl)$C_1$-$C_4$alkyl, $(CH_2)_p$COOH, $(CH_2)_p$COOR$_A$, $(CH_2)_p$CONR$_A$R$_B$, $(CH_2)_p$S(O)$_m$R$_A$, S(O)$_m$NR$_A$R$_B$, aryl, and heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$) alkylamino, —XR$_C$, and Y;

$R_A$ is independently selected at each occurrence from halogen, cyano, nitro, halo($C_1$-$C_6$)alkyl, halo($C_1$-$C_6$)alkoxy, hydroxy, amino, $C_1$-$C_6$alkyl substituted with 0-2 R$_B$, $C_2$-$C_6$alkenyl substituted with 0-2 R$_B$, $C_2$-$C_6$alkynyl substituted with 0-2 R$_B$, $C_3$-$C_7$cycloalkyl substituted with 0-2 R$_B$, ($C_3$-$C_7$cycloalkyl) $C_1$-$C_4$alkyl substituted with 0-2 R$_B$, $C_1$-$C_6$alkoxy substituted with 0-2 R$_B$, —NH($C_1$-$C_6$alkyl) substituted with 0-2 R$_B$, —N($C_1$-$C_6$alkyl)($C_1$-$C_6$alkyl) each $C_1$-$C_6$alkyl independently substituted with 0-2 R$_B$, —XR$_C$, and Y;

$R_B$ is independently selected at each occurrence from the group consisting of halogen, hydroxy, cyano, amino, $C_1$-$C_4$alkyl, —O($C_1$-$C_4$alkyl), —NH($C_1$-$C_4$alkyl), —N($C_1$-$C_4$alkyl) ($C_1$-$C_4$alkyl), —S(O)$_n$(alkyl), halo($C_1$-$C_4$)alkyl, halo($C_1$-$C_4$)alkoxy, CO($C_1$-$C_4$alkyl), CONH($C_1$-$C_4$alkyl), CON($C_1$-$C_4$alkyl)($C_1$-$C_4$alkyl), —XR$_C$, and Y;

$R_C$ and $R_D$, which may be the same or different, are independently selected at each occurrence from:
hydrogen, and
straight, branched, or cyclic alkyl groups, including (cycloalkyl)alkyl groups consisting of 1 to 8 carbon atoms, which straight, branched, or cyclic alkyl groups contain zero or one or more double or triple bonds, each of which 1 to 8 carbon atoms may be further substituted with one or more substituent(s) independently selected from oxo, hydroxy, halogen, cyano, amino, $C_1$-$C_6$alkoxy, —NH($C_1$-$C_6$alkyl), —N($C_1$-$C_6$alkyl)($C_1$-$C_6$alkyl), —NHC(=O)($C_1$-$C_6$alkyl), —N($C_1$-$C_6$alkyl)C(=O)($C_1$-$C_6$alkyl), —NHS(O)$_n$($C_1$-$C_6$alkyl), —S(O)$_n$($C_1$-$C_6$alkyl), —S(O)$_n$NH($C_1$-$C_6$alkyl), —S(O)$_n$N($C_1$-$C_6$alkyl)($C_1$-$C_6$alkyl), and Z;

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, $C_1$-$C_4$alkyl, —O($C_1$-$C_4$alkyl), —NH($C_1$-$C_4$alkyl), —N($C_1$-$C_4$alkyl) ($C_1$-$C_4$alkyl), and —S(O)$_n$(alkyl), wherein said 3- to 7-membered heterocyclic groups contain one or more heteroatom(s) independently selected from N, O, and S, with the point of attachment being either carbon or nitrogen; and n is independently selected at each occurrence from 0, 1, and 2.

Within certain other aspects, compounds provided herein are pyrrolo-pyridine, pyrrolo-pyrimidine and related heterocyclic compounds analogues of Formula II:

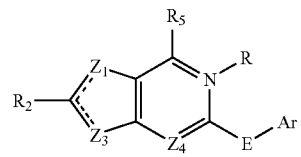

Formula II or a pharmaceutically acceptable salt thereof, wherein:
E is a single bond, O, S(O)$_m$, NR$_6$ or CR$_6$R$_7$;
$R_6$ and $R_7$ are independently hydrogen or $C_1$-$C_4$ alkyl;
m is 0, 1, or 2;
Ar is chosen from:
phenyl which is mono-, di-, or tri-substituted, 1-naphthyl and 2-naphthyl, each of which is optionally mono-, di-, or tri-substituted, and optionally mono-, di-, or tri-substituted heteroaryl, said heteroaryl having from 1 to 3 rings, 5 to 7 ring members in each ring and, in at least one of said rings, from 1 to about 3 heteroatoms selected from the group consisting of N, O, and S;
the group:

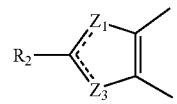

represents an aromatic 5-membered ring system containing exactly one heteroatom, wherein:
$Z_1$ is CR$_1$ or NR$_1$";
$Z_3$ is CR$_3$ or NR$_3$";
$R_1$ and $R_1$" are chosen from (aryl)$C_0$-$C_4$alkyl and (heteroaryl)$C_0$-$C_4$alkyl, each of which is substituted with 0 or more substituents independently chosen from halogen, hydroxy, amino, oxo, cyano, $C_1$-$C_6$alkyl, $C_1$-$C_6$alkoxy, phenoxy, benzyloxy, $C_1$-$C_6$hydroxyalkyl, $C_2$-$C_6$alkoxyalkyl, $C_1$-$C_6$haloalkoxy, $C_3$-$C_7$cycloalkyl, three to seven membered heterocycloalkyl, $C_5$-$C_7$heteroaryl, phenyl, mono- and di-($C_1$-$C_6$)alkylamino, mono- and di-($C_1$-$C_6$)alkylamino($C_1$-$C_6$)alkoxy, —(C(R$_x$)$_2$)$_p$C(O)R$_A$, and —(C(R$_x$)$_2$)$_p$S(O)$_2$R$_C$ and —XR$_C$;

$R_2$ is chosen from hydrogen, halogen, hydroxy, amino, cyano, nitro, $C_1$-$C_6$alkyl, halo($C_1$-$C_6$)alkyl, $C_1$-$C_6$alkoxy, amino ($C_1$-$C_6$)alkyl, and mono and di($C_1$-$C_6$)alkylamino;

$R_3$ is chosen from hydrogen, halogen, hydroxy, amino, cyano, $(CH_2)_p$C(O)R$_A$, $(CH_2)_p$S(O)$_m$R$_A$, $C_1$-$C_{10}$alkyl, halo($C_1$-$C_{10}$)alkyl, $C_1$-$C_{10}$alkoxy, amino($C_1$-$C_{10}$)alkyl, hydroxy($C_1$-$C_{10}$)alkyl, ($C_2$-$C_{10}$)alkoxyalkyl mono and di($C_1$-$C_{10}$)alkylamino, $C_3$-$C_7$cycloalkyl, ($C_3$-$C_7$cycloalkyl)$C_1$-$C_4$alkyl, three to nine membered heterocycloalkyl, (three to nine membered heterocycloalkyl)$C_1$-$C_4$alkyl, aryl, and heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$) alkylamino, —XR$_C$, and Y;

$R_3$" is chosen from hydrogen, $C_1$-$C_{10}$alkyl, halo($C_1$-$C_{10}$) alkyl, $C_1$-$C_{10}$alkoxy, amino($C_1$-$C_{10}$)alkyl, hydroxy($C_1$-$C_{10}$)alkyl, ($C_2$-$C_{10}$)alkoxyalkyl, $(CH_2)_p$C(O)R$_A$, $(CH_2)_p$S (O)$_m$R$_A$, mono and di(C$_1$-C$_{10}$)alkylamino, C$_3$-C$_7$cycloakyl, (C$_3$-C$_7$cycloakyl)C$_1$-C$_4$alkyl, three to nine membered heterocycloalkyl, (three to nine membered heterocycloalkyl)C$_1$-C$_4$alkyl, aryl, and heteroaryl, each of which is substituted with 0 or more substituents independently chosen from halogen, hydroxy, amino, oxo, cyano, C$_1$-C$_6$alkyl, C$_1$-C$_6$alkoxy, C$_1$-C$_6$hydroxyalkyl, C$_1$-C$_6$alkoxyC$_1$-C$_6$alkyl, C$_1$-C$_6$haloalkoxy, C$_5$-C$_7$heteroaryl, mono- and di-(C$_1$-C$_6$)alkylamino, —XR$_C$, and Y;

p is 0, 1, 2, 3, or 4;

Z$_4$ is NR or CR$_4$;

R is absent or oxygen;

R$_4$ and R$_5$ are independently chosen from hydrogen, halogen, cyano, nitro, amino, mono or di(C$_1$-C$_6$alkyl)amino, C$_1$-C$_6$alkyl, C$_2$-C$_6$alkenyl, C$_2$-C$_6$alkynyl, (C$_3$-C$_7$cycloalkyl)C$_0$-C$_4$alkyl, C$_3$-C$_7$cycloalkoxy, haloC$_1$-C$_6$alkyl, halo(C$_1$-C$_6$)alkoxy, C$_1$-C$_6$alkoxy, S(O)$_n$(C$_1$-C$_6$alkyl), phenyl, 5-7 membered heteroaryl, and three to seven membered heterocycloalkyl, each of which is substituted with between 0 and 4 groups selected halogen, hydroxy, amino, oxo, cyano, C$_1$-C$_4$alkyl, C$_1$-C$_4$alkoxy, and mono- and di(C$_1$-C$_4$)alkylamino;

R$_x$ is independently selected at each occurrence from hydrogen or C$_1$-C$_4$alkyl;

R$_A$ is independently selected at each occurrence from halogen, cyano, nitro, halo(C$_1$-C$_6$)alkyl, halo(C$_1$-C$_6$)alkoxy, hydroxy, amino, C$_1$-C$_6$alkyl substituted with 0-2 R$_B$, C$_2$-C$_6$alkenyl substituted with 0-2 R$_B$, C$_2$-C$_6$alkynyl substituted with 0-2 R$_B$, C$_3$-C$_7$cycloalkyl substituted with 0-2 R$_B$, (C$_3$-C$_7$cycloalkyl)C$_1$-C$_4$alkyl substituted with 0-2 R$_B$, C$_1$-C$_6$alkoxy substituted with 0-2 R$_B$, —NH(C$_1$-C$_6$alkyl) substituted with 0-2 R$_B$, —N(C$_1$-C$_6$alkyl)(C$_1$-C$_6$alkyl) each C$_1$-C$_6$alkyl independently substituted with 0-2 R$_B$, —XR$_C$, and Y;

R$_B$ is independently selected at each occurrence from the group consisting of halogen, hydroxy, cyano, amino, C$_1$-C$_4$alkyl, —O(C$_1$-C$_4$alkyl), —NH(C$_1$-C$_4$alkyl), —N(C$_1$-C$_4$ alkyl)(C$_1$-C$_4$alkyl), —S(O)$_n$(alkyl), halo(C$_1$-C$_4$)alkyl, halo(C$_1$-C$_4$)alkoxy, CO(C$_1$-C$_4$alkyl), CONH(C$_1$-C$_4$alkyl), CON(C$_1$-C$_4$alkyl)(C$_1$-C$_4$alkyl), —XR$_C$, and Y;

R$_C$ and R$_D$, which may be the same or different, are independently selected at each occurrence from:
hydrogen, and
straight, branched, or cyclic alkyl groups, including (cycloalkyl)alkyl groups consisting of 1 to 8 carbon atoms, which straight, branched, or cyclic alkyl groups contain zero or one or more double or triple bonds, each of which 1 to 8 carbon atoms may be further substituted with one or more substituent(s) independently selected from oxo, hydroxy, halogen, cyano, amino, C$_1$-C$_6$alkoxy, —NH(C$_1$-C$_6$alkyl), —N(C$_1$-C$_6$alkyl)(C$_1$-C$_6$alkyl), —NHC(=O)(C$_1$-C$_6$alkyl), —N(C$_1$-C$_6$alkyl)C(=O)(C$_1$-C$_6$alkyl), —NHS(O)$_n$(C$_1$-C$_6$alkyl), —S(O)$_n$(C$_1$-C$_6$alkyl), —S(O)$_n$NH(C$_1$-C$_6$alkyl), —S(O)$_n$N(C$_1$-C$_6$alkyl)(C$_1$-C$_6$alkyl), and Z;

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, C$_1$-C$_4$alkyl, —O(C$_1$-C$_4$alkyl), —NH(C$_1$-C$_4$alkyl), —N(C$_1$-C$_4$alkyl)(C$_1$-C$_4$alkyl), and —S(O)$_n$(alkyl), wherein said 3- to 7-membered heterocyclic groups contain one or more heteroatom(s) independently selected from N, O, and S, with the point of attachment being either carbon or nitrogen;

p is independently selected at each occurrence from 0, 1, 2, and 3; and n is independently selected at each occurrence from 0, 1, and 2.

In certain embodiments, C5a receptor modulators provided herein exhibit high affinity for C5a receptor (i.e., an affinity constant for binding to C5a receptor of less than 1 micromolar) or very high affinity for C5a receptor (i.e., an affinity constant for binding to the C5a receptor of less than 100 nanomolar). In certain embodiments, such modulators exhibit an affinity for human C5a receptor that is higher than for rat or mouse C5a receptor, preferably at least five times higher, more preferably ten times higher. Affinity of a compound or salt for C5a receptor may be determined, for example, via a radioligand binding assay, such as the assay provided in Example 32.

Within certain aspects, modulators as described herein are C5a receptor antagonists, such as inverse agonists. Certain such compounds exhibit an EC$_{50}$ of 1 micromolar or less, 500 nM or less, 100 nM or less, or 25 nM or less, in a standard in vitro C5a receptor-mediated chemotaxis assay (such as the assay provided in Example 27) or a calcium mobilization assay (as described in Example 34).

Within further aspects, C5a receptor antagonists are essentially free of C5a receptor agonist activity (i.e., exhibit less than 5% agonist activity in a GTP binding assay as described in Example 33).

The present invention further provides, within other aspects, pharmaceutical compositions comprising at least one C5a receptor modulator as described herein, in combination with a physiologically acceptable carrier or excipient. Processes for preparing such pharmaceutical compositions are also provided. Such compositions are particularly useful in the treatment of C5a-mediated inflammation, such as inflammation associated with various inflammatory and immune system disorders.

Within further aspects, methods are provided for inhibiting signal-transducing activity of a cellular C5a receptor, comprising contacting a cell expressing a C5a receptor with at least one C5a receptor modulator as described herein, and thereby reducing signal transduction by the C5a receptor.

Methods are further provided for inhibiting binding of C5a to C5a receptor in vitro, comprising contacting C5a receptor with at least one C5a receptor modulator as described herein, under conditions and in an amount sufficient to detectably inhibit C5a binding to C5a receptor.

The present invention further provides methods for inhibiting binding of C5a to C5a receptor in a human patient, comprising contacting cells expressing C5a receptor with at least one C5a receptor modulator as described herein.

Within further aspects, the present invention provides methods for treating a patient in need of anti-inflammatory treatment or immunomodulatory treatment. Such methods generally comprise administering to the patient a C5a receptor modulatory amount of a C5a receptor modulator as described herein. Treatment of humans, domesticated companion animals (pets) or livestock animals suffering such conditions is contemplated by the present invention. In certain such aspects, methods are provided for treating a patient suffering from cystic fibrosis, rheumatoid arthritis, psoriasis, cardiovascular disease, reperfusion injury, or bronchial asthma comprising administering to the patient a C5a receptor modulatory amount of a C5a receptor modulator as described herein. In further such aspects, methods are provided for treating a patient suffering from stroke, myocardial infarction, atherosclerosis, ischemic heart disease, or ischemia-reperfusion injury comprising administering to the patient a C5a receptor modulatory amount of a C5a receptor modulator as described herein.

The present invention further provides methods for inhibiting C5a receptor-mediated cellular chemotaxis (preferably leukocyte (e.g., neutrophil) chemotaxis), comprising contacting mammalian white blood cells with a C5a receptor modulatory amount of a C5a receptor modulator as described herein. In certain embodiments, the white blood cells are primate white blood cells, such as human white blood cells.

Within further aspects, the present invention provides methods for using a C5a receptor modulator as described herein as a probe for the localization of receptors, particularly C5a receptors. Such localization may be achieved, for example, in tissue sections (e.g., via autoradiography) or in vivo (e.g., via positron emission tomography, PET, or single positron emission computed tomography, SPECT, scanning and imaging). Within certain such aspects, the present invention provides methods for localizing C5a receptors in a tissue sample, comprising: (a) contacting the tissue sample containing C5a receptors with a detectably labeled compound as described herein under conditions that permit binding of the compound to C5a receptors; and (b) detecting the bound compound. Such methods may, optionally, further comprise a step of washing the contacted tissue sample, prior to detection. Suitable detectable labels include, for example, radiolabels such as $^{125}$I, tritium, $^{14}$C, $^{32}$P and $^{99}$Tc.

The present invention also provides packaged pharmaceutical preparations, comprising: (a) a pharmaceutical composition as described herein in a container; and (b) instructions for using the composition to treat a patient suffering from one or more conditions responsive to C5a receptor modulation, such as rheumatoid arthritis, psoriasis, cardiovascular disease, reperfusion injury, bronchial asthma, stroke, myocardial infarction, atherosclerosis, ischemic heart disease, or ischemia-reperfusion injury.

In yet another aspect, the present invention provides methods for preparing the compounds disclosed herein, including the intermediates.

These and other aspects of the present invention will become apparent upon reference to the following detailed description.

DETAILED DESCRIPTION OF THE INVENTION

As noted above, the present invention provides pyrrolo-pyridine, pyrrolo-pyrimidine and related heterocyclic compounds that modulate C5a receptor activation and/or C5a receptor-mediated signal transduction. Such compounds may be used in vitro or in vivo to modulate (preferably inhibit) C5a receptor activity in a variety of contexts.

Chemical Description and Terminology

Compounds provided herein are generally described using standard nomenclature. For compounds having asymmetric centers, it should be understood that (unless otherwise specified) all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope (i.e., an atom having the same atomic number but a different mass number). By way of general example, and without limitation, isotopes of hydrogen include tritium and deuterium and isotopes of carbon include $^{11}$C, $^{13}$C, and $^{14}$C.

Certain compounds are described herein using a general formula that includes variables (e.g. $R_1$-$R_5$, $R_8$-$R_{13}$, Ar). Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R groups and R* at each occurrence is selected independently from the definition of R*. Also, combinations of substituents and/or variables are permissible only if such combinations result in stable compounds.

The term "pyrrolo-pyridine" and "pyrrolo-pyrimidine," as used herein, refers to compounds of Formula I and Formula II, as well as pharmaceutically acceptable forms thereof. Such compounds may, but need not, further satisfy one or more additional Formulas provided herein.

"Pharmaceutically acceptable forms" of the compounds recited herein include pharmaceutically acceptable salts, esters, hydrates, clathrates and prodrugs of such compounds. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences,* 17th ed., Mack Publishing Company, Easton, Pa., p. 1418 (1985).

A "prodrug" is a compound that may not fully satisfy the structural requirements of Formula I and Formula II (or another Formula as provided herein) but is modified in vivo, following administration to a patient, to produce such a compound. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "C5a receptor modulatory amount" is an amount that, upon administration, results in a concentration of C5a receptor modulator at a C5a receptor that is sufficient to inhibit chemotaxis of white blood cells in an in vitro assay and/or alter C5a receptor activity or activation as measured by an in vitro calcium mobilization assay. In a chemotaxis assay (see Example 27), the level of C5a-induced chemotaxis observed in a control assay (i.e., one to which a compound as provided herein has not been added) is significantly higher (measured as $p \leq 0.05$ using a conventional parametric statistical analysis method such as a student's T-test) than the level observed in an assay to which a compound or salt thereof as described herein has been added. Within such an assay, the C5a is generally from the same species as the cells used in the assay. In a calcium mobilization assay (see Example 34), a concentration of compound that alters C5a receptor activity or activation may inhibit C5a-induced calcium mobilization or may itself increase or decrease C5a receptor-mediated calcium mobilization in the absence of C5a.

A "therapeutically effective amount" is an amount of a compound or salt thereof as provided herein that, upon administration, results in a discernible benefit in a patient. Such benefit may be confirmed using standard clinical procedures.

A "substituent," as used herein, refers to a molecular moiety that is covalently bonded to an atom within a molecule of interest. For example, a "ring substituent" may be a moiety such as a halogen, alkyl group, haloalkyl group or other substituent described herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Optional substitution may also be indicated by the phrase "substituted with from 0 to X substituents," in which X is the maximum number of substituents.

Suitable substituents include, for example, halogen, cyano, amino, hydroxy, nitro, azido, carboxamido, —COOH, $SO_2NH_2$, alkyl (e.g., $C_1$-$C_8$alkyl), alkenyl (e.g., $C_2$-$C_8$alkenyl), alkynyl (e.g., $C_2$-$C_8$alkynyl), alkoxy (e.g., $C_1$-$C_8$alkoxy), alkyl ether (e.g., $C_2$-$C_8$alkyl ether), alkylthio (e.g., $C_1$-$C_8$alkylthio), haloalkyl (e.g., $C_1$-$C_8$haloalkyl), hydroxyalkyl (e.g., $C_1$-$C_8$hydroxyalkyl), aminoalkyl (e.g., $C_1$-$C_8$aminoalkyl), haloalkoxy (e.g., $C_1$-$C_8$haloalkoxy), alkanoyl (e.g., $C_1$-$C_8$alkanoyl), alkanone (e.g., $C_1$-$C_8$alkanone), alkanoyloxy (e.g., $C_1$-$C_8$alkanoyloxy), alkoxycarbonyl (e.g., $C_1$-$C_8$alkoxycarbonyl), mono- and di-($C_1$-$C_8$alkyl)amino, mono- and di-($C_1$-$C_8$alkyl)amino$C_1$-$C_8$alkyl, mono- and di-($C_1$-$C_8$alkyl)carboxamido, mono- and di-($C_1$-$C_8$alkyl)sulfonamido, alkylsulfinyl (e.g., $C_1$-$C_8$alkylsulfinyl), alkylsulfonyl (e.g., $C_1$-$C_8$alkylsulfonyl), aryl (e.g., phenyl), arylalkyl (e.g., ($C_6$-$C_{18}$aryl)$C_1$-$C_8$alkyl, such as benzyl and phenethyl), aryloxy (e.g., $C_6$-$C_{18}$aryloxy such as phenoxy), arylalkoxy (e.g., ($C_6$-$C_{18}$aryl)$C_1$-$C_8$alkoxy) and/or 3- to 8-membered heterocyclic groups such as coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino or pyrrolidinyl. Certain groups within the formulas provided herein are optionally substituted with from 1 to 3, 1 to 4 or 1 to 5 independently selected substituents.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, and where specified, having the specified number of carbon atoms. Thus, the term $C_1$-$C_6$alkyl, as used herein, indicates an alkyl group having from 1 to 6 carbon atoms. "$C_0$-$C_4$alkyl" refers to a bond or a $C_1$-$C_4$alkyl group. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. In certain embodiments, preferred alkyl groups are methyl, ethyl, propyl, butyl, and 3-pentyl. "Aminoalkyl" is an alkyl group as defined herein substituted with one or more —$NH_2$ substituents. "Hydroxyalkyl" is a hydroxy group as defined herein substituted with one or more —OH substituents.

"Alkenyl" refers to a straight or branched hydrocarbon chain comprising one or more unsaturated carbon-carbon bonds, such as ethenyl and propenyl. Alkenyl groups include $C_2$-$C_8$alkenyl, $C_2$-$C_6$alkenyl and $C_2$-$C_4$alkenyl groups (which have from 2 to 8, 2 to 6 or 2 atoms, respectively), such as ethenyl, allyl or isopropenyl.

"Alkynyl" refers to straight or branched hydrocarbon chains comprising one or more triple carbon-carbon bonds. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively. Alkynyl groups include for example groups such as ethynyl and propynyl.

By "alkoxy," as used herein, is meant an alkyl, alkenyl or alkynyl group as described above attached via an oxygen bridge. Alkoxy groups include $C_1$-$C_6$alkoxy and $C_1$-$C_4$alkoxy groups, which have from 1 to 6 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups. Similarly "alkylthio" refers to an alkyl, alkenyl or alkynyl group as described above attached via a sulfur bridge.

The term "alkanoyl" refers to an alkyl group as defined above attached through a carbonyl bridge. Alkanoyl groups include $C_2$-$C_8$alkanoyl, $C_2$-$C_6$alkanoyl and $C_2$-$C_4$alkanoyl groups, which have from 2 to 8, 2 to 6 or 2 to 4 carbon atoms, respectively. "$C_1$alkanoyl" refers to —(C=O)—H, which (along with $C_2$-$C_8$alkanoyl) is encompassed by the term "$C_1$-$C_8$alkanoyl." Ethanoyl is $C_2$alkanoyl.

An "alkanone" is an alkyl group as defined above with the indicated number of carbon atoms substituted at least one position with an oxo group. "$C_3$-$C_8$alkanone," "$C_3$-$C_6$alkanone" and "$C_3$-$C_4$alkanone" refer to an alkanone having from 3 to 8, 6 or 4 carbon atoms, respectively. By way of example, a $C_3$ alkanone group has the structure —$CH_2$—(C=O)—$CH_3$.

Similarly, "alkyl ether" refers to a linear or branched ether substituent linked via a carbon-carbon bond. Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. By way of example, a $C_2$ alkyl ether group has the structure —$CH_2$—O—$CH_3$.

The term "alkoxycarbonyl" refers to an alkoxy group linked via a carbonyl (i.e., a group having the general structure —C(=O)—O-alkyl). Alkoxycarbonyl groups include $C_2$-$C_8$, $C_2$-$C_6$ and $C_2$-$C_4$alkoxycarbonyl groups, which have from 2 to 8, 6 or 4 carbon atoms, respectively.

"Alkanoyloxy," as used herein, refers to an alkanoyl group linked via an oxygen bridge (e.g., a group having the general structure —O—C(=O)-alkyl). Alkanoyloxy groups include $C_2$-$C_8$, $C_2$-$C_6$ and $C_2$-$C_4$alkanoyloxy groups, which have from 2 to 8, 6 or 4 carbon atoms, respectively.

"Alkylamino" refers to a secondary or tertiary amine having the general structure —NH-alkyl or —N(alkyl)(alkyl), wherein each alkyl may be the same or different. Such groups include, for example, mono- and di-($C_1$-$C_8$alkyl)amino groups, in which each alkyl may be the same or different and may contain from 1 to 8 carbon atoms, as well as mono- and di-($C_1$-$C_6$alkyl)amino groups and mono- and di-($C_1$-$C_4$alkyl) amino groups. "Mono- or di-($C_1$-$C_4$alkylamino)$C_0$-$C_4$alkyl" refers to a mono- and di-($C_1$-$C_4$alkyl)amino group that is linked via a direct bond or a $C_1$-$C_4$ alkyl group (i.e., a group having the general structure —$C_0$-$C_4$alkyl-NH-alkyl or —$C_0$-$C_4$alkyl-N(alkyl)(alkyl), in which each alkyl may be the same or different. Similarly, "alkylaminoalkoxy" refers to an alkylamino group linked via an alkoxy group.

The term "aminocarbonyl" or "carboxamido" refers to an amide group (i.e., —(C=O)$NH_2$). "Mono- or di-($C_1$-$C_6$alkyl)aminocarbonyl" refers to an amide group in which one or both of the hydrogen atoms is replaced with an independently chosen $C_1$-$C_6$alkyl. Such groups may also be indicated by "—C(=O)NHalkyl" or "—C(=O)N(alkyl)alkyl."

The term "halogen" refers to fluorine, chlorine, bromine and iodine. A "haloalkyl" is a branched or straight-chain alkyl group, substituted with 1 or more halogen atoms (e.g., "halo$C_1$-$C_8$alkyl" groups have from 1 to 8 carbon atoms; "halo$C_1$-$C_6$alkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Within certain compounds provided herein, not more than 5 or 3 haloalkyl groups are present. The term "haloalkoxy" refers to a haloalkyl group as defined above attached via an oxygen bridge. "Halo$C_1$-$C_8$alkoxy" groups have 1 to 8 carbon atoms.

A "carbocycle" is any saturated, partially saturated, or aromatic group having 1 or 2 fused, pendant or spiro rings, with 3 to 8 atoms in each ring, and with all ring members being carbon. The term "carbocycle" encompasses aromatic groups such as phenyl and naphthyl, as well as groups that comprise both aromatic and nonaromatic rings (e.g., tetrahydronaphthyl), and groups with saturated and partially saturated rings (such as cyclohexyl and cyclohexenyl). When substitutions are indicated, carbocycles may be substituted on any ring atom where such substitution results in a stable compound. The term "$C_3$-$C_{10}$carbocycle" refers to such groups having from 3 to 10 ring members. A "$C_3$-$C_{10}$carbocycle$C_0$-$C_4$alkyl" group is a $C_3$-$C_{10}$carbocycle that is linked via a direct bond or a $C_1$-$C_4$alkyl group.

Certain carbocycles are "cycloalkyl" (i.e., a saturated or partially saturated carbocycle). Such groups typically contain from 3 to about 8 ring carbon atoms; in certain embodiments, such groups have from 3 to 7 ring carbon atoms. Examples of cycloalkyl groups include cyclopropyl, cyclobutyl, cyclopentyl and cyclohexyl, as well as such groups modified by the presence of one or more double or triple bonds (e.g., cyclohexenyl) and bridged or caged saturated ring groups such as norbornane or adamantane. If substituted, any ring carbon atom may be bonded to any indicated substituent.

In the term "(cycloalkyl)alkyl", "cycloalkyl" and "alkyl" are as defined above, and the point of attachment is on the alkyl group. This term encompasses, but is not limited to, cyclopropylmethyl, cyclohexylmethyl and cyclohexylethyl. "($C_3$-$C_7$cycloalkyl)$C_0$-$C_4$alkyl" refers to 3- to 7-membered cycloalkyl rings that are linked via a direct bond or a $C_1$-$C_4$alkyl.

Other carbocycles are "aryl" (i.e., carbocycles that comprise at least one aromatic ring). In addition to the aromatic ring(s), additional non-aromatic ring(s) may be present in an aryl group. Representative aryl groups include phenyl, naphthyl (e.g., 1-naphthyl and 2-naphthyl), biphenyl, tetrahydronaphthyl and indanyl.

The term "arylalkyl" refers to an aryl group that is linked via an alkyl group. Certain arylalkyl groups are aryl$C_0$-$C_2$alkyl, in which an aryl group is linked via a direct bond or a methylene or ethylene moiety. Such groups include, for example, groups in which phenyl or naphthyl is linked via a bond or $C_1$-$C_2$alkyl, such as benzyl, 1-phenyl-ethyl and 2-phenyl-ethyl.

The term "aryloxy" refers to an aryl group linked via a an oxygen (i.e., a group having the general structure —O-aryl). Phenoxy is a representative aryloxy group.

A "heteroatom" is an atom other than carbon, such as oxygen, sulfur or nitrogen.

The term "heterocycle" or "heterocyclic group" is used to indicate saturated, partially unsaturated, or aromatic groups having 1 or 2 fused, pendent or spiro rings, with 3 to 8 atoms in each ring, and in at least one ring from 1 to 4 heteroatoms independently selected from N, O and S, with remaining atoms being carbon. Certain heterocycles are 3- to 10-membered monocyclic or bicyclic groups; other are 4- to 6-membered monocyclic groups. The heterocyclic ring may be attached at any heteroatom or carbon atom that results in a stable structure, and may be substituted on carbon and/or nitrogen atom(s) if the resulting compound is stable. Any nitrogen and/or sulfur heteroatoms may optionally be oxidized, and any nitrogen may optionally be quaternized.

Variations on the term "(heterocycle)alkyl" refer to a heterocycle that is linked via a direct bond or alkyl group. Such groups include, for example, (3- to 10-membered heterocycle)$C_0$-$C_4$alkyl groups, in which the heterocycle contains from 3 to 10 ring members and is linked via a direct bond or $C_1$-$C_4$alkyl. Unless otherwise specified, the heterocycle portion of such groups may be saturated, partially saturated or aromatic. "(4- to 6-membered heterocycloalkyl)$C_0$-$C_4$alkyl" refers to a heterocycloalkyl group of 4 to 6 ring members that is linked via a direct bond or a $C_1$-$C_4$alkyl.

Certain heterocycles are "heteroaryl" (i.e., groups that comprise at least one aromatic ring having from 1 to 4 heteroatoms). When the total number of S and 0 atoms in a heteroaryl group exceeds 1, then these heteroatoms are not adjacent to one another; preferably the total number of S and 0 atoms in a heteroaryl is not more than 1, 2 or 3, more preferably 1 or 2 and most preferably not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

Other heterocycles are referred to herein as "heterocycloalkyl" (i.e., saturated or partially saturated heterocycles). Heterocycloalkyl groups have 1 or 2 rings, each with from 3 to about 8 ring atoms, and more typically from 5 to 7 ring atoms. Examples of heterocycloalkyl groups include morpholinyl, piperazinyl, piperidinyl and pyrrolidinyl.

Additional examples of heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"A C5a receptor" is a G-protein coupled receptor that specifically binds $C_5a$ peptide. Certain preferred C5a receptors are human, such as the protein product of the sequence that produces the human C5a receptor PCR product described by Gerard and Gerard (1991) *Nature* 349:614-17. The human C5a receptor may also be that described by Boulay (1991) *Biochemistry* 30(12):2993-99 (nucleotide sequence encoding the receptor is available at GENBANK Accession No. M62505). Non-primate C5a receptors include the rat C5a receptor (encoded by the nucleotide sequence having GENBANK Accession No. X65862, Y09613 or AB003042), canine C5a receptor (encoded by the nucleotide sequence having GENBANK Accession No. X65860), and guinea pig C5a receptor (encoded by the nucleotide sequence having GENBANK Accession No. U86103).

A "C5a receptor modulator" (also referred to herein as a "modulator") is any compound that modulates C5a receptor activation and/or activity (i.e., C5a receptor-mediated signal transduction, as measured using a C5a receptor-mediated chemotaxis, radioligand binding assay, or calcium mobilization assay as provided herein). In certain embodiments, such a modulator may be exhibit an affinity constant for binding to a C5a receptor of less than 1 micromolar in a standard $C_5a$ receptor radioligand binding assay; and/or an $EC_{50}$ of less than 1 micromolar in a standard C5a receptor-mediated chemotaxis assay or calcium mobilization assay. In other embodiments the a C5a receptor modulator may exhibit an affinity constant or $EC_{50}$ of less than 500 nM, 200 nM, 100 nM, 50 nM, 25 nM, 10 nM or 5 nM in such an assay. A modulator may be a C5a receptor agonist or antagonist, although, for certain purposes described herein, a modulator preferably inhibits C5a activation resulting from binding of C5a (i.e., the modulator is an antagonist). In addition, or alternatively, a modulator may act as an inverse agonist of C5a receptor. In certain embodiments, modulators provided herein modulate activation and/or activity of a primate C5a receptor, such as human C5a receptor, which may be a cloned, recombinantly expressed receptor or a naturally expressed receptor. For treating non-human animals of any particular species, a compound exhibiting high affinity for the C5a receptor of that particular species is preferred.

Certain C5a receptor modulators exhibit high activity in a standard in vitro C5a receptor mediated chemotaxis assay, as specified in Example 27, herein. Such compounds exhibit an $EC_{50}$ of 4 μM or less in such a standard C5a mediated chemotaxis assay, preferably an $EC_{50}$ of 1 μM or less in such an assay, more preferably an $EC_{50}$ of 0.1 μM or less in such an assay, and even more preferably and $EC_{50}$ of 10 nM or less in such an assay.

An "inverse agonist" of a C5a receptor is a compound that reduces the activity of the C5a receptor below its basal activity level in the absence of added C5a. Inverse agonists may also inhibit the activity of C5a at the C5a receptor, and/or may inhibit binding of C5a to the C5a receptor. The ability of a compound to inhibit the binding of C5a to the C5a receptor may be measured by a binding assay, such as the radioligand binding assay given in Example 32. The basal activity of the C5a receptor may be determined from a GTP binding assay, such as the assay of Example 33. The reduction of C5a receptor activity may also be determined from a GTP binding assay or a calcium mobilization assay such as the assay of Example 34.

A "neutral antagonist of the C5a receptor is a compound which inhibits the activity of $C_5a$ at the C5a receptor, but does not significantly change the basal activity of the $C_5a$ receptor. Neutral antagonists of the C5a receptor may inhibit the binding of C5a to the C5a receptor.

A "partial agonist" of the C5a receptor elevates the activity of the C5a receptor above the basal activity level of the receptor in the absence of C5a, but does not elevate the activity of the C5a receptor to the level brought about by saturating levels of the natural agonist, C5a. Partial agonist compounds may inhibit the binding of C5a to the C5a receptor. Partial agonists of the C5a receptor usually elevate the activity of the C5a receptor, producing a level of elevation ranging from 5% to 90% of the activity level brought about by receptor-saturating concentrations of the natural agonist, C5a.

C5A Receptor Modulators

As noted above, the present invention provides C5a receptor modulators. Such modulators may be used to alter C5a receptor activity in a variety of contexts, including in the treatment of patients suffering from diseases or disorders responsive to C5a receptor modulation, such as autoimmune disorders and inflammatory conditions. C5a receptor modulators may also be used within a variety of in vitro assays (e.g., assays for receptor activity), as probes for detection and localization of C5a receptor and as standards in assays of ligand binding and C5a receptor-mediated signal transduction.

C5a receptor modulators provided herein are pyrrolo-pyridine, pyrrolo-pyrimidine and related heterocyclic compounds of Formula I and Formula II (as well as pharmaceutically acceptable forms thereof) that detectably alter, preferably decrease, C5a receptor activation and/or signal transduction activity at submicromolar concentrations.

Certain preferred compounds provided by the invention include those compounds of Formula I or Formula II, in which $Z_1=NR_1"$, $Z_3=CR_3$, $Z_4=NR$, and R is absent at each occurrence. Such compounds are referred to herein as compounds of Formula III.

Certain preferred compounds provided by the invention include those compounds of Formula I or Formula II, in which $Z_1=CR_1$, $Z_3=CR_3''$, $Z_4=NR$, and R is absent at each occurrence. Such compounds are referred to herein as compounds of Formula IV.

Certain preferred compounds provided by the invention include those compounds of Formula I or Formula II, in which $Z_1=NR_1''$, $Z_3=CR_3$, $Z_4=CR_4$, and R is absent. Such compounds are referred to herein as compounds of Formula V.

Certain preferred compounds provided by the invention include those compounds of Formula I or Formula II, in which $Z_1=CR_1$, $Z_3=CR_3''$, $Z_4=CR_4$, and R is absent. Such compounds are referred to herein as compounds of Formula VI.

Thus, compounds of Formula I or Formula II include those compounds of Formula III-VI having the structures, as follows:

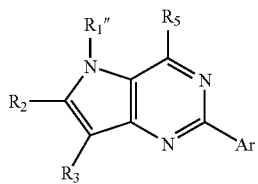

Formula III

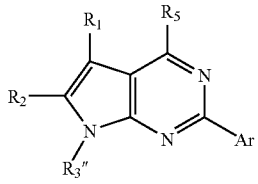

Formula IV

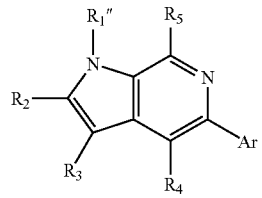

Formula V

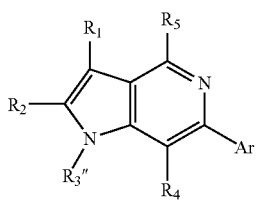

Formula VI

For each of the compounds and salts of Formula II-Formula VI, $R_1$, $R_1''$, $R_2$, $R_3$, $R_3''$, $R_4$, $R_5$, and Ar are as defined above for Formula I or Formula II.

In certain aspects, the invention provides compounds or salts of Formula I, or a subformula thereof, e.g., compounds or salts of Formula III-VI, in which $R_1$ and $R_1''$ are selected from $C_1$-$C_{10}$alkyl, $C_2$-$C_{10}$alkenyl, $C_3$-$C_7$cycloalkyl, ($C_3$-$C_7$cycloalkyl)$C_1$-$C_4$alkyl, phenyl, 1-naphthyl, 2-naphthyl, pyridinyl, pyrazinyl, pyrimidinyl, benzyl, pyridinyl-methyl, pyrazinyl-methyl, pyrimidinyl-methyl, each of which is substituted with between 0 and 2 substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$)alkylamino, and —$XR_C$;

In certain other aspects, the invention provides compounds of Formula I, or a subformula thereof, e.g., compounds or salts of Formula III-VI, or a subformula thereof, in which $R_1$ and $R_1''$ are selected from $C_1$-$C_{10}$alkyl, phenyl, 1-naphthyl, 2-naphthyl, pyridinyl, pyrazinyl, pyrimidinyl, benzyl, pyridinyl-methyl, pyrazinyl-methyl, pyrimidinyl-methyl, cyclohexane, indanyl, chromanyl, benzocycloheptenyl, and tetrahydronaphthyl, each of which is substituted with between 0 and 2 substituents independently selected from halogen, hydroxy, amino, oxo, cyano, $C_1$-$C_3$alkyl, $C_1$-$C_3$alkoxy, $C_1$-$C_3$hydroxyalkyl, $C_2$-$C_4$alkoxyalkyl, $C_1$-$C_2$haloalkoxy, $C_5$-$C_6$heteroaryl, mono- and di-($C_1$-$C_2$)alkylamino, COOH, COO($C_1$-$C_4$alkyl), CONH($C_1$-$C_4$alkyl), and CON($C_1$-$C_4$alkyl)$_2$.

In other aspects, the invention provides compounds or salts of Formula I, or a subformula thereof, in which Ar selected from the group consisting of phenyl, pyridyl and pyrimidinyl each of which is mono- di- or trisubstituted with substituents independently chosen from halogen, cyano, nitro, halo($C_1$-$C_6$)alkyl, halo($C_1$-$C_6$)alkoxy, hydroxy, amino, $C_1$-$C_6$alkyl, $C_2$-$C_6$ alkenyl, $C_2$-$C_6$alkynyl, $C_3$-$C_7$cycloalkyl, ($C_3$-$C_7$cycloalkyl)$C_1$-$C_4$alkyl, $C_1$-$C_6$alkoxy, mono- and di($C_1$-$C_6$alkyl)amino, amino($C_1$-$C_6$)alkyl, and mono- and di($C_1$-$C_6$alkyl)amino, wherein, in Ar, at least one of the positions ortho to the point of attachment is substituted.

In certain preferred compounds or salts of Formula I, or a subformula thereof, $R_2$ is hydrogen, methyl, or ethyl.

Yet other preferred compounds of Formula I or subformula thereof include those compounds in which $R_4$ and $R_5$ are independently selected from hydrogen, halogen, hydroxy, amino, cyano, $C_1$-$C_6$alkyl, halo($C_1$-$C_4$)alkyl, $C_1$-$C_6$alkoxy, ($C_2$-$C_6$)alkoxyalkyl mono and di($C_1$-$C_6$)alkylamino, phenyl, 5 to 6 membered heterocycloalkyl and 5 to 6 member heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$)alkylamino, —$XR_C$, and Y. In certain other preferred compounds of Formula I or subformula thereof, $R_4$ and $R_5$ are independently selected from hydrogen, halogen, hydroxy, amino, cyano, $C_1$-$C_6$alkyl, $C_1$-$C_6$alkoxy, mono- and di-($C_1$-$C_6$alkyl)amino.

Yet other preferred compounds of Formula I, including compounds of Formula III and V, include those compounds in which $Z_1$ is $NR_1''$, wherein $R_1''$ is selected from $C_3$-$C_{10}$alkyl, $C_5$-$C_7$cycloalkyl, (benzo)$C_5$-$C_7$cycloalkyl, ($C_5$-$C_7$cycloalkyl)methyl, each of which is substituted with between 0 and 2 substituents selected from halogen, $C_1$-$C_2$alkyl, halo$C_1$-$C_2$alkyl, $C_1$-$C_2$ alkoxy, and mono- and di-($C_1$-$C_2$alkyl)amino;

$Z_3$ is $CR_3$, wherein $R_3$ is selected from phenyl substituted with 0-2 independently selected $R_B$ groups, five to seven membered heterocycloalkyl substituted with 0-2 independently selected $R_A$, —$(CH_2)_pC(O)R_A$, and —$(CH_2)_pS(O)_2R_C$; and p is 0, 1, 2, or 3.

Certain other preferred compounds of Formula I and Formula II or a subformula thereof, e.g., compounds or salts of Formula III-VI, include those compounds in which $R_1$ and $R_1''$ are selected from (aryl)$C_0$-$C_4$alkyl and (heteroaryl)$C_0$-$C_4$alkyl, each of which is optionally substituted. Thus, certain preferred compounds of Formula I and Formula II include those compounds in which $R_1$ and $R_1''$ are selected from (aryl)$C_0$-$C_4$alkyl and (heteroaryl)$C_0$-$C_4$alkyl, each of which is substituted with 0 or more substituents (or more preferably between 0 and 5 substituents) independently chosen from halogen, hydroxy, amino, oxo, cyano, $C_1$-$C_6$alkyl, $C_1$-$C_6$alkoxy, phenoxy, benzyloxy, $C_1$-$C_6$hydroxyalkyl, $C_2$-$C_6$alkoxyalkyl, $C_1$-$C_6$haloalkoxy, $C_3$-$C_7$cycloalkyl, three to seven membered heterocycloalkyl, $C_5$-$C_7$heteroaryl, phenyl, mono- and di-($C_1$-$C_6$)alkylamino, mono- and di-($C_1$-$C_6$)alkylamino($C_1$-$C_6$)alkoxy, —(C($R_x$)$_2$)$_p$C(O)$R_A$, and —(C($R_x$)$_2$)$_p$S(O)$_2R_C$ and —$XR_C$.

In certain aspects, the invention provides compounds of Formula I or Formula II, or a subformula thereof, in which $R_1$ and $R_1"$ are selected from phenyl, 1-naphthyl, 2-naphthyl, pyridinyl, pyrazinyl, pyrimidinyl, benzyl, pyridinyl-methyl, pyrazinyl-methyl, and pyrimidinyl-methyl, each of which is substituted with between 0 and 2 substituents independently selected from halogen, hydroxy, amino, oxo, cyano, $C_1$-$C_3$alkyl, $C_1$-$C_3$alkoxy, $C_1$-$C_3$hydroxyalkyl, $C_2$-$C_4$alkoxyalkyl, $C_1$-$C_2$haloalkoxy, $C_5$-$C_6$heteroaryl, mono- and di-($C_1$-$C_2$)alkylamino, COOH, COO($C_1$-$C_4$alkyl), CONH($C_1$-$C_4$alkyl), and CON($C_1$-$C_4$alkyl)$_2$.

In yet other aspects, the invention provides compounds of Formula I or Formula II, or a subformula thereof, in which Ar is selected from the group consisting of Ar is selected from the group consisting of phenyl, pyridyl and pyrimidinyl each of which is mono- di- or trisubstituted with substituents independently chosen from halogen, cyano, nitro, halo($C_1$-$C_6$)alkyl, halo($C_1$-$C_6$)alkoxy, hydroxy, amino, $C_1$-$C_6$alkyl, $C_2$-$C_6$alkenyl, $C_2$-$C_6$alkynyl, $C_3$-$C_7$cycloalkyl, ($C_3$-$C_7$cycloalkyl)$C_1$-$C_4$alkyl, $C_1$-$C_6$alkoxy, mono- and di($C_1$-$C_6$alkyl)amino, amino($C_1$-$C_6$)alkyl, and mono- and di($C_1$-$C_6$alkyl)amino, wherein, in Ar, at least one of the positions ortho to the point of attachment is substituted.

In certain preferred compounds of the invention according to Formula I or Formula II, or a subformula thereof, $R_2$ is hydrogen, methyl, or ethyl.

In yet other aspects, the invention provides compounds of Formula I or Formula II, or subformula thereof, in which $R_4$ and $R_5$ are independently selected from hydrogen, halogen, hydroxy, amino, cyano, $C_1$-$C_6$alkyl, halo($C_1$-$C_4$)alkyl, $C_1$-$C_6$alkoxy, ($C_2$-$C_6$)alkoxyalkyl mono and di($C_1$-$C_6$)alkylamino, phenyl, 5 to 6 membered heterocycloalkyl and 5 to 6 member heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$)alkylamino, —$XR_C$, and Y. In certain other preferred compounds, $R_4$ and $R_5$ are independently selected from hydrogen, halogen, hydroxy, amino, cyano, $C_1$-$C_6$alkyl, $C_1$-$C_6$alkoxy, mono- and di-($C_1$-$C_6$alkyl)amino.

In yet another aspect, the invention provides compounds or salts of Formula II, or a subformula thereof (e.g., compounds or salts of Formula III-VI), in which:

$R_1$ or $R_1"$ is phenyl, 1-naphthyl, 2-naphthyl, pyridyl, pyrimidinyl, pyrazinyl, pyridazinyl, each of which is optionally substituted; or $R_1$ or $R_1"$ is a group of the formula:

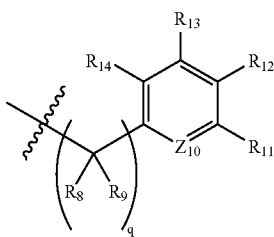

wherein q is 1, 2, or 3;

$R_8$ and $R_9$ are independently chosen at each occurrence from hydrogen or $C_1$-$C_4$alkyl, or $CR_8R_9$ taken in combination form a keto group;

$Z_{10}$ is nitrogen or $CR_{10}$;

$R_{10}$, $R_{11}$, $R_{12}$, $R_{13}$, and $R_{14}$ are independently selected from the group consisting of hydrogen, halogen, hydroxy, amino, cyano, —COOH, —C(O)NH$_2$, $C_1$-$C_6$alkyl, $C_1$-$C_6$alkoxy, halo$C_1$-$C_6$ alkyl, halo$C_1$-$C_6$alkoxy, $C_3$-$C_7$cycloalkyl, hydroxy$C_1$-$C_6$alkyl, amino$C_1$-$C_6$alkyl. Such compounds of Formula II are referred to herein as compounds of Formula VII.

In certain other aspects, the invention provides compounds of Formula II, and more preferably of Formula VII, in which $R_2$ is selected from hydrogen, $C_1$-$C_6$alkyl;

$R_3$ is hydrogen, halogen, hydroxy, amino, $C_1$-$C_6$alkyl, $C_1$-$C_6$alkoxy, halo$C_1$-$C_6$alkyl, halo$C_1$-$C_6$alkoxy, phenyl substituted with 0-2 independently selected $R_B$ groups; five to seven membered heterocycloalkyl substituted with 0-2 independently selected $R_A$;

—(CH$_2$)$_p$C(O)$R_A$, and —(CH$_2$)$_p$S(O)$_2R_C$;

$R_5$ is selected from hydrogen, halogen, cyano, amino, $C_1$-$C_6$alkyl, $C_1$-$C_6$alkoxy, $C_3$-$C_7$ cycloalkyl, ($C_3$-$C_7$cycloalkyl)$C_1$-$C_4$alkyl, ($C_3$-$C_7$cycloalkyl)$C_1$-$C_4$alkoxy, mono and di($C_1$-$C_6$alkyl)amino, amino($C_1$-$C_6$)alkyl, mono and di($C_1$-$C_6$alkyl)amino($C_1$-$C_6$)alkyl, halo($C_1$-$C_6$) alkyl, and halo($C_1$-$C_6$)alkoxy; and Ar is selected from the group consisting of phenyl, pyridyl and pyrimidinyl each of which is mono- di- or trisubstituted with substituents independently chosen from halogen, cyano, nitro, halo($C_1$-$C_6$)alkyl, halo($C_1$-$C_6$)alkoxy, hydroxy, amino, $C_1$-$C_6$alkyl, $C_2$-$C_6$alkenyl, $C_2$-$C_6$alkynyl, $C_3$-$C_7$cycloalkyl, ($C_3$-$C_7$cycloalkyl)$C_1$-$C_4$alkyl, $C_1$-$C_6$alkoxy, mono- and di($C_1$-$C_6$alkyl)amino, amino($C_1$-$C_6$)alkyl, and mono- and di($C_1$-$C_6$alkyl)amino, wherein, in Ar, at least one of the positions ortho to the point of attachment is substituted.

In yet other aspects, the invention provides compounds or salts of Formula II, or a subformula thereof in which:

$R_1"$ is selected from mono-, di-, or tri-substituted phenyl, or 1-naphthyl, 2-naphthyl, pyridyl, pyrimidinyl, pyrazinyl, and pyridazinyl, each of which is optionally mono-, di-, or tri-substituted, or $R_1"$ is a group selected from:

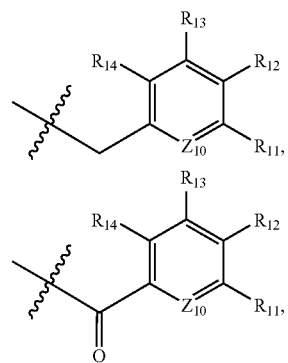

-continued

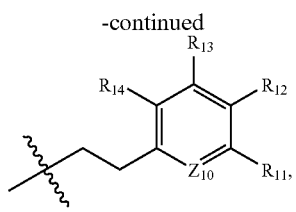

wherein $Z_{10}$ is N or $CR_{10}$;

$R_8$ and $R_9$ are independently chosen at each occurrence from hydrogen or $C_1$-$C_4$alkyl, or $CR_8R_9$ taken in combination form a keto group;

$R_{10}$, $R_{11}$, $R_{12}$, $R_{13}$, and $R_{14}$ are independently selected from the group consisting of hydrogen, halogen, hydroxy, amino, cyano, —COOH, —C(O)NH$_2$, $C_1$-$C_6$alkyl, $C_1$-$C_6$alkoxy, $C_2$-$C_6$alkenyl, $C_2$-$C_6$alkynyl, hydroxy$C_1$-$C_6$alkyl, amino$C_1$-$C_6$alkyl.

In yet other aspects, the invention provides compounds or salts of Formula II, or a subformula thereof in which:

$R_3$ is hydrogen, halogen, hydroxy, amino, $C_1$-$C_6$alkyl, $C_1$-$C_6$alkoxy, halo$C_1$-$C_6$alkyl, halo$C_1$-$C_6$alkoxy, $C_3$-$C_7$cycloalkyl, phenyl substituted with 0-2 independently selected $R_B$ groups; five to seven membered heterocycloalkyl substituted with 0-2 independently selected $R_4$; —(CH$_2$)$_p$(CH(OH))$R_D$, —(CH$_2$)$_p$C(O)$R_A$, and —(CH$_2$)$_p$S(O)$_2$$R_C$; or $R_3$" is hydrogen, $C_1$-$C_6$alkyl, halo$C_1$-$C_6$alkyl, $C_3$-$C_7$cycloalkyl, phenyl substituted with 0-2 independently selected $R_B$ groups; five to seven membered heterocycloalkyl substituted with 0-2 independently selected $R_4$; —(CH$_2$)$_p$(CH(OH))$R_D$, —(CH$_2$)$_p$C(O)$R_A$, and —(CH$_2$)$_p$S(O)$_2$$R_C$; and p is 0, 1, 2, or 3.

In still other preferred compounds of Formula II, or a subformula thereof, $R_3$ or $R_3$" is hydrogen, $C_1$-$C_6$alkyl, $C_1$-$C_6$alkoxy, $C_3$-$C_7$cycloalkyl, —(CH$_2$)$_p$(CH(OH))$R_D$, —(CH$_2$)$_p$C(O)$R_A$, and —(CH$_2$)$_p$S(O)$_2$$R_C$; and p is 0, 1, or 2.

Certain compounds according to the Formulas provided herein, which have two or more stereogenic centers, have a diastereomeric excess of at least 50%. For example, such compounds may have a diastereomeric excess of at least 60%, 70%, 80%, 85%, 90%, 95%, or 98%. Certain such compounds have a diastereomeric excess of at least 99%.

Certain compounds according to the Formulas provided herein, which have one or more stereogenic center, have an enantiomeric excess of at least 50%. For example, such compounds may have an enantiomeric excess of at least 60%, 70%, 80%, 85%, 90%, 95%, or 98%. Certain such compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

Pyrrolo-pyridine, pyrrolo-pyrimidine and related heterocyclic compounds and pharmaceutically acceptable forms thereof provided herein detectably alter (modulate) C5a receptor activity and/or ligand binding, as determined using a standard in vitro $C_5$ receptor-mediated chemotaxis assay (described in Example 27), radioligand binding (described in Example 32), or C5a receptor-mediated calcium mobilization assay (described in Example 34). Preferred compounds exhibit an EC$_{50}$ of about 500 mM or less in such a standard C5a receptor-mediated chemotaxis, radioligand binding, and/or calcium mobilization assay, more preferably an EC$_{50}$ of about 250 nM or less in such an assay, still more preferably an EC$_{50}$ of about 200, 150, 100, 50, 25, 10, or 5 nM or less in such an assay.

Initial characterization of compounds can be conveniently carried out using a C5a receptor binding assay or functional assay, such as set forth in the Examples, and may be expedited by applying such assays in a high throughput screening setting. Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6-9, columns 19-23, as well as for its discussion of complement and inflammation at columns 1-2. Those of skill in the art will recognize that such assays can be readily adapted to the use of cells or animals of different species as deemed appropriate.

In certain embodiments, preferred compounds have favorable pharmacological properties, including oral bioavailability (such that a sub-lethal or preferably a pharmaceutically acceptable oral dose, preferably less than 2 grams, more preferably of less than or equal to one gram, can provide a detectable in vivo effect such as a reduction of C5a-induced neutropenia), ability to inhibit leukocyte chemotaxis at nanomolar concentrations and preferably at sub-nanomolar concentrations, low toxicity (a preferred compound is nontoxic when a C5a receptor-modulatory amount is administered to a subject), minimal side effects (a preferred compound produces side effects comparable to placebo when a C5a receptor-modulatory amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred).

Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography B* 677:1-27. Compound half-life is inversely proportional to the frequency of dosage of a compound required to achieve an C5a receptor modulatory amount. In vitro half-lives of compounds may be predicted from assays of microsomal half-life as described by Kuhnz and Gieschen (1998) *Drug Metabolism and Disposition* 26:1120-27.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, and (4) does not cause substantial release of liver enzymes.

As used herein, a compound that "does not substantially inhibit cellular ATP production" is a compound that satisfies the criteria set forth in Example 36, herein. In other words, cells treated as described in Example 36 with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that "does not significantly prolong heart QT intervals" is a compound that does not result in a statistically significant prolongation of heart QT intervals (as determined by electrocardiography) in guinea pigs, minipigs or dogs upon administration of twice the minimum dose yielding a therapeutically effective in vivo concentration. In certain preferred embodiments, a dose of 0.01, 0.05. 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound "does not cause substantial liver enlargement" if daily treatment of laboratory rodents (e.g., mice or rats) for 5-10 days with twice the minimum dose that yields a therapeutically effective in vivo concentration results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound "does not promote substantial release of liver enzymes" if administration of twice the minimum dose yielding a therapeutically effective in vivo concentration does not elevate serum levels of ALT, LDH or AST in laboratory rodents by more than 100% over matched mock-treated controls. In more highly preferred embodiments, such doses do not elevate such serum levels by more than 75% or 50% over matched controls. Alternately, a compound "does not promote substantial release of liver enzymes" if, in an in vitro hepatocyte assay, concentrations (in culture media or other such solutions that are contacted and incubated with hepatocytes in vitro) equivalent to two-fold the minimum in vivo therapeutic concentration of the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the minimum in vivo therapeutic concentration of the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the minimum therapeutically effective in vivo concentration.

Certain preferred compounds are not clastogenic or mutagenic (e.g., as determined using standard assays such as the Chinese hamster ovary cell vitro micronucleus assay, the mouse lymphoma assay, the human lymphocyte chromosomal aberration assay, the rodent bone marrow micronucleus assay, the Ames test or the like) at a concentration equal to the minimum therapeutically effective in vivo concentration. In other embodiments, certain preferred compounds do not induce sister chromatid exchange (e.g., in Chinese hamster ovary cells) at such concentrations.

In certain embodiments, preferred compounds exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 4 micromolar. Also provided herein are highly specific C5a receptor modulatory compounds that exhibit 200-fold greater affinity for the C5a receptor that for other cellular receptors. Such receptors include neurotransmitter receptors such as alpha- or beta-adrenergic receptors, muscarinic receptors (particularly m1, m2 or m3 receptors), dopamine receptors, and metabotropic glutamate receptors; as well as histamine receptors and cytokine receptors (e.g., interleukin receptors, particularly IL-8 receptors). Such receptors may also include $GABA_A$ receptors, bioactive peptide receptors (other than C5a receptors and C3a receptors, including NPY or VIP receptors), neurokinin receptors, bradykinin receptors, and hormone receptors (e.g., CRF receptors, thyrotropin releasing hormone receptors or melanin-concentrating hormone receptors). Compounds that act with high specificity generally exhibit fewer undesirable side effects.

Within certain embodiments, modulators provided herein do not bind detectably to receptors that do not mediate inflammatory responses, such as GABA receptors, MCH receptors, NPY receptors, dopamine receptors, serotonin receptors and VR1 receptors, with high or even moderate affinity. In addition, or alternatively, certain preferred C5a receptor modulators exhibit an affinity for C5a receptor that is substantially higher than for receptors that do not mediate inflammatory responses (e.g., at least five times higher, at least ten times higher or at least 100 times higher). Assays for evaluating binding to receptors that do not mediate inflammatory responses include, for example, those described in U.S. Pat. No. 6,310,212, which is incorporated herein by reference for its disclosure of a $GABA_A$ receptor binding assays in Examples 14, columns 16-17, in U.S. patent application Ser. No. 10/152,189 which is incorporated herein by reference for its disclosure of an MCH receptor binding assay in Example 2, pages 104-105, in U.S. Pat. No. 6,362,186, which is incorporated herein by reference for its disclosure of $CRF_1$ and NPY receptor binding assays in Examples 19, columns 45-46, in U.S. Pat. No. 6,355,644, which is incorporated herein by reference for its disclosure of a dopamine receptor binding assay at column 10, and in U.S. Pat. No. 6,482,611, which is incorporated herein by reference for its disclosure of VR1 receptor binding assays in Examples 4-5, column 14. It will be apparent that the C5a receptor modulators provided herein may, but need not, bind to one or more other receptors known to mediate inflammatory responses, such as C3a receptors and/or $A_3$ receptors.

Certain preferred compounds are C5a receptor antagonists that do not possess significant (e.g., greater than 5%) agonist activity in any of the C5a receptor-mediated functional assays discussed herein. Specifically, this undesired agonist activity can be evaluated, for example, in the GTP binding assay of Example 33, by measuring small molecule mediated GTP binding in the absence of the natural agonist, C5a. Similarly, in a calcium mobilization assay (e.g., that of Example 34) a small molecule compound can be directly assayed for the ability of the compound to stimulate calcium levels in the absence of the natural agonist, C5a. The preferred extent of C5a agonist activity exhibited by compounds provided herein is less than 10%, 5% or 2% of the response elicited by the natural agonist, C5a.

Also preferred, in certain embodiments, are C5a receptor modulators that inhibit the occurrence of C5a-induced oxidative burst (OB) in inflammatory cells (e.g., neutrophil) as can be conveniently determined using an in vitro neutrophil OB assay.

For detection purposes, compounds provided herein may be isotopically-labeled or radiolabeled. Accordingly, compounds recited in Formula I (or any other formula specifically recited herein) may have one or more atoms replaced by an atom of the same element having an atomic mass or mass number different from the atomic mass or mass number usually found in nature. Examples of isotopes that can be present in compounds provided herein include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^{2}H$) can afford certain therapeutic advantages resulting from greater metabolic stability, for example increased in vivo half-life or reduced dosage requirements and, hence, may be preferred in some circumstances.

Pharmaceutical Compositions

The present invention also provides pharmaceutical compositions comprising one or more C5a receptor modulators provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mammose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions (e.g., in the treatment of skin conditions such as burns or itch).

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monooleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids and emulsions. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

C5a modulators described herein may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally administered in a therapeutically effective amount. Preferred systemic doses range from about 0.1 mg to about 140 mg per kilogram of body weight per day (about 0.5 mg to about 7 g per patient per day), with oral doses generally being about 5-20 fold higher than intravenous doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Packaged pharmaceutical compositions are also provided herein, comprising a C5a receptor modulatory amount of at least one C5a receptor antagonist in a container (preferably sealed) and instructions for using the C5a receptor antagonist to treat a condition responsive to C5a receptor modulation (e.g., rheumatoid arthritis, psoriasis, cardiovascular disease, reperfusion injury, bronchial asthma, chronic pulmonary obstructive disorder (COPD), cystic fibrosis, Alzheimer's disease, stroke, myocardial infarction, atherosclerosis, ischemic heart disease or ischemia-reperfusion injury). The active agent(s) may be formulated for administration in a single pharmaceutical preparation (e.g., within the same pharmaceutical composition). Alternatively, each of the active agents may be formulated for separate administration, by the same or different routes of administration. Within a packaged pharmaceutical preparation, a C5a receptor modulatory amount may be packaged as a single dose unit; alternatively, multiple doses may be packaged together for convenience. The C5a receptor modulator may be presented in any suitable container including, but not limited to, a plastic, paper, metal or glass package such as an ampoule, bottle, vial, blister package, infusion bag, syringe, inhaler or tube. For example, a packaged pharmaceutical preparation for oral administration of an active agent may comprise a blister package containing rows of tablets. Instructions may be present on a label attached to the container or on exterior packaging, or may be provided as a package insert.

Methods of Use

C5a modulators provided herein may be used as agonists or (preferably) antagonists, such as inverse agonists, of C5a receptors in a variety of contexts, both in vitro and in vivo. Within certain aspects, C5a antagonists may be used to inhibit the binding of C5a receptor ligand (e.g., C5a) to C5a receptor in vitro or in vivo. In general, such methods comprise the step of contacting a C5a receptor with a sufficient concentration of one or more C5a receptor modulators as provided herein, in the presence of C5a receptor ligand in aqueous solution and under conditions otherwise suitable for binding of the ligand to C5a receptor. The C5a receptor may be present in suspension (e.g., in an isolated membrane or cell preparation), or in a cultured or isolated cell. Within certain embodiments, the C5a receptor is expressed by a cell present in a patient, and the aqueous solution is a body fluid. In general, the concentration of C5a receptor modulator contacted with the receptor should be sufficient to inhibit C5a binding to C5a receptor in vitro as measured, for example, using a calcium mobilization assay or chemotaxis assay as described herein.

Also provided herein are methods for modulating, preferably inhibiting, the signal-transducing activity of a C5a receptor. Such modulation may be achieved by contacting a C5a receptor (either in vitro or in vivo) with a C5a receptor modulatory amount of one or more C5a receptor modulators provided herein under conditions suitable for binding of the modulator(s) to the receptor. The receptor may be present in solution or suspension, in a cultured or isolated cell preparation or within a patient. Modulation of signal transducing activity may be assessed by detecting an effect on calcium ion conductance (also referred to as calcium mobilization or flux) or by detecting an effect on C5a receptor-mediated cellular chemotaxis. C5a receptor modulator(s) provided herein are preferably administered to a patient (e.g., a human) orally or topically, and are present within at least one body fluid of the animal while modulating C5a receptor signal-transducing activity.

The present invention further provides methods for treating patients suffering from conditions responsive to C5a receptor modulation. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to C5a receptor modulation" if modulation of C5a receptor activity results in alleviation of the condition or a symptom thereof. Patients may include primates (especially humans), domesticated companion animals (such as dogs, cats, horses) and livestock (such as cattle, pigs, sheep), with dosages as described herein.

Conditions that are responsive to C5a receptor modulation include the following:

Autoimmune disorders—e.g., rheumatoid arthritis, systemic lupus erythematosus (and associated glomerulonephritis), psoriasis, Crohn's disease, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, and hyperacute rejection of transplanted organs.

For asthma therapy, C5a receptor antagonists provided herein may be used to prevent or decrease the severity of both acute early phase asthma attack and the late phase reactions that follow such an asthma attack.

Inflammation, Inflammatory disorders and related conditions—e.g., neutropenia, sepsis, septic shock, Alzheimer's disease, stroke, inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), cystic fibrosis, neonatal-onset multisystem inflammatory disease (NOMID), Muckle-Wells syndrome, lichen planus, familial cold autoinflammatory syndrome (FCAS), inflammatory bowel disease (IBD), colitis, cystic fibrosis, ruptured abdominal aortic aneurysm and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Cardiovascular and Cerebrovascular Disorders—e.g. myocardial infarction, coronary thrombosis, vascular occlusion, post-surgical vascular reocclusion, atherosclerosis, traumatic central nervous system injury, and ischemic heart disease. For example, a therapeutically effective amount of a compound provided herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Ocular Disorders—e.g., vascular retinopathies, ocular inflammation, age-related macular degeneration, proliferative vitreoretinopathy, Behcet's disease, vernal keratoconjunctivitis, retinal capillary infarction, retinal hemorrhage, prevention of ocular complications during IFN-a therapy, and uveitis.

Vasculitis—e.g., immunovasculitis, microscopic polyangiitis, Churg-Strauss syndrome, Kawasaki syndrome, Wegener's granulomatosis and urticarial vasculitis.

HIV infection and AIDS—C5a receptor modulators provided herein may be used to inhibit HIV infection, delay AIDS progression or decrease the severity of symptoms of HIV infection and AIDS.

In a further aspect, C5a receptor modulators may be used to perfuse a donor organ prior to transplantation of the organ into a recipient patient. Such perfusion is preferably carried out using a solution (e.g., pharmaceutical composition) comprising a concentration of the modulator that is sufficient to inhibit C5a receptor-mediated effects in vitro and/or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Within further aspects, C5a antagonists provided herein may be used to treat Alzheimer's disease, multiple sclerosis, and cognitive function decline associated with cardiopulmonary bypass surgery and related procedures. Such methods comprise administration of a therapeutically effective amount of a C5a antagonist provided herein to a patient afflicted with one or more of the above conditions, or who is considered to be at risk for the development of one or more such conditions.

In a further aspect, C5a receptor modulators of the current invention may be used in the treatment of disorders associated with pregnancy including antiphospholipid syndrome.

Within further aspects, C5a antagonists provided herein may be used to treat Alzheimer's disease, multiple sclerosis, and cognitive function decline associated with cardiopulmonary bypass surgery and related procedures. Such methods comprise administration of a therapeutically effective amount of a C5a antagonist provided herein to a patient afflicted with one or more of the above conditions, or who is considered to be at risk for the development of one or more such conditions.

Suitable patients include those patients suffering from or susceptible to a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient a C5a receptor modulatory amount of one or more compounds or forms thereof provided herein. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

As noted above, certain compounds and compositions provided herein are useful as inhibitors of C5a receptor-mediated chemotaxis (e.g., they may be used as standards in assays of such chemotaxis). Accordingly, methods are provided herein for inhibiting C5a receptor-mediated cellular chemotaxis, preferably leukocyte (e.g., neutrophil) chemotaxis. Such methods comprise contacting white blood cells (particularly primate white blood cells, especially human white blood cells) with one or more compounds provided herein. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound as described herein has been added.

Dosage levels of the order of from about 0.1 mg to about 140 mg per kilogram of body weight per day are useful in the treatment or prevention of conditions involving pathogenic C5a activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient C5a receptor modulator to achieve a serum concentration of 20 ng-1 µg/mL serum should be administered, most preferably sufficient C5a receptor modulator to achieve a serum concentration of 50 ng/mL-200 ng/mL serum should be administered. For direct injection into the synovium (for the treatment of arthritis) sufficient C5a receptor modulator should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Within separate aspects, the present invention provides a variety of non-pharmaceutical in vitro and in vivo uses for the compounds provided herein. For example, such compounds may be labeled and used as probes for the detection and localization of C5a receptor (in samples such as cell preparations or tissue sections, preparations or fractions thereof). Compounds may also be used as positive controls in assays for C5a receptor activity, as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

Preparation of Compounds

Representative methods for preparing compounds of Formula I and Formula II are shown in Schemes 1-10. Those skilled in the art will recognize that the reagents and synthetic transformations in the following Schemes can be readily modified to produce additional compounds of Formula I and Formula II. When a protecting group is required, an optional deprotection step may be employed. Suitable protecting groups and methodology for protection and deprotection such as those described in *Protecting Groups in Organic Synthesis* by T. Greene are well known. Compounds and intermediates requiring protection/deprotection will be readily apparent.

Abbreviations used in the following Schemes and Examples are as follows:

Ac$_2$O acetic anhydride
BOP benzotriazol-1-yloxy-tris(dimethylamino)-phosphonium hexafluorophospate
n-BuLi n-butyl lithium
CDCl$_3$ deuterated chloroform
DCE 1,2-dichlorethane
DCM dichloromethane
DEAD diethyl azidocarboxylate
DIBAL diisobutylaluminum hydride
DIEA diiosopropylethylamine
DMA N,N-dimethylacetamide
DMAP 4-N,N-dimethylaminopyridine
DMF N,N-dimethylformamide
DPPF 1,1'-bis(diphenylphosphino)ferrocene
EtOAc ethyl acetate
EtOH ethanol
HOAc acetic acid
HPLC high pressure liquid chromatography
$^1$H NMR proton nuclear magnetic resonance
Hz hertz
LAH lithium aluminum hydride
LDA lithium diisopropylamide
LC/MS liquid chromatography/mass spectrometry
MEK methyl ethyl ketone (2-butanone)
MeOH methanol
MHz megahertz
MS mass spectrometry
(M+1) mass+1
NMP N-methyl-2-pyrrolidone
NBS N-bromosuccinimde
δ chemical shift
Pd(PPh$_3$)$_4$ tetrakis(triphenylphosphine) palladium (0)
POCl$_3$ phosphorous oxychloride
PrMgCl n-propylmagnesium chloride
PTLC preparative thin layer chromatography
TFA trifluoroacetic acid
THF tetrahydrofuran
TMSCN trimethylsilylcyanide
18-C-6 18-crown-6
Bredereck's reagent tert-butoxybis(dimethylamino)methane Scheme 1. Preparation of Intermediate for synthesis of compounds of Formula Ia.

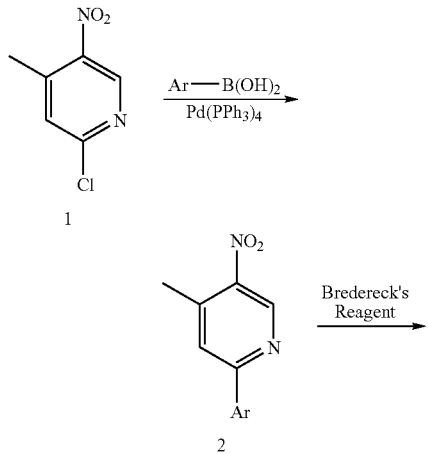

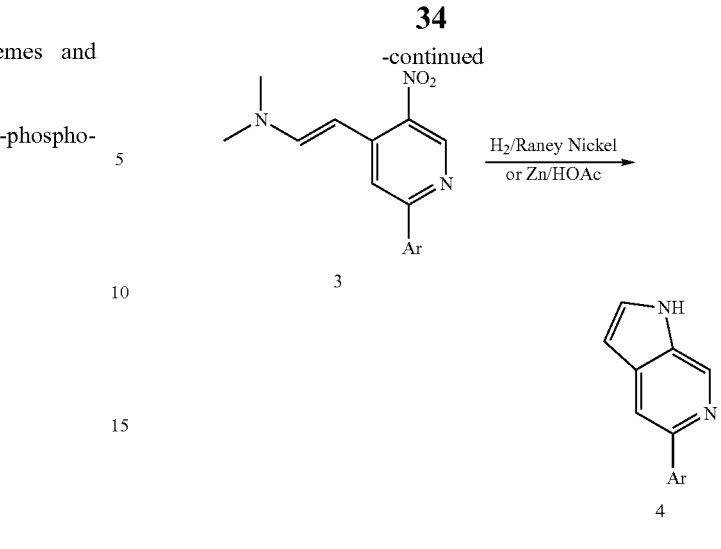

Scheme 1 illustrates the preparation of intermediate 4. In Step 1, Palladium catalyzed Suzuki coupling of 2-chloro-4-methyl-5-nitro-pyridine 1 with appropriate aryl and heteroarylboronic acids provides 2-aryl-4-methyl-5-nitro-pyridine 2. In Step 2, reaction of 2-aryl-4-methyl-5-nitro-pyridine 2 with excess of Bredereck's reagent without a solvent or with a solvent, such as DMF, followed by reduction/cyclization provides the corresponding 5-aryl-1H-pyrrolo[2,3-c]pyridine 4. In Step 3, reduction conditions include but are not limited to Raney Nickel catalyzed hydrogenation or reduction with Zn powder in acetic acid. It will be readily appreciated by those skilled in the art that a broad spectrum of additional reaction conditions and reactants can be used in Scheme 1 to expand the scope of compounds produced. In some instances, the order of synthetic steps employed may be changed. Further, suitable protecting group strategies can be incorporated to facilitate the synthesis of certain additional compounds of Formula I or Formula II.

Scheme 2. Preparation of compounds of Formula Ia wherein R$_1$″ is attached to intermediate 4.

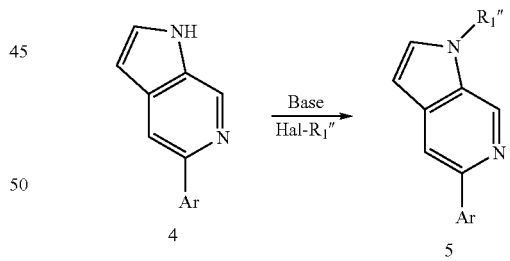

Scheme 2 illustrates a general method for preparing compounds of Formula Ia wherein R$_1$″ is attached to intermediate 4. Wherein R$_1$″ is alkyl, benzyl, or heteroarylmethyl, compound 5 of Formula I or Formula II can be obtained by reaction of intermediate 4 with haloalkyl, haloalkyl-aryl or haloalkyl-heteroaryl compounds in presence of a base such as but not limited to potassium carbonate or cesium carbonate in an aprotic solvent DMF, acetonitrile or the like at the temperatures ranging from 0° C. to reflux. Wherein R$_1$″ is benzoyl or pyridinoyl, compound 5 of Formula I or Formula II can be obtained by reaction of intermediate 4 with the appropriate acid chloride in presence of a base, such as but not limited to cesium carbonate in an aprotic solvent DMF, acetonitrile or the like at the temperatures ranging from 0° C. to reflux. Alternatively, the pre-formed sodium or potassium salt of 4 (formed by reaction of 4 with sodium or potassium hydride or other suitable bases) can be reacted with haloakyl-aryl, haloalkyl-heteroarl, benzoyl or pyridinoyl derivatives in an aprotic solvent such as DMF, acetonitrile or the like at temperatures ranging from 0° C. to reflux to give 5. Wherein $R_1''$ is aryl or heteroaryl, a preferred synthetic method comprises combination of an appropriate iodoaryl/heteroaryl or bromoaryl/heteroaryl with intermediate 4 in presence of two equivalents of each or excess of copper (I) iodide, cesium carbonate and ethylenediamine in a solvent such as dioxane or the like at elevated temperatures ranging from 40° C. to reflux to afford compound 5. Alternatively, wherein $R_1''$ is heteroaryl, the appropriate fluoroheteroaryl or chloroheteroaryl is used to react intermediate 4 in presence of a base such as cesium carbonate or the like, in a solvent such as DMF or the like at elevated temperature ranging from 40° C. to reflux to afford compound 5. It is readily apparent that the intermediate 4, may be utilized in a wide variety of additional coupling strategies to produce further examples wherein a bond to $R_1''$ is formed.

pyridine N-oxide 6 by the action of meta-chlorobenzoic acid. N-oxide 6 can be subsequently methylated and treated with potassium cyanide to provide compound 7 wherein $R_5$ is cyano or reacted with phosphorous oxychloride to provide compound 7 wherein $R_5$ is chloro. Compound 7 wherein $R_5$ is Cl can be further converted to the other groups as claimed in Formula I or Formula II via conventional methods, such as reactions with amines, alkoxides or boronic acids.

Scheme 4. Preparation of compounds of Formula I or Formula II where $R_3$ is introduced.

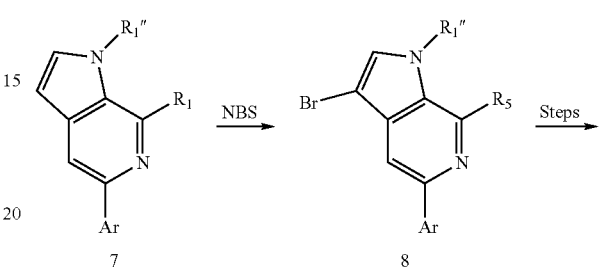

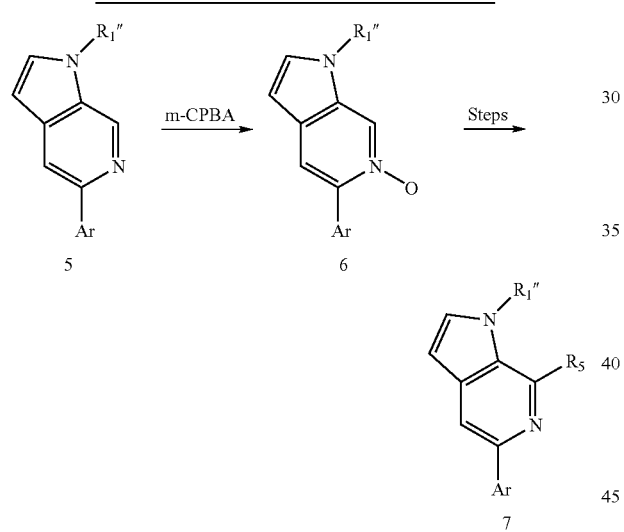

Scheme 3 provides a route for attaching $R_5$ to compound 5. In step 1, compound 5 is converted to the corresponding Scheme 4 illustrates a route for preparing compounds of Formula I or Formula II wherein $R_3$ is introduced via bromo intermediate 8. In step 1, compound 7 is converted to the corresponding bromide 8 by the treatment with a brominating agent, such as N-bromosuccinimde. Bromide 8 serves as a versatile intermediate for a variety of organic transformations to provide compound 9 of Formula I or Formula II. Such organic transformations include Suzuki boronic acid coupling, Stille reaction, zinc mediate coupling or halogen-metal exchange reaction for addition of electrophiles such as ketones, aldehydes, etc. References describing the listed organic transformations can be found in "Comprehensive Organic Transformations", Richard C. Larock, Wiley-VCH., 1999.

Scheme 5. Preparation of compounds of Formula I or Formula II.

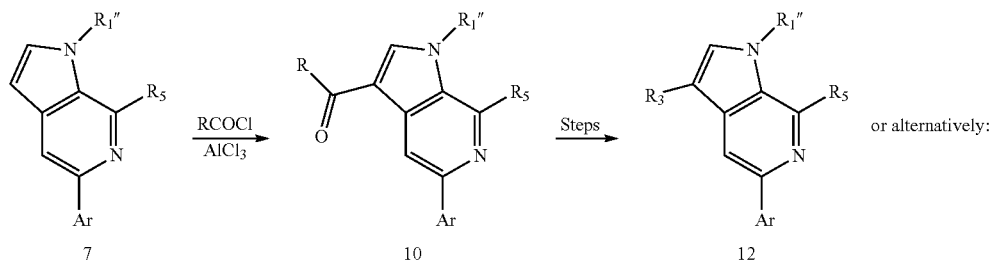

-continued

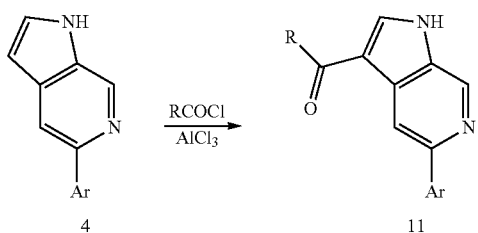

Scheme 5 shows additional routes for preparing compounds of Formula I or Formula II. Compound 7 can undergo Friedel-Crafts acylation to provide ketone compound 10 if the nature of $R_1''$ of Formula I or Formula II is chemically stable to standard Friedel-Crafts acylation conditions. Alternatively, intermediate 4 can be converted to ketone 11 by the same method, followed by the conversion according to the methods described in Scheme 2 and 3 to give compound 10. Ketone compound 10 can readily undergo single or multiple step organic transformations such as Wittig, Homer Emmons or Petersen reaction, Grignard addition or reduction to provide desired compound 12 of Formula I or Formula II. Some general reviews of such reactions are contained in "Organic Reactions" Dauben, W. G., Wiley, N.Y., 1977, 25, 73. McMurry, J. E. Acct. Chem. Res. 1983, 16, 405.

Scheme 6 Preparation of compounds of Formula I or Formula II.

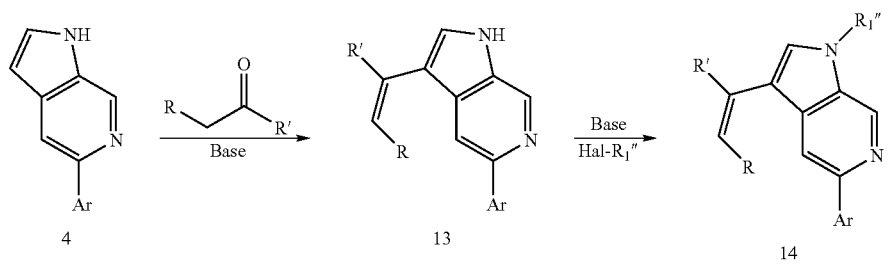

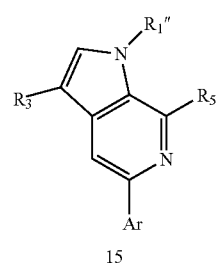

Scheme 6 illustrates another route to synthesize compounds of Formula I or Formula II. In Step 1, intermediate 4 can react with a variety of ketones in presence of a base, such as KOH or cessium carbonate, followed by in situ elimination or acid assisted elimination to give the corresponding olefin compound 13, to which group $R_1''$ can be introduced by methods described in Scheme 2 to give compound 14. Compound 14 can then readily undergo single or multiple step organic transformations such as reduction, oxidation, etc. to give compounds of Formula I or Formula II.

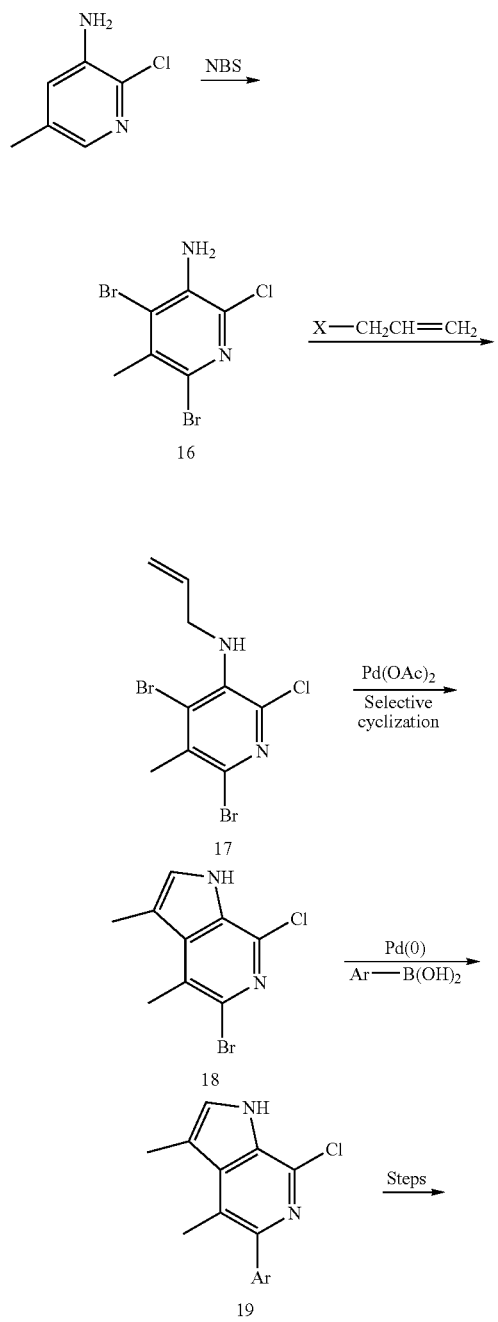

-continued

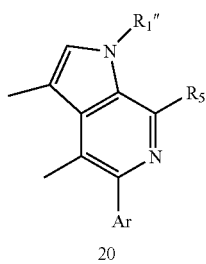

20

Scheme 7 illustrates a specific method to synthesize compounds of Formula I or Formula II wherein $R_3$ is methyl, $Z_4$ is $CR_4$, $R_4$ is methyl and $R_2$ is hydrogen. In Step 1, bromonation of 2-chloro-5-methyl-pyridin-3-ylamine with NBS provides dibromo compound 16, which can undergo alkylation to give allyl compound 17. Palladium catalyzed selective cyclization provides 5-bromo-7-chloro-3,4-dimethyl-1H-pyrrolo[2,3-c]pyridine 18, which can undergo similar reactions described in Scheme 1-3 to provide compound 20 of Formula I or Formula II.

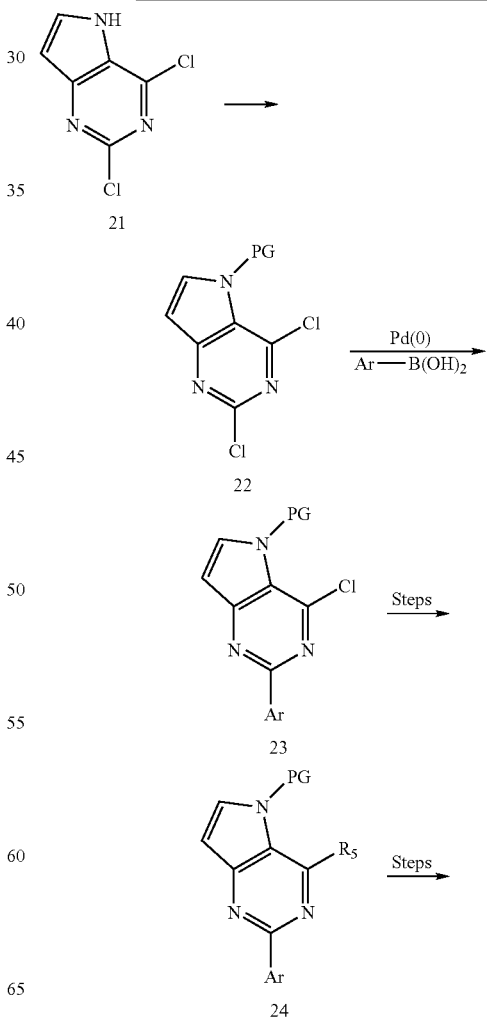

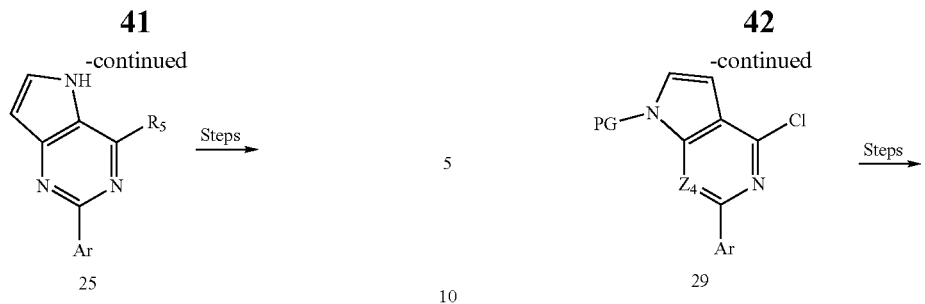

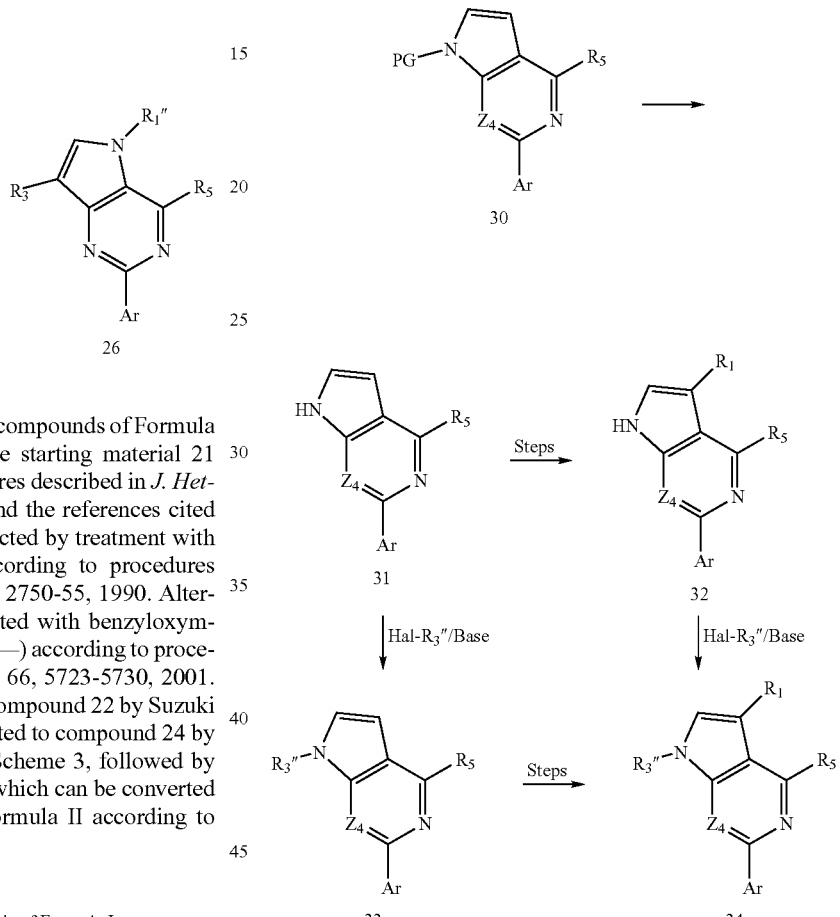

Scheme 8 shows the preparation of compounds of Formula I or Formula II wherein $Z_4$=N. The starting material 21 maybe prepared according to procedures described in *J. Heterocyclic Chem.*, 24, 821-27, 1987 and the references cited within. Compound 21 is benzyl protected by treatment with benzyl bromide (PG is benzyl) according to procedures described in J. Medicinal Chem., 33, 2750-55, 1990. Alternatively compound 21 can be protected with benzyloxymethyl chloride (PG is benzyl-O—$CH_2$—) according to procedures described in J. Organic Chem., 66, 5723-5730, 2001. Compound 23 can be obtained from compound 22 by Suzuki boronic acid coupling, then be converted to compound 24 by the similar procedures described in Scheme 3, followed by deprotection to give intermediate 25 which can be converted to compound 26 of Formula I or Formula II according to Scheme 2, 4, 5 or 6.

Scheme 9 Preparation of compounds of Formula I
or Formula II in which $Z_1$ is $CR_1$ and $Z_3$ is $NR_3''$.

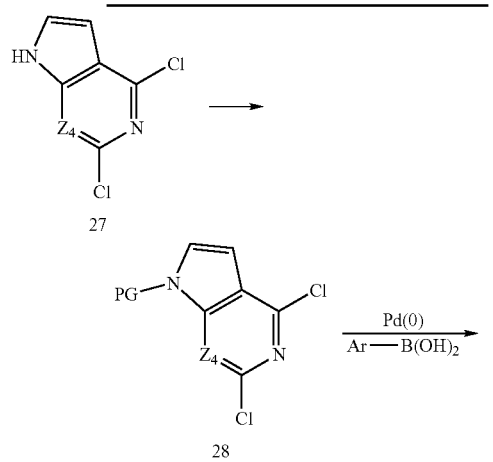

Scheme 9 illustrates general routes to preparing compounds of Formula I or Formula II in which $Z_1$ is $CR_1$ and $Z_3$ is $NR_3''$. The starting material 27 ($Z_4$=N or CH) is prepared according to procedures described in *J. Am. Chem. Soc.*, 106, 6379-6382, 1987 and the references cited within. Compound 29 is protected (PG is benzyl or benzyloxymethyl) according to procedures described in Scheme 8. Compound 28 is prepared from compound 29 by Suzuki boronic acid coupling, then converted to compound 30 by the similar procedures described in Scheme 3, followed by deprotection to give intermediate 31. Group $R_1$ of compound 32 or compound 34 of Formula I or Formula II can be introduced from compound 31 or 33 respectively in similar ways described for Group $R_1''$ in Schemes 4, 5 and 6. Group $R_3''$ of compound 33 or compound 34 of Formula I or Formula II in Scheme 9 can be introduced from compound 31 or 32 respectively by procedures described for Group $R_1''$ in Scheme 2.

Scheme 10 Preparation of compounds of Formula I or Formula II in which Z₁ is CR₁ and Z₃ is NR₃" and Z₄ is N.

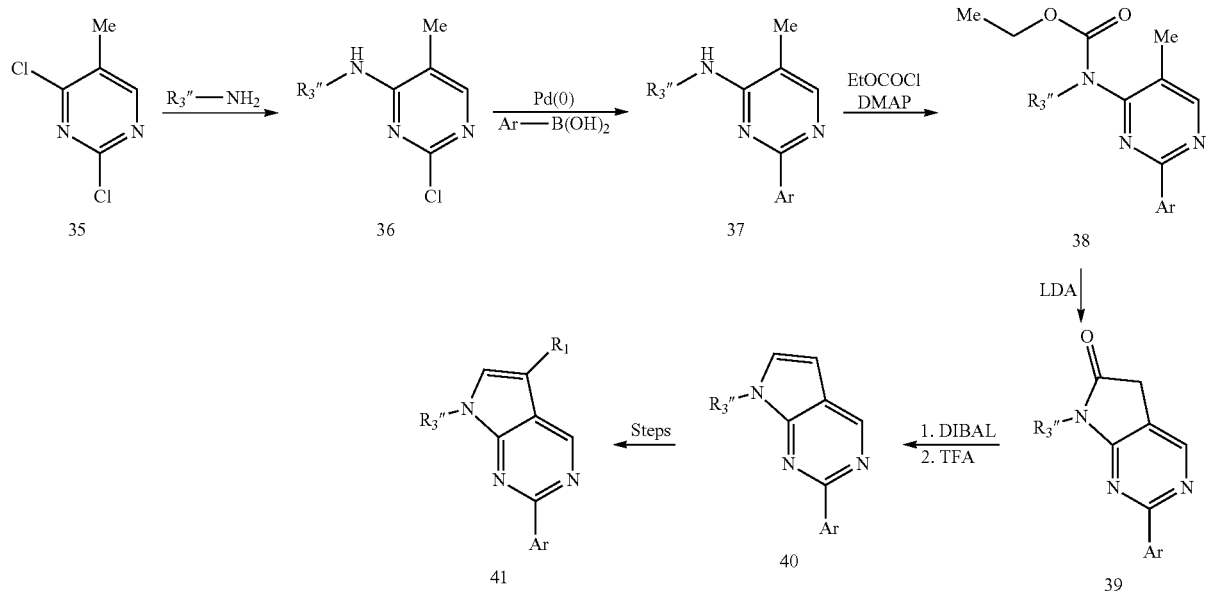

Scheme 10 illustrates a method to synthesize compounds of Formula I or Formula II in which Z₄ is N. In Step 1, 2, 4-dichloro-5-methylpyrimidine is reacted with a primary amine R₃"-NH₂ to give the corresponding pyrimidinyl-amine 36, which is coupled with arylboronic acid in the presence of Pd(0) to provide 2-arylpyrimidine intermediate 37. Compound 37 is converted over two steps to 2-aryl-5,7-dihydro-pyrrolo[2,3-d]pyrimidin-6-one 39 by consecutive treatment with ethyl chloroformate and LDA. Compound 39 is reduced with DIBAL to pyrimidinol that is subsequently treated with TFA to give 2-aryl-7H-pyrrolo[2,3-d]pyrimidine 40. Group R₁ of compound 41 Formula I or Formula II is introduced from Compound 34 in similar ways described for Group R₃ of Formula I or Formula II in Scheme 4, 5 or 6.

Specific examples for the preparation of compounds of Formula I or Formula II and the subformulae thereof, by the methods illustrated in Schemes 1-10 are provided in Examples 1-22, which follows. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

PREPARATION OF EXAMPLES

Example 1

Synthesis of 5-(2,6-Diethyl-Phenyl)-1H-pyrrolo[2,3-C]Pyridine

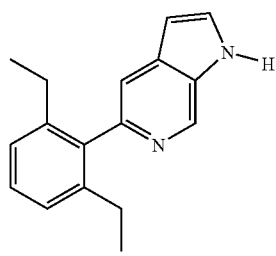

Step 1. Preparation of 2-(2,6-diethyl-phenyl)-4-methyl-5-nitro-pyridine

A mixture of 2-chloro-4-methyl-5-nitro-pyridine (5.0 g, 29.0 mmol), 2,6-diethylphenylboronic acid (7.7 g, 43.3 mmol), Pd(PPh₃)₄, (1.0 g, 0.9 mmol), Na₂CO₃ (9.1 g, 86.5 mmol) in a mixture of toluene (200 mL), water (43 mL) and ethanol (10 mL) is heated at 100° C. under nitrogen overnight. The mixture is cooled to room temperature, diluted with EtOAc, washed with water, dried (Na₂SO₄), and concentrated under reduced pressure. The residue is purified by chromatography on silica gel (Hexane/EtOAc, 6:1) to afford 2-(2,6-diethyl-phenyl)-4-methyl-5-nitro-pyridine as a colorless oil.

Step 2. Preparation of the Titled Compound

A solution of 2-(2,6-dimethyl-phenyl)-4-methyl-5-nitro-pyridine (2.0 g, 7.4 mmol) in 4 mL of Bredereck's reagent is heated at 150° C. overnight. The mixture is concentrated under reduced pressure. A mixture of the resultant residue and Raney Nickel (2.5 g) in methanol/THF (4 mL/4 mL) is stirred at 60° C. and a solution of hydrazine hydrate (1 mL) in THF (3 mL) is added over one hour. The reaction mixture is heated at 60° C. for 4 hours, cooled to room temperature and filtered through Celite. The filtrate is concentrated under reduced pressure. The residue is purified by chromatography on silica gel (MeOH/DCM, 5:100) to afford 5-(2,6-diethyl-phenyl)-1H-pyrrolo[2,3-c]pyridine as a tan solid. ¹H NMR (CDCl₃) 11.25 (br, 1H), 9.17 (s, 1H), 7.51 (s, 1H), 7.33 (t, 1H), 7.18 (d, 2H), 6.93 (d, 1H), 6.48 (d, 1H), 2.34 (m, 4H), 1.00 (t, 6H).

Example 2

Synthesis of 5-(2,6-Diethyl-Phenyl)-1-(1-Propyl-Butyl)-1H-Pyrrolo[2,3-C]Pyridine

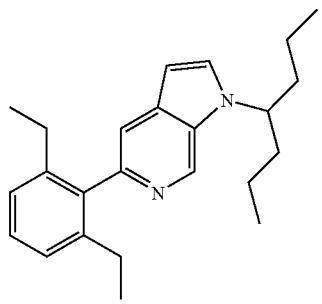

To a solution of 5-(2,6-diethyl-phenyl)-1H-pyrrolo[2,3-c]pyridine (32 mg, 0.13 mmol) in DMF (0.5 mL) is added NaH (95%, 6 mg). The reaction mixture is stirred at room temperature for 30 minutes, and 4-bromo-heptane (137 mg, 0.77 mmol) is added. The mixture is heated at 60° C. for three hours and cooled. To the mixture, water (2 mL) and EtOAc (2 mL) are added. The organic layer is separated, washed with water once and concentrated under reduced pressure. The residue is purified by PTLC (Hexane/EtOAc 4:1) to give the titled compound. $^1$H NMR: (CDCl$_3$) 8.82 (s, 1H), 7.43 (s, 1H), 7.32 (d, 1H), 7.31 (t, 1H), 7.16 (d, 2H), 6.87 (s, 1H), 6.53 (d, 1H), 4.42 (m, 1H), 2.32-2.40 (m, 4H), 1.86-1.95 (m, 4H), 1.15-1.32 (m, 4H), 1.03 (t, 6H), 0.84 (m, 6H).

Example 3

Synthesis OF 5-(2,6-Diethyl-Phenyl)-1-(1-Propyl-Butyl)-1H-pyrrolo[2,3-C]Pyridine-7-Carbonitrile

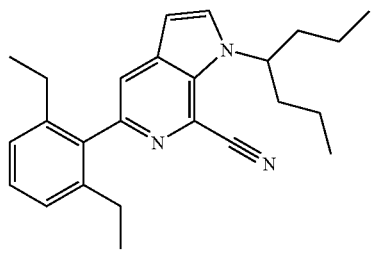

Step 1. Preparation of 5-(2,6-diethyl-phenyl)-1-(1-propyl-butyl)-1H-pyrrolo[2,3-c]pyridine 6-oxide 3-Chloro-benzenecarboperoxoic acid (c.a. 60%, 198 mg, 0.69 mmol) is added to a solution of 5-(2,6-diethyl-phenyl)-1-(1-propyl-butyl)-1H-pyrrolo[2,3-c]pyridine (200 mg, 0.057 mmol) in DCM (4 mL), and the mixture is stirred for 30 min at room temperature. The mixture is washed with a saturated aqueous Na$_2$CO$_3$ solution, brine, dried over Na$_2$SO$_4$ and concentrated under reduced pressure. Chromatography of the residue on silica gel (EtOAc) gives 5-(2,6-diethyl-phenyl)-1-(1-propyl-butyl)-1H-pyrrolo[2,3-c]pyridine 6-oxide as a white solid.

Step 2. Preparation of 5-(2,6-diethyl-phenyl)-1-(1-propyl-butyl)-1H-pyrrolo[2,3-c]pyridine-7-carbonitrile To a solution of 5-(2,6-diethyl-phenyl)-1-(1-propyl-butyl)-1H-pyrrolo[2,3-c]pyridine 6-oxide (220 mg, 0.6 mmol) in toluene (3 mL), is added dimethylsulfate (69 µL, 0.72 mmol), and the mixture is heated to 90° C. for 2 h. All volatiles are removed under reduced pressure. The residue is treated with water (2 mL), 10 M NaOH (20 drops) and KCN (200 mg, 3.1 mmol). The mixture is stirred for 12 h at room temperature. The product is extracted with EtOAc several times. The combined organic extracts are washed with brine, dried over Na$_2$SO$_4$, and concentrated under reduced pressure. Chromatography of the residue on silica gel (Hexane/EtOAc, 1:1) gives 5-(2,6-diethyl-phenyl)-1-(1-propyl-butyl)-1H-pyrrolo[2,3-c]pyridine-7-carbonitrile as a colorless oil: $^1$H NMR (CDCl$_3$) 7.66 (s, 1H), 7.50 (d, J=3 Hz, 1H), 7.32 (t, J=7 Hz, 1H), 7.16 (d, J=7 Hz, 2H), 6.70 (d, J=3 Hz, 1H), 5.34 (m, 1H), 2.32 (m, 4H), 1.92 (m, 4H), 1.44 (m, 2H), 1.21 (m, 2H), 1.02 (t, J=7 Hz, 6H), 0.95 (t, J=7 Hz, 6H); LCMS m/z 374.27 (3.06 min).

Example 4

Synthesis of 5-(2,6-Diethyl-Phenyl)-1-(2,5-Dimethyl-Benzyl)-1H-Pyrrolo[2,3-C]Pyridine

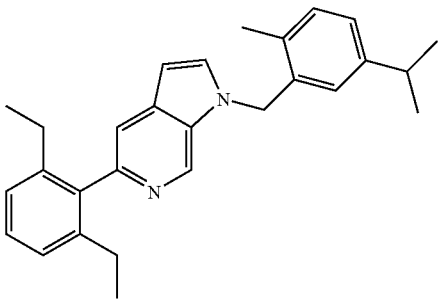

Step 1. Preparation of 5-isopropyl-2-methyl-benzaldehyde

To a solution of 2-bromo-4-isopropyl-1-methyl-benzene (863 mg, 4.0 mmol) in 10 mL of THF is added a solution of t-BuLi (1.7 M in pentane, 4.7 mL) dropwise at below −70° C. After addition, the reaction mixture is stirred at −78° C. for one hour. A solution of DMF (0.46 mL) in 1 mL of THF is added at the same temperature and stirred for additional one hour. The reaction mixture is allowed to warm to room temperature then poured into a mixture containing ice (50 g) and concentrated HCl (2 mL) and stirred for 15 minutes. To the mixture, ethyl ether (20 mL) is added. The organic layer is separated and the aqueous layer is extracted with ethyl ether. The organic solutions are combined, washed with brine, dried and concentrated to give 600 mg of 5-isopropyl-2-methyl-benzaldehyde. $^1$H NMR: (CDCl$_3$) 10.27 (s, 1H), 7.66 (d, 1H), 7.34 (d, 1H), 7.17 (d, 1H), 2.94 (m, 1H), 2.63 (s, 3H), 1.24 (d, 6H).

Step 2. Preparation of 2-chloromethyl-4-isopropyl-1-methyl-benzene

A mixture of 5-isopropyl-2-methyl-benzaldehyde (600 mg, 3.7 mmol) and sodium borohydride (280 mg, 7.4 mmol)

in 10 mL of EtOH is stirred at room temperature for one hour and then evaporated under reduced pressure. The residue is dissolved in EtOAc and the solution is washed with diluted HCl solution and brine, dried and concentrated. To the residue is added 2 mL of DCM and 1 mL of thionyl chloride. The mixture is stirred at room temperature for one hour and evaporated. The residue is dissolved in EtOAc and the solution is washed with NaHCO$_3$ solution and brine, dried and concentrated to give 2-chloromethyl-4-isopropyl-1-methyl-benzene as an oil.

Step 3. Preparation of the Titled Compound

To a solution of 5-(2,6-diethyl-phenyl)-1H-pyrrolo[2,3-c]pyridine (15 mg, 0.06 mmol) in DMF (0.5 mL) is added NaH (95%, 4 mg). The reaction mixture is stirred at room temperature for 30 minutes, and 2-chloromethyl-4-isopropyl-1-methyl-benzene (33 mg, 0.18 mmol) is then added. The mixture is heated at 60° C. for three hours and cooled. To the mixture, water (2 mL) and EtOAc (2 mL) are added. The organic layer is separated, washed with water once and concentrated under reduced pressure. The residue is purified by PTLC (Hexane/EtOAc 4:1) to give the titled compound. $^1$H NMR: (CDCl$_3$) 8.81 (s, 1H), 7.47 (s, 1H), 7.28 (t, 1H), 7.13-7.19 (m, 5H), 6.77 (s, 1H), 6.52 (d, 1H), 5.39 (s, 2H), 2.80 (m, 1H), 2.27-2.40 (m, 7H), 1.14 (d, 2H), 1.01 (t, 6).

Example 5

Synthesis of 5-(2,6-Diethyl-Phenyl)-1-(4-Isopropyl-Phenyl)-1H-Pyrrolo[2,3-C]Pyridine

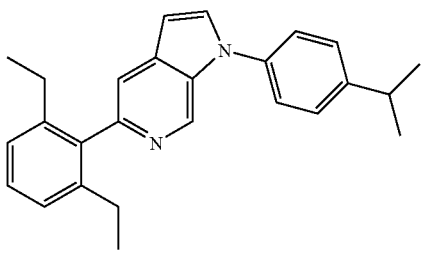

A mixture of 5-(2,6-diethyl-phenyl)-1H-pyrrolo[2,3-c]pyridine (700 mg, 2.8 mmol), 1-iodo-4-isopropyl-benzene (2.0 g, 8.1 mmol), CuI (1.0 g, 5.3 mmol), cesium carbonate (1.8 g, 5.5 mmol) and ethylenediamine (336 mg, 5.6 mmol) in dioxane (10 mL) is heated at 60° C. overnight. The reaction mixture is cooled, diluted with EtOAc, and filtered through Celite. The filtrate is concentrated under reduced pressure. The residue is purified by chromatography on silica gel (Hexane/EtOAc, 4:1) to afford 500 mg of 2.7 g of 5-(2,6-diethyl-phenyl)-1-(4-isopropyl-phenyl)-1H-pyrrolo[2,3-c]pyridine as a solid. $^1$H NMR: (CDCl$_3$) 8.97 (s, 1H), 7.41-7.52 (m, 6H), 7.28 (t, 1H), 7.15 (d, 2H), 6.68 (d, 1H), 3.03 (m, 1H), 2.36 (m, 4H), 1.34 (d, 6H), 1.01 (t, 6H).

Example 6

Synthesis of 5-(2,6-Diethyl-Phenyl)-1-(4,6-Dimethyl-Pyrimidin-2-yl)-1H-Pyrrolo[2,3-c]Pyridine

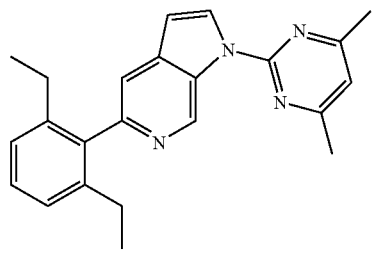

To a solution of 5-(2,6-diethyl-phenyl)-1H-pyrrolo[2,3-c]pyridine (10 mg, 0.04 mmol) in DMF (0.5 mL) is added NaH (95%, 3 mg). The reaction mixture is stirred at room temperature for 30 minutes, and then 2-chloro-4,6-dimethyl-pyrimidine (17 mg, 0.12 mmol)) is added. The mixture is heated at 60° C. overnight and cooled. Water (1 mL) and EtOAc (2 mL) are added to the mixture. The organic layer is separated, washed with water once and concentrated under reduced pressure. The residue is purified by PTLC (Hexane/EtOAc 4:1) to give the titled compound. $^1$H NMR: (CDCl$_3$) 10.21 (s, 1H), 8.48 (d, 1H), 7.47 (s, 1H), 7.28 (t, 1H), 7.15 (d, 2H), 6.87 (s, 1H), 6.68 (d, 1H), 2.55 (s, 6H), 2.36 (m, 4H), 1.03 (t, 6H).

Example 7

Preparation of 7-Chloro-5-(2,6-Diethyl-Phenyl)-3,4-Dimethyl-1H-Pyrrolo[2,3-C]Pyridine

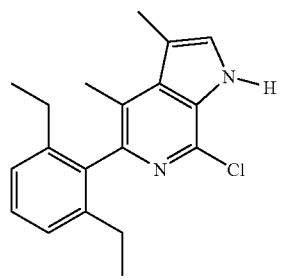

Step 1. Preparation of 2-chloro-5-methyl-pyridin-3-ylamine

To a solution of 2-chloro-5-methyl-3-nitro-pyridine (20 g, 0.12 mol) in 300 mL of ethanol is added SnCl$_2$ (132 g, 0.7 mol) slowly to keep internal temperature under 50° C. After addition completed, the reaction mixture is stirred for additional two hours at 50-55° C., then evaporated to dryness under reduced pressure. The residue is suspended in 400 mL of DCM, cooled with an ice bath, and neutralized carefully with 10N NaOH. The mixture is filtered through celite, washed the cake with DCM (100 mL×2). The filtrate is washed with water and brine, dried over MgSO₄, and concentrated under reduced pressure to give 16.5 g of 2-chloro-5-methyl-pyridin-3-ylamine.

Step 2. Preparation of 4,6-dibromo-2-chloro-5-methyl-pyridin-3-ylamine

To a solution of 2-chloro-5-methyl-pyridin-3-ylamine in acetonitrile is added NBS at room temperature. The reaction mixture is heated to 80° C. for 20 minutes and then evaporated under reduced pressure. The residue is dissolved in EtOAc. The solution is washed with water and brine, dried over MgSO₄ and concentrated to give 4,6-dibromo-2-chloro-5-methyl-pyridin-3-ylamine.

Step 3. Preparation of allyl-(4,6-dibromo-2-chloro-5-methyl-pyridin-3-yl)-amine To a solution of 4,6-dibromo-2-chloro-5-methyl-pyridin-3-ylamine (9.3 g, 31 mmol) and tetrabutylammonium bromide (1.0 g, 3.1 mmol) in anhydrous NMP (30 mL) is added NaH (60%, 1.5 g, 37.5 mmol) in one portion at 0° C. The mixture is gradually warmed to room temperature and stirred for two hours, then treated with allyl bromide (3.3 mL, 37.5 mmol) at 0° C., and stirred at 60° C. for three hours. The reaction mixture is cooled and partitioned between EtOAc and water. The organic layer is separated washed with water and brine, dried over MgSO₄ and concentrated under reduced pressure. Chromatography of the residue on silica gel (Hexane/EtOAc, 10:1) gives allyl-(4,6-dibromo-2-chloro-5-methyl-pyridin-3-yl)-amine.

Step 4. Preparation of 5-bromo-7-chloro-3,4-dimethyl-1H-pyrrolo[2,3-c]pyridine A mixture of allyl-(4,6-dibromo-2-chloro-5-methyl-pyridin-3-yl)-amine (5.0 g, 14.7 mmol), Pd(OAc)₂ (0.33 g, 1.47 mmol), tetrabutylammonium bromide (5.2 g, 16.2 mmol), K₂CO₃ (6.1 g, 44 mmol) in DMF (50 mL) is degassed, then stirred at 80° C. overnight. The mixture is diluted with EtOAc and washed with water and brine, dried over MgSO₄ and concentrated. Chromatography of the residue on silica gel (Hexane/EtOAc, 4:1) gives 3.2 g of 5-bromo-7-chloro-3,4-dimethyl-1H-pyrrolo[2,3-c]pyridine. ¹H NMR: (CDCl₃) 8.32 (1H, br), 7.14 (1H, q, J=1.1 Hz), 2.70 (3H, s), 2.46 (3H, d, J=1.1 Hz).

Step 5. Preparation of the Titled Compound

A mixture of 5-bromo-7-chloro-3,4-dimethyl-1H-pyrrolo[2,3-c]pyridine (610 mg, 2.34 mmol), diethylphenyl boronic acid (500 mg, 2.81 mmol), Pd(PPh₃)₄ (140 mg, 0.12 mmol) and Na₂CO₃ (2M, 5 mL) in toluene (30 mL) is degassed, and stirred at 86° C. overnight. The mixture is diluted with EtOAc and washed with water and brine. The organic layer is dried over MgSO₄ and concentrated under reduced pressure. Chromatography of the residue on silica gel (Hexane/EtOAc, 4:1) gives the titled compound. ¹H NMR: (CDCl₃) 9.10 (1H, br), 7.27 (1H, t, J=8.0 Hz), 7.14 (2H, d, J=8.0 Hz), 7.00 (1H, s), 2.46 (3H, s), 2.32 (3H, s), 2.27 (4H, q, J=7.5 Hz), 1.01 (6 H, t, J=7.5 Hz).

Example 8

Synthesis of 7-Chloro-5-(2,6-Diethyl-Phenyl)-1-(2, 5-Dimethyl-Benzyl)-3,4-Dimethyl-1H-Pyrrolo[2,3-c]Pyridine

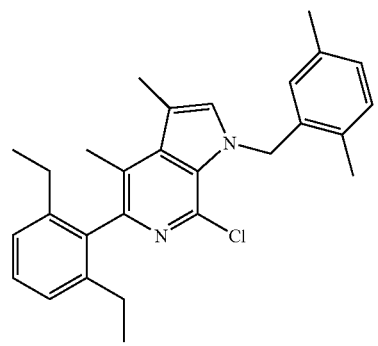

The titled compound is prepared from 7-chloro-5-(2,6-diethyl-phenyl)-3,4-dimethyl-1H-pyrrolo[2,3-c]pyridine (Example 7) by a procedure analogous to that described in Example 4. ¹H NMR: (CDCl₃) 7.42 (1H, t, J=7.8 Hz), 7.30 (1H, s), 7.22 (2H, d, J=7.8 Hz), 7.17 (1H, d, J=7.8 Hz), 7.13 (1H, d, J=7.8 Hz), 6.63 (1H, s), 5.71 (2H, s), 2.51 (3H, s), 2.46 (3H, s), 2.03-2.36 (m, 10H), 1.09 (6H, t, J=7.5 Hz).

Example 9

Synthesis of 5-(2,6-Diethyl-Phenyl)-3,4-Dimethyl-1H-Pyrrolo[2,3-C]Pyridine

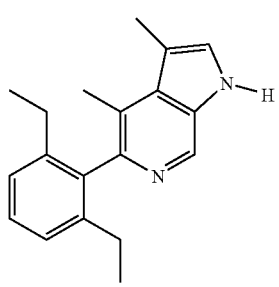

The titled compound is prepared from 7-chloro-5-(2,6-diethyl-phenyl)-3,4-dimethyl-1H-pyrrolo[2,3-c]pyridine (Example 7) by catalytic hydrogenation (10% Pd on carbon in MeOH with addition of 15% of 10 M NaOH) at 50 psi. ¹H NMR: (CDCl₃) 10.2 (1H, br), 8.85 (1H, s), 7.3 (1H, t, J=7.8

Hz), 7.20 (2H, d, J=7.8 Hz), 6.7 (1H, s), 2.50 (3H, s), 2.36 (3H, s), 2.29 (4H, q, J=7.0 Hz), 1.04 (6H, t, J=7.0 Hz).

Example 10

Synthesis of 5-(2,6-Diethyl-Phenyl)-1-(4-Isopropyl-Phenyl)-3,4-Dimethyl-1H-Pyrrolo[2,3-C]Pyridine

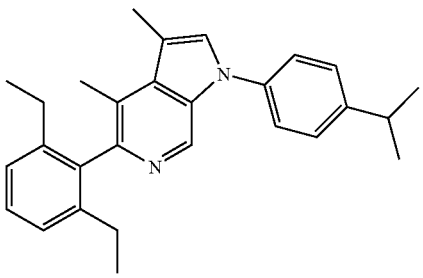

The titled compound is prepared from 5-(2,6-diethyl-phenyl)-3,4-dimethyl-1H-pyrrolo[2,3-c]pyridine (Example 9) by a procedure analogous to that described in Example 5. $^1$H NMR (CDCl$_3$) 8.80 (1H, s), 7.45 (2H, d, J=8.1 Hz), 7.40 (2H, d, J=8.1 Hz), 7.29 (1H, t, J=7.5 Hz), 7.23 (1H, s), 7.16 (2H, d, J=7.5 Hz), 3.00 (1H, m), 2.58 (3H, s), 2.40 (3H, s), 2.27 (4H, q, J=7.5 Hz), 1.32 (6H, d, J=7.8 Hz), 1.04 (6H, t, J=7.5 Hz).

Example 11

Preparation of 2-[5-(2,6-diethyl-Phenyl)-1-(4-isopropyl-Phenyl)-1H-Pyrrolo[2,3-c]pyridin-3-ylmethyl]-2-ethyl-butan-1-ol

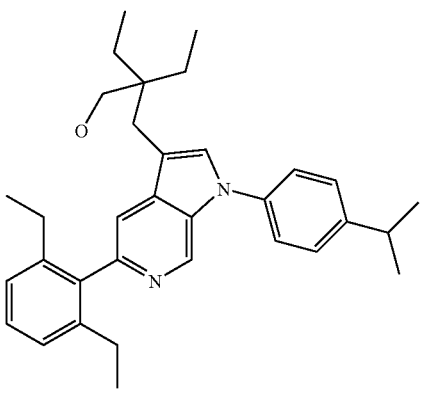

Step 1. Preparation of 3-bromo-5-(2,6-diethyl-phenyl)-1-(4-isopropyl-phenyl)-1H-pyrrolo[2,3-c]pyridine To a solution of 5-(2,6-diethyl-phenyl)-1-(4-isopropyl-phenyl)-1H-pyrrolo[2,3-c]pyridine (2.36 g, 6.4 mmol) in DCM (50 mL), NBS (1.25 g, 7.0 mmol) is added and the mixture is stirred at room temperature for 1 h. The mixture is concentrated under reduced pressure, and the product is dissolved in a 5:1 EtOAc/Hexane mixture and filtered over a small pad of silica gel. The solvent is removed under reduced pressure to afford 3-bromo-5-(2,6-diethyl-phenyl)-1-(4-isopropyl-phenyl)-1H-pyrrolo[2,3-c]pyridine.

Step 2. Preparation of 5-(2,6-diethyl-phenyl)-1-(4-isopropyl-phenyl)-3-vinyl-1 H-pyrrolo[2,3-c]pyridine A mixture of 3-bromo-5-(2,6-diethyl-phenyl)-1-(4-isopropyl-phenyl)-1H-pyrrolo[2,3-c]pyridine (440 mg, 0.98 mmol), tributyl-vinyl-stannane (620 mg, 1.96 mmol), Pd(PPh$_3$)$_4$ (113 mg, 0.098 mmol), and DMF (5 mL) is heated to 100° C. for 3 h under nitrogen. The mixture is poured to a saturated aqueous KF solution (20 mL), and the resultant mixture is stirred for three hours at room temperature. The product is extracted with EtOAc (70 mL×3). The combined organic extracts are washed with water (100 mL×3) and brine (100 mL), dried (Na$_2$SO$_4$), and concentrated under reduced pressure. The residue is purified by chromatography on silica gel (Hexane/EtOAc, 10:1) to afford 5-(2,6-diethyl-phenyl)-1-(4-isopropyl-phenyl)-3-vinyl-1H-pyrrolo[2,3-c]pyridine as a colorless oil.

Step 3. Preparation of 5-(2,6-diethyl-phenyl)-1-(4-isopropyl-phenyl)-1H-pyrrolo[2,3-c]pyridine-3-carbaldehyde To a solution of 5-(2,6-diethyl-phenyl)-1-(4-isopropyl-phenyl)-3-vinyl-1H-pyrrolo[2,3-c]pyridine (400 mg, 1.0 mmol) in a THF/water mixture (3:1, 10 mL), NaIO$_4$ (0.65 g, 3.0 mmol) and OsO$_4$ (4% in water, 3 drops) are added and the mixture is stirred for 18 hours at room temperature. The solvent is removed under reduced pressure, and the residue is extracted with EtOAc. The combined organic extracts are washed with brine, dried (Na$_2$SO$_4$), and concentrated under reduced pressure. The residue is purified by chromatography on silica gel (Hexane/EtOAc, 6:1) to afford 5-(2,6-diethyl-phenyl)-1-(4-isopropyl-phenyl)-1H-pyrrolo[2,3-c]pyridine-3-carbaldehyde as a colorless oil.

Step 4. Preparation of (E)-3-[5-(2,6-diethyl-phenyl)-1-(4-isopropyl-phenyl)-1 H-pyrrolo[2,3-c]pyridin-3-yl]-acrylic acid ethyl ester To a solution of triethyl phosphonoacetate (120 μL, 0.6 mmol) in THF (3 mL) cooled to 0° C., NaH (60 wt % in mineral oil, 36 mg, 0.9 mmol) is added and the mixture is stirred at room temperature for one hour. The mixture is cooled to 0° C., and a solution of 5-(2,6-diethyl-phenyl)-1-(4-isopropyl-phenyl)-1H-pyrrolo[2,3-c]pyridine-3-carbaldehyde (200 mg, 0.5 mmol) in THF (1 mL) is added. The reaction is stirred at room temperature for 3 h. An aqueous saturated NH$_4$Cl solution (10 mL) is added and THF is removed under reduced pressure. The product is extracted with EtOAc. The combined organic extracts are washed with brine, dried (Na$_2$SO$_4$), and concentrated under reduced pressure. The obtained residue is purified by chromatography on silica gel (Hexane/EtOAc, 4:1) to afford (E)-3-[5-(2,6-diethyl-phenyl)-1-(4-isopropyl-phenyl)-1H-pyrrolo[2,3-c]pyridin-3-yl]-acrylic acid ethyl ester as a colorless oil.

Step 5. Preparation of 3-[5-(2,6-diethyl-phenyl)-1-(4-isopropyl-phenyl)-1H-pyrrolo[2,3-c]pyridin-3-yl]-propionic acid ethyl ester A mixture of (E)-3-[5-(2,6-diethyl-phenyl)-1-(4-isopropyl-phenyl)-1H-pyrrolo[2,3-c]pyridin-3-yl]-acrylic acid ethyl ester (140 mg, 0.3 mmol) and 10% Pd/C (20 mg) in EtOH (4 mL) is stirred under hydrogen (1 atm) for 18 hour at room temperature. The mixture is filtered over celite and concentrated under reduced pressure to afford 3-[5-(2,6-diethyl-phenyl)-1-(4-isopropyl-phenyl)-1H-pyrrolo[2,3-c]pyridin-3-yl]-propionic acid ethyl ester as a colorless oil.

Step 6. Preparation of 2-[5-(2,6-Diethyl-phenyl)-1-(4-isopropyl-phenyl)-1H-pyrrolo[2,3-c]pyridin-3-ylmethyl]-2-ethyl-butyric acid ethyl ester To a solution of 3-[5-(2,6-diethyl-phenyl)-1-(4-isopropyl-phenyl)-1H-pyrrolo[2,3-c]pyridin-3-yl]-propionic acid ethyl ester (120 mg, 0.25 mmol) in THF (3 mL) at −78° C. is added LDA (1.8 M solution in heptate/THF/ethylbenzene, 0.341 mL, 0.61 mmol). The mixture is stirred at −78° C. for 25 minutes and iodoethane (0.20 mL, 2.5 mmol) is added. The mixture is allowed to warm up to room temperature and stirred for 18 hours. To the mixture, an aqueous saturated NH₄Cl solution (5 mL) is added, and THF is removed under reduced pressure. The product is extracted with EtOAc. The combined organic extracts are washed with brine, dried (Na₂SO₄), and concentrated under educed pressure. Chromatography of the residue on silica gel (Hexane/EtOAc, 4:1) gives 2-[5-(2,6-diethyl-phenyl)-1-(4-isopropyl-phenyl)-1H-pyrrolo[2,3-c]pyridin-3-ylmethyl]-2-ethyl-butyric acid ethyl ester as a colorless oil.

Step 7. Preparation of the Titled Compound

To a solution of 2-[5-(2,6-diethyl-phenyl)-1-(4-isopropyl-phenyl)-1H-pyrrolo[2,3-c]pyridin-3-ylmethyl]-2-ethyl-butyric acid ethyl ester (100 mg, 0.19 mmol) in DCM (10 mL) at −78° C., DIBAL (1M solution in toluene, 0.95 mL, 0.9 mmol) is added and the mixture is allowed to gradually warm up room temperature, at which stirring is continued for 2 h. To the mixture, a saturated aqueous Rochelle's salt solution (10 mL) is added and stirring is continued for 1 h. The organic layer is separated and the aqueous is extracted with DCM. The combined organic extracts are washed with brine, dried (Na₂SO₄), and concentrated under reduced pressure. The residue is purified by chromatography on silica gel (Hexane/EtOAc, 2:1) to afford 2-[5-(2,6-diethyl-phenyl)-1-(4-isopropyl-phenyl)-1H-pyrrolo[2,3-c]pyridin-3-ylmethyl]-2-ethyl-butan-1-ol as colorless oil: LCMS m/z 483.21 (2.64 min)

Example 12

Synthesis of 3-[5-(2,6-diethyl-phenyl)-1-(4-isopropyl-phenyl)-1H-pyrrolo[2,3-c]pyridin-3-yl]-propan-1-ol

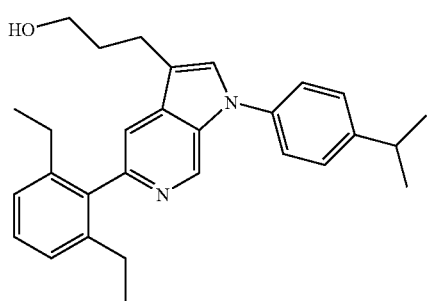

To a solution of 3-[5-(2,6-diethyl-phenyl)-1-(4-isopropyl-phenyl)-1H-pyrrolo[2,3-c]pyridin-3-yl]-propionic acid ethyl ester (220 mg, 0.47 mmol, prepared by the procedure described in Example 11, Step 5) in DCM (4 mL) at −78° C., DIBAL (1M solution in toluene, 2.35 mL, 2.3 mmol) is added, and the mixture is stirred at −78° C. for 3 h. Reaction is warmed up to room temperature, and a saturated aqueous Rochelle's salt solution (6 mL) is carefully added. Stirring is continued for another 1 hour. The organic layer is separated, and the aqueous phase is extracted with DCM. The combined organic solutions are washed with brine, dried over Na₂SO₄, and concentrated under reduced pressure. Chromatography of the residue affords 3-[5-(2,6-diethyl-phenyl)-1-(4-isopropyl-phenyl)-1H-pyrrolo[2,3-c]pyridin-3-yl]-propan-1-ol as a colorless oil. ¹H NMR: (CDCl₃) 8.97 (s, 1H), 7.49 (s, 1H), 7.48 (d, J=12 Hz, 2H), 7.42 (d, J=10 Hz, 2H), 7.32 (s, 1H), 7.27 (t, J=10 Hz, 1H), 7.15 (d, 12 Hz, 2H), 3.76 (t, J=6 Hz, 2H), 3.01 (m, 1H), 2.89 (t, J=6 Hz, 2H), 2.35 (m, 4H), 2.01 (m, 2H), 1.33 (d, J=10 Hz, 6H), 1.073 (t, J=10 Hz, 6H); LCMS m/z 427.32 (2.32 min).

Example 13

Synthesis of 1-[5-(2,6-diethyl-phenyl)-1-(4-isopropyl-phenyl)-1H-pyrrolo[2,3-C]Pyridin-3-yl]-3-methyl-butan-1-OL

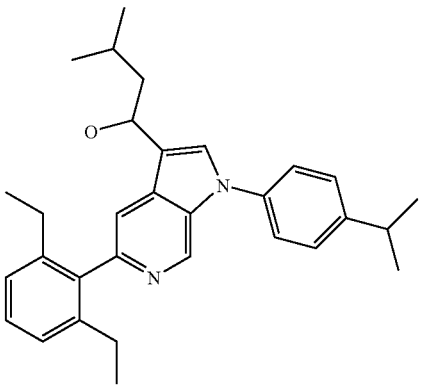

To a solution of 5-(2,6-diethyl-phenyl)-1-(4-isopropyl-phenyl)-1H-pyrrolo[2,3-c]pyridine-3-carbaldehyde (50 mg, 0.13 mmol, prepared by the procedure described in Example 11, Step 3) in THF (2 mL) at −78° C., iso-butylmagnesium chloride (1M solution in THF, 300 μL, 0.32 mmol) is added. The mixture is stirred at −78° C. for two hours and is subsequently allowed to warm to room temperature. A saturated aqueous NH₄Cl solution (5 mL) is added, and THF is removed under reduced pressure. The product is extracted with EtOAc. The combined organic extracts are washed with brine, dried over Na₂SO₄, and concentrated under reduced pressure. Chromatography of the residue affords 1-[5-(2,6-dimethyl-phenyl)-1-(4-isopropyl-phenyl)-1H-pyrrolo[2,3-c]pyridin-3-yl]-3-methyl-butan-1-ol as colorless oil. ¹H NMR: (CDCl₃) 8.97 (s, 1H), 7.64 (s, 1H), 7.9 (s, 1H), 7.48 (d, J=120 Hz, 2H), 7.41 (d, J=10 Hz, 2H), 7.29 (t, J=10 Hz, 1H), 7.15 (d, J=12 Hz, 2H), 5.13 (m, 1H), 3.95 (m, 1H), 2.44 (m, 4H), 1.34 (d, J=14 Hz, 6H), 1.04 (t, J=10 Hz, 6H); LCMS m/z 455.34 (2.58 min).

Example 14

Synthesis of acetic acid 1-[5-(2,6-diethyl-phenyl)-1-(4-isopropyl-phenyl)-1H-pyrrolo[2,3-C]pyridin-3-YL]-3-methyl-butyl ester

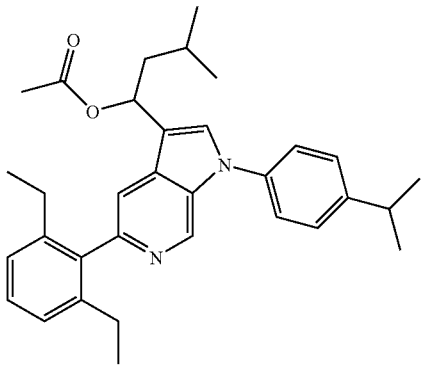

To a solution of 1-[5-(2,6-diethyl-phenyl)-1-(4-isopropyl-phenyl)-1H-pyrrolo[2,3-c]pyridin-3-yl]-3-methyl-butan-1-ol (20 mg, 0.044 mmol) in DCM (2 mL), N,N-diisopropyl-ethylamine (15 µL, 0.08 mmol), acetic anhydride (6.6 µL, 0.06 mmol), and DMAP (1 mg) were added. The mixture is stirred at room temperature for 4 h. All volatiles are removed under reduced pressure and the residue is purified by chromatography to afford acetic acid 1-[5-(2,6-diethyl-phenyl)-1-(4-isopropyl-phenyl)-1H-pyrrolo[2,3-c]pyridin-3-yl]-3-methyl-butyl ester as a colorless oil.

Example 15

Synthesis of 1-[5-(2,6-dimethyl-phenyl)-1-(6-ethyl-2-methoxy-pyrimidin-4-YL)-1H-pyrrolo[2,3-C]pyridin-3-yl]-2-ethyl-butan-1-OL

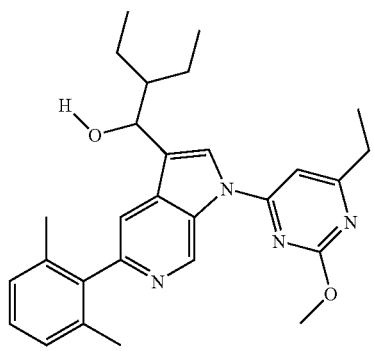

Step 1. Preparation of 2-(2,6-dimethyl-phenyl)-4-methyl-5-nitro-pyridine

A mixture of 2,6-dimethylphenylboronic acid (6.5 g, 43.5 mmol), 2-chloro-4-methyl-5-nitro-pyridine (5 g, 28.9 mmol), Pd(PPh$_3$)$_4$, (1.5 g, 1.5 mmol), Na$_2$CO$_3$ (4.6 g, 43.5 mm water (20 mL), and EtOH (5 mL) is heated in a sealed tube under nitrogen at 110° C. for 18 hours. The mixture is cooled to room temperature, diluted with EtOAc (150 mL), washed with saturated solution of Na$_2$CO$_3$ (50 mL 3×), water (50 mL) and brine (50 mL), dried (Na$_2$SO$_4$), and concentrated under reduced pressure. The residue is purified by chromatography on silica gel (Hexane/EtOAc, 6:1) to afford 2-(2,6-dimethyl-phenyl)-4-methyl-5-nitro-pyridine as a colorless oil.

Step 2. Preparation of {(E)-2-[2-(2,6-dimethyl-phenyl)-5-nitro-pyridin-4-yl]-vinyl}-dimethyl-amine To a solution of the 2-(2,6-dimethyl-phenyl)4-methyl-5-nitro-pyridine (8 g, 33.0 mmol) in anhydrous DMF (30 mL), Bredereck's reagent (20 mL, 99.0 mmol) is added, and the mixture is heated for 1 h at 90° C. The mixture is concentrated under reduced pressure, and the residue is dissolved a mixture of EtOAc-hexane-DCM (1:1:1, 200 mL) and filtered over small pad of silica gel. Removal of the solvent under reduced pressure gives the crude {(E)-2-[2-(2,6-dimethyl-phenyl)-5-nitro-pyridin-4-yl]-vinyl}-dimethyl-amine which is used in the following step.

Step 3. Preparation of 5-(2,6-dimethyl-phenyl)-1H-pyrrolo[2,3-c]pyridine

To a solution of {(E)-2-[2-(2,6-dimethyl-phenyl)-5-nitro-pyridin-4-yl]-vinyl}-dimethyl-amine (10 g, 33.6 mmol) in glacial acetic acid (150 mL), zinc dust (22 g, 336 mmol) is added and the mixture is stirred at room temperature for 1 h. Temperature is raised to 90° C. at which the mixture is maintained for another 30 min. The resultant suspension is filtered over celite and concentrated under reduced pressure to afford 5-(2,6-dimethyl-phenyl)-1H-pyrrolo[2,3-c]pyridine as a brown solid.

Step 4. Preparation of 1-[5-(2,6-Dimethyl-phenyl)-1H-pyrrolo[2,3-c]pyridin-3-yl]-2-ethyl-butan-1-one 2-Ethyl-butyryl chloride (0.799 mL, 5.8 mmol) is added to a suspension of AlCl$_3$ (770 mg, 5.8 mmol) in DCM (20 mL) at −10° C. The resultant solution is stirred for 15 min at the same temperature, and 5-(2,6-dimethyl-phenyl)-1H-pyrrolo [2,3-c]pyridine (0.5 g, 2.2 mmol) is added as a solution in DCM (3 mL). The mixture is stirred for 18 h at room temperature. A saturated aqueous NaCl solution (30 mL) is carefully added to the mixture, and stirring is continued for 2 h. Organic layer is separated, and the aqueous solution is extracted with DCM. The combined organic solutions are washed with water and brine, dried (Na$_2$SO$_4$), and concentrated under reduced pressure. Chromatography of the residue on silica gel 10% MeOH-DCM affords 1-[5-(2,6-dimethyl-phenyl)-1H-pyrrolo[2,3-c]pyridin-3-yl]-2-ethyl-butan-1-one as colorless oil.

Step 5. Preparation of 1-[1-(2-chloro-6-ethyl-pyrimidin-4-yl)-5-(2,6-dimethyl-phenyl)-1H-pyrrolo[2,3-c]pyridin-3-yl]-2-ethyl-butan-1-one A mixture of 1-[5-(2,6-dimethyl-phenyl)-1H-pyrrolo[2,3-c]pyridin-3-yl]-2-ethyl-butan-1-one (200 mg, 0.62 mmol), 2,4-dichloro-6-ethyl-pyrimidine (221 mg, 1.25 mmol), Cs$_2$CO$_3$ (305 mg, 0.93 mmol), and DMF (3 mL) is stirred for 4 h at room temperature. The mixture is diluted with EtOAc (10 mL) and the obtained solution is washed with water and brine, dried (Na$_2$SO$_4$), and concentrated under reduced pressure. Chromatography of the residue on silica gel (hexane-EtOAc, 1:1) gives 1-[1-(2-chloro-6-ethyl-pyrimidin-4-yl)-5-(2,6-dimethyl-phenyl)-1H-pyrrolo[2,3-c]pyridin-3-yl]-2-ethyl-butan-1-one as colorless oil.

Step 6. Preparation of 1-[1-(2-chloro-6-ethyl-pyrimidin-4-yl)-5-(2,6-dimethyl-phenyl)-1H-pyrrolo[2,3-c]pyridin-3-yl]-2-ethyl-butan-1-ol To a solution of 1-[1-(2-chloro-6-ethyl-pyrimidin-4-yl)-5-(2,6-dimethyl-phenyl)-1H-pyrrolo[2,3-c]pyridin-3-yl]-2-ethyl-butan-1-one (150 mg, 0.32 mmol) in a (4:1) mixture EtOH—H$_2$O (4 mL) at −30° C., NaBH$_4$ (70 mg, 1.8 mmol) is added, and the mixture is allowed gradually warm up to room temperature at which the reaction is maintained for 2 h. The mixture is concentrated under reduced pressure, and an aqueous saturated Rochelle's salt solution (10 mL) is added. The resulting suspension is stirred at room temperature for 1 h, and the product is extracted with DCM. The obtained solution is washed with brine, dried (Na$_2$SO$_4$), and concentrated under reduced pressure. Chromatography of the residue on silica gel (hexane-EtOAc, 1:1) gives 1-[1-(2-chloro-6-ethyl-pyrimidin-4-yl)-5-(2,6-dimethyl-phenyl)-1H-pyrrolo[2,3-c]pyridin-3-yl]-2-ethyl-butan-1-ol as colorless oil.

Step 7. Preparation of the Titled Compound

Cs$_2$CO$_3$ (85 mg, 0.26 mmol) is added to a solution of 1-[1-(2-chloro-6-ethyl-pyrimidin-4-yl)-5-(2,6-dimethyl-phenyl)-1H-pyrrolo[2,3-c]pyridin-3-yl]-2-ethyl-butan-1-ol (100 mg, 0.22 mmol) in MeOH (4 mL). The mixture is heated at 60° C. for 30 min. The mixture is concentrated under reduced pressure, diluted with water (5 mL), and the product is extracted with DCM. The combined organic extracts are washed with brine, dried (Na$_2$SO$_4$), and concentrated under reduced pressure. Chromatography of the residue silica gel (hexane-EtOAc, 1:1) gives 1-[5-(2,6-dimethyl-phenyl)-1-(6-ethyl-2-methoxy-pyrimidin-4-yl)-1H-pyrrolo[2,3-c]pyridin-3-yl]-2-ethyl-butan-1-ol as colorless oil: $^1$H NMR (CDCl$_3$) 10.18 (s, 1H), 8.39 (s, 1H), 7.54 (s, 1H), 7.27-7.12 (m, 3H), 6.41 (s, 1H), 5.00 (d, J=6 Hz, 1H), 4.12 (s, 3H), 2.78 (dd, J=7, 15 Hz, 2H), 2.075 (s, 6H), 1.39 (t, J=7 Hz, 2.05-1.26 (m, 5H), 0.92 (t, J=7 Hz, 6H); LCMS (1) m/z 459.33 (2.65 min).

Example 16

Preparation of 1-[5-(2,6-dimethyl-phenyl)-1-(6-isopropoxy-pyridazin-3-yl)-1H-pyrrolo[2,3-C]pyridin-3-yl]-2-ethyl-butan-1-ol

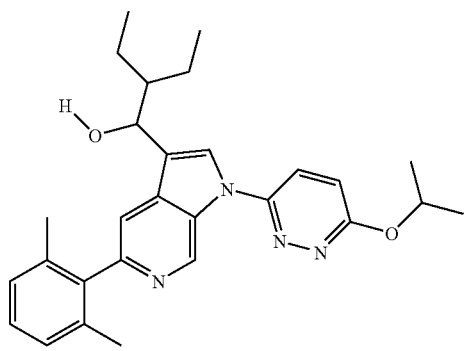

Step 1. Preparation of 1-[5-(2,6-dimethyl-phenyl)-1-(6-isopropoxy-pyridazin-3-yl)-1 H-pyrrolo[2,3-c]pyridin-3-yl]-2-ethyl-butan-1-one To a solution of 1-[5-(2,6-dimethyl-phenyl)-1H-pyrrolo[2,3-c]pyridin-3-yl]-2-ethyl-butan-one (100 mg, 0.31 mmol) (Step 4, Example 1) in 2 mL of DMF, 3-chloro-6-isopropoxy-pyridazine (161 mg, 0.93 mmol) is added, followed by Cs$_2$CO$_3$ (306 mg, 0.93 mmol). The mixture is heated to 149° C. for 18 h under nitrogen. The mixture is diluted with EtOAc (7 mL) and washed with water (3×5 mL) and brine (5 mL), dried (Na$_2$SO$_4$), and concentrated under reduced pressure. Chromatography of the residue on silica gel (hexane-EtOAc, 1:1) gives 1-[5-(2,6-dimethyl-phenyl)-1-(6-isopropoxy-pyridazin-3-yl)-1H-pyrrolo[2,3-c]pyridin-3-yl]-2-ethyl-butan-1-one as colorless oil.

Step 2. Preparation of the Titled Compound

To a solution of 1-[5-(2,6-dimethyl-phenyl)-1-(6-isopropoxy-pyridazin-3-yl)-1H-pyrrolo[2,3-c]pyridin-3-yl]-2-ethyl-butan-1-one (70 mg, 0.15 mmol) in a (4:1) EtOH—H$_2$O mixture (5 mL) −30° C., NaBH$_4$ (50 mg, 1.3 mmol) is added, and the mixture is allowed to gradually warm up to room temperature at which the stirring is continued for 2 h. The mixture is concentrated under reduced pressure. The residue is diluted with a saturated aqueous solution of Rochelle's salt (10 mL), and the product is extracted with DCM. The combined organic solutions are washed with brine, dried (Na$_2$SO$_4$) and concentrated under reduced pressure. Chromatography of the residue on silica gel (hexane-EtOAc, 1:1) gives 1-[5-(2,6-dimethyl-phenyl)-1-(6-isopropoxy-pyridazin-3-yl)-1H-pyrrolo[2,3-c]pyridin-3-yl]-2-ethyl-butan-1-ol as colorless oil. $^1$H NMR (CDCl$_3$) 9.52 (s, 1H), 7.83 (s, 1H), 7.71 (s, 1H), 7.69 (s, 1H), 7.59 (s, 1H), 7.22-7.10 (m, 3H), 5.62 (m, 1H), 5.21 (m, 1H), 2.08 (s, 6H), 1.47 (d, J=7 Hz, 6H), 1.08 (s, 9H); LCMS m/z 459.14 (2.48 min).

Example 17

Synthesis of 5-(2,6-diethyl-phenyl)-1-(4-isopropyl-phenyl)-3-thiazol-2-yl-1H-pyrrolo[2,3-C]pyridine

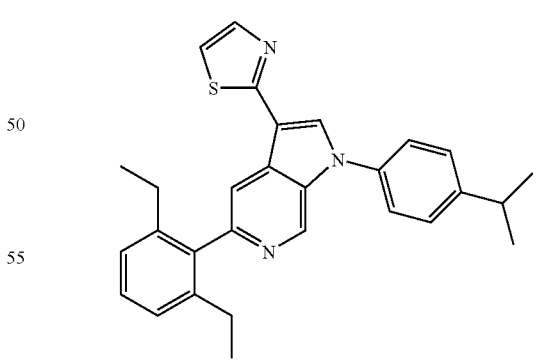

A mixture of 3-bromo-5-(2,6-diethyl-phenyl)-1-(4-isopropyl-phenyl)-1H-pyrrolo[2,3-c]pyridine (50 mg, 0.11 mmol), 2-tributylstannanyl-thiazole (83 mg, 0.22 mmol), Pd(PPh$_3$)$_4$ (20 mg, 0.017 mmol), and DMF (3 mL) is stirred under nitrogen at 100° C. for 18 h. The mixture is diluted with EtOAc (15 mL) and washed with water and brine, dried (Na$_2$SO$_4$), and concentrated under reduced pressure. Chromatography of the residue gives 5-(2,6-diethyl-phenyl)-1-(4-isopropyl-phenyl)-3-thiazol-2-yl-1H-pyrrolo[2,3-c]pyridine as colorless oil: ¹H NMR (CDCl₃) 9.03 (s, 1H), 8.15 (s, 1H), 7.84 (d, J=1 Hz, 1H), 7.56 (d, J=12 Hz, 2H), 7.46 (d, J=12 Hz, 2H), 7.32 (t, J=7 Hz, 1H), 7.31-7.26 (m, 3H), 7.20 (s, 1H), 3.05 (m, 1H), 2.39 (m, 4H), 1.35 (d, J=8 Hz, 6H), 1.09 (t, J=8 Hz, 6H); LCMS m/z 452.23 (2.93 min).

Example 18

Synthesis of 4-[5-(2,6-diethyl-phenyl)-1-(1-propyl-butyl)-1H-pyrrolo[2,3-C]pyridin-3-YL]-piperidine-1-carboxylic acid tert-butyl ester

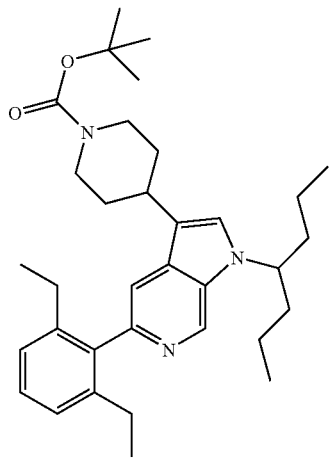

Step 1. Preparation of 4-[5-(2,6-diethyl-phenyl)-1H-pyrrolo[2,3-c]pyridin-3-yl]-3,6-dihydro-2H-pyridine-1-carboxylic acid tert-butyl ester A mixture of 5-(2,6-diethyl-phenyl)-1H-pyrrolo[2,3-c]pyridine (200 mg, 0.90 mmol), 4-oxo-piperidine-1-carboxylic acid tert-butyl ester (358 mg, 1.8 mmol), Cs₂CO₃ (586 mg, 1.8 mmol), and MeOH (6 mL) is refluxed for 18 h. MeOH is removed under reduced pressure. The residue is treated with acetic acid (0.5 mL) and water (3 mL) and is extracted with EtOAc. The combined organic extracts are washed with brine, dried over Na₂SO₄, and concentrated under reduced pressure. Chromatography of the residue affords 4-[5-(2,6-Diethyl-phenyl)-1H-pyrrolo[2,3-c]pyridin-3-yl]-3,6-dihydro-2H-pyridine-1-carboxylic acid tert-butyl ester as colorless oil.

Step 2. Preparation of 4-[5-(2,6-diethyl-phenyl)-1-(1-propyl-butyl)-1H-pyrrolo[2,3-c]pyridin-3-yl]-3,6-dihydro-2H-pyridine-1-carboxylic acid tert-butyl ester To a solution of the 4-[5-(2,6-diethyl-phenyl)-1H-pyrrolo[2,3-c]pyridin-3-yl]-3,6-dihydro-2H-pyridine-1-carboxylic acid tert-butyl ester (120 mg, 0.30 mmol) in DMF (4 mL), NaH (60 wt % suspension in mineral oil, 36 mg, 0.89 mmol) is added followed by 4-bromoheptane (159 mg, 0.89 mmol). The mixture is stirred for 40 h at room temperature. The mixture is poured to water (10 mL), and the product is extracted with EtOAc. The combined organic extracts are washed with brine, dried over Na₂SO₄, and concentrated under reduced pressure. Chromatography of the residue affords 4-[5-(2,6-diethyl-phenyl)-1-(1-propyl-butyl)-1H-pyrrolo[2,3-c]pyridin-3-yl]-3,6-dihydro-2H-pyridine-1-carboxylic acid tert-butyl ester as colorless oil.

Step 3. Preparation of the Titled Compound

The 4-[5-(2,6-diethyl-phenyl)-1-(1-propyl-butyl)-1H-pyrrolo[2,3-c]pyridin-3-yl]-3,6-dihydro-2H-pyridine-1-carboxylic acid tert-butyl ester (50 mg, 0.10 mmol) is dissolved in EtOH (2 mL), 10% Pd/C (5 mg) is added, and the mixture is shook in a parr-reactor under 50 psi of H₂ over 18 h. Filter, remove solvents and chromatograph the residue affords 4-[5-(2,6-diethyl-phenyl)-1-(1-propyl-butyl)-1H-pyrrolo[2,3-c]pyridin-3-yl]-piperidine-1-carboxylic acid tert-butyl ester as colorless oil: ¹H NMR (CDCl₃) 8.80 (s, 1H), 7.36 (s, 1H), 7.27 (t, J=7 Hz, 1H), 7.13 (d, J=12 Hz, 2H), 7.04 (s, 1H), 4.36 (m, 1H), 4.21 (m, 1H), 2.96 (m, 1H), 2.92 (m, 1H), 2.34 (m, 4H), 2.03 (m, 1H), 1.86 (m, 4H), 1.63 (m, 2H), 1.49 (s, 9H), 1.28 (m, 4H), 1.02 (t, J=8 Hz, 6H), 0.90 (t, J=8 Hz, 6H); LCMS m/z 532.39 (2.58 min).

Example 19

Synthesis of [5-(2,6-diethyl-phenyl)-1-(4-isopropyl-phenyl)-1H-pyrrolo[2,3-C]pyridin-3-YL]-acetic acid methyl ester

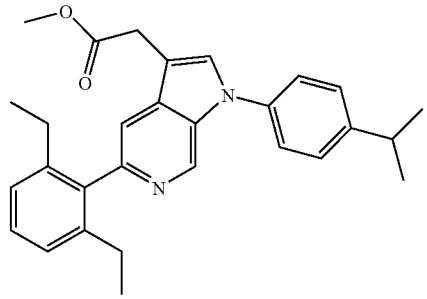

Step 1. Preparation of [5-(2,6-diethyl-phenyl)-1H-pyrrolo[2,3-c]pyridin-3-yl]-acetonitrile A mixture of 5-(2,6-Diethyl-phenyl)-1H-pyrrolo[2,3-c]pyridine (1 g, 4.5 mmol), formaldehyde (37% solution in water, 1.4 mL, 18 mmol), dimethylamine (2 M solution in MeOH, 18 mL, 18 mmol) and EtOH (50 mL) is heated to reflux for 2.5 h. All volatiles are removed under reduced pressure. The residue is mixed with toluene, which is subsequently removed under reduced pressure. The residue is dissolved in DMF (15 mL), KCN (2.6 g, 40 mmol) is added and the mixture was refluxed for 2 h. DMF is removed under reduced pressure, and the residue is purified by chromatography on silica gel (EtOAc) to afford [5-(2,6-diethyl-phenyl)-1H-pyrrolo[2,3-c]pyridin-3-yl]-acetonitrile as colorless oil.

Step 2. Preparation of [5-(2,6-diethyl-phenyl)-1-(4-isopropyl-phenyl)-1H-pyrrolo[2,3-c]pyridin-3-yl]-acetonitrile A mixture of [5-(2,6-diethyl-phenyl)-1H-pyrrolo[2,3-c]pyridin-3-yl]-acetonitrile (800 mg, 3.1 mmol), 1-iodo-4-isopropyl-benzene (1.13 g, 4.6 mmol), copper iodide (874 mg, 4.6 mmol), Cs$_2$CO$_3$ (1.50 g, 4.6 mmol) and ethylenediamine (30 μL, 4.6 mmol), and dioxane (100 mL) is heated to 60° C. under nitrogen for 18 h. The mixture is diluted with EtOAc and filtered over a small pad of silica gel. The obtained solution is concentrated under reduced pressure, and the residue is purified by chromatography on silica gel (hexane-EtOAc, 5:1) to afford [5-(2,6-diethyl-phenyl)-1-(4-isopropyl-phenyl)-1H-pyrrolo[2,3-c]pyridin-3-yl]-acetonitrile as colorless oil.

Step 3. Preparation of the Titled Compound

A solution of [5-(2,6-diethyl-phenyl)-1-(4-isopropyl-phenyl)-1H-pyrrolo[2,3-c]pyridin-3-yl]-acetonitrile (1.3 g, 3.4 mmol) in MeOH saturated with HCl (20 mL) is refluxed for 18 h. All volatiles are removed under reduced pressure and the residue is treated with a saturated aqueous NaHCO$_3$ solution (10 mL), and the product is extracted with EtOAc. The combined organic extracts are washed with brine, dried over Na$_2$SO$_4$ and concentrated under educed pressure. Chromatography of the residue on silica gel (hexane-EOtAc, 3:1) affords [5-(2,6-diethyl-phenyl)-1-(4-isopropyl-phenyl)-1H-pyrrolo[2,3-c]pyridin-3-yl]-acetic acid methyl ester as yellow oil: $^1$H NMR (CDCl$_3$) 8.96 (s, 1H), 7.50 (s, 1H), 7.48 (d, J=10 Hz, 2H), 7.42 (s, 1H), 7.28 (t, J=8 Hz, 1H), 7.15 (d, J=10 Hz, 1H), 3.81 (s, 2H), 3.70 (s 3H), 2.36 (m, 4H), 1.33 (f, J=8 Hz, 6H), 1.05 (t, J=8 Hz, 6H); LCMS m/z 441.19 (2.45 min).

Example 20

Synthesis of isopropyl-carbamic acid 2-[5-(2,6-diethyl-phenyl)-1-(4-isopropyl-phenyl)-1H-pyrrolo[2,3-C]pyridin-3-ylmethyl]-pentyl ester

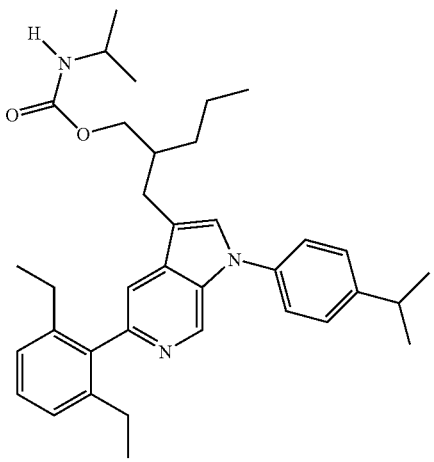

Step 1. Preparation of 2-[1-[5-(2,6-Diethyl-phenyl)-1-(4-isopropyl-phenyl)-1H-pyrrolo[2,3-c]pyridin-3-yl]-meth-(E)-ylidene]-pentanoic acid ethyl ester To a solution of 2-(diethoxy-phosphoryl)-pentanoic acid ethyl ester (80.5 mg, 0.3 mmol) in THF (4 mL) at 0° C., NaH (60 wt % suspension in mineral oil, 14.5 mg, 0.37 mmol) is added, and the mixture is stirred for 1 h at room temperature, The mixture is cooled to 0° C., and a solution of 5-(2,6-dimethyl-phenyl)-1-(4-isopropyl-phenyl)-1H-pyrrolo[2,3-c]pyridine-3-carbaldehyde (100 mg, 0.25 mmol) (example 3. step 3.) in THF (1.5 mL) is added. The mixture is stirred for 3 h at room temperature. A saturated aqueous NH$_4$Cl solution (4 mL) is added to the reaction. THF is evaporated under reduced pressure, and the product is extracted with EtOAc. The combined organic extracts are washed with brine, dried (Na$_2$SO$_4$), and concentrated under reduced pressure. Chromatography of the residue on silica gel (hexane-EtOAc, 1:3) affords 2-[1-[5-(2,6-Diethyl-phenyl)-1-(4-isopropyl-phenyl)-1H-pyrrolo[2,3-c]pyridin-3-yl]-meth-(E)-ylidene]-pentanoic acid ethyl ester as colorless oil.

Step 2. Preparation of 2-[5-(2,6-diethyl-phenyl)-1-(4-isopropyl-phenyl)-1H-pyrrolo[2,3-c]pyridin-3-ylmethyl]-pentanoic acid ethyl ester A mixture of (2-[1-[5-(2,6-diethyl-phenyl)-1-(4-isopropyl-phenyl)-1H-pyrrolo[2,3-c]pyridin-3-yl]-meth-(E)-ylidene]-pentanoic acid ethyl ester (120 mg, 0.23 mmol), 10% Pd/C (20 mg), and EtOH (4 mL) is stirred under hydrogen (1 atm) for 18 h at room temperature. The mixture is filtered over celite and concentrated under reduced pressure to afford 2-[5-(2,6-diethyl-phenyl)-1-(4-isopropyl-phenyl)-1H-pyrrolo[2,3-c]pyridin-3-ylmethyl]-pentanoic acid ethyl ester as colorless oil.

Step 3. Preparation of 2-[5-(2,6-diethyl-phenyl)-1-(4-isopropyl-phenyl)-1H-pyrrolo[2,3-c]pyridin-3-ylmethyl]-pentan-1-ol To a solution of 2-[5-(2,6-dimethyl-phenyl)-1-(4-isopropyl-phenyl)-1H-pyrrolo[2,3-c]pyridin-3-ylmethyl]-pentanoic acid ethyl ester (120 mg, 0.23 mmol) at −78° C., DIBAL (1M sol in toluene, 1.0 mL, 1.0 mmol) is added, and the mixture is stirred for 3 h at −78° C. The temperature of the mixture is allowed to gradually warm up to room temperature. To the mixture, a saturated aqueous Rochelle's salt solution (10 mL) is added, and the resultant suspension is stirred for 2 h at room temperature. The organic phase is separated, and the aqueous portion is extracted with DCM. The combined organic extracts are washed with brine and dried over Na$_2$SO$_4$. The solvent is removed under reduced pressure, and the residue purified by chromatography on silica gel (hexane-EtOAc, 1:1) to afford 2-[5-(2,6-diethyl-phenyl)-1-(4-isopropyl-phenyl)-1H-pyrrolo[2,3-c]pyridin-3-ylmethyl]-pentan-1-ol as colorless oil.

Step 4. Preparation of the Titled Compound

To a solution of 2-[5-(2,6-diethyl-phenyl)-1-(4-isopropyl-phenyl)-1H-pyrrolo[2,3-c]pyridin-3-ylmethyl]-pentan-1-ol (100 mg, 0.20 mmol) in DCM (3 mL), DMAP (1 mg), Et$_3$N (60 μL, 0.42 mmol), and isopropyl isocyanate (30 μL, 0.3 mmol) are added, and the mixture is stirred for 18 h at room temperature. All volatiles are removed under reduced pressure, and the product is purified by chromatography on silica gel (EtOAc-hexane, 2:1) to afford isopropyl-carbamic acid 2-[5-(2,6-diethyl-phenyl)-1-(4-isopropyl-phenyl)-1H-pyrrolo[2,3-c]pyridin-3-ylmethyl]-pentyl ester as colorless oil: LCMS m/z 554.18 (2.71 min).

Example 21

Synthesis of 4-[5-(2,6-diethylphenyl)-1-indan-1-yl)-1H-pyrrolo[2,3-C]pyridin-3-yl]cyclohexanecarboxylic acid

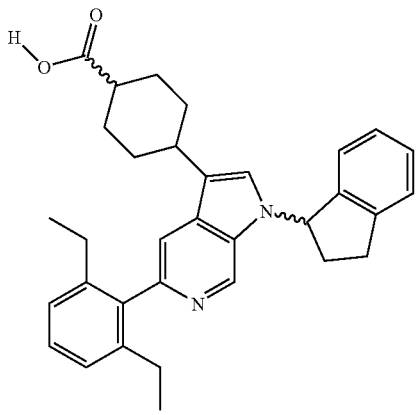

Step 1. Synthesis of 4-[5-(2,6-diethyl-phenyl)-1H-pyrrolo[2,3-c]pyridine-3-yl]-cyclohex-3-enecarboxylic acid A solution of 5-(2,6-diethyl-phenyl)-1H-pyrrolo[2,3-c]pyridine (200 mg, 0.8 mmol) in MeOH (5 mL) is added to a stirring solution of 4-oxo-cyclohexanecarboxylic acid methyl ester (204 mg, 1.2 mmol) and KOH (163 mg, 2.9 mmol) in MeOH (10 mL) at room temperature. The mixture is heated at reflux for 24 hours. The solvent is removed to dryness in vacuo. The residue is mixed with water and adjusted pH to 7. The mixture is extracted with $CH_2Cl_2$ (2×10 mL). The organic layer is washed with brine, dried, and evaporated under reduce pressure to give 120 mg of crude product. The crude product is used for next step without further purification.

Step 2. Synthesis of 4-[5-(2,6-diethyl-phenyl)-1H-pyrrolo[2,3-c]pyridine-3-yl]-cyclohexane-carboxylic acid 10% Pd/C (20 mg) is added to a solution of acid (120 mg, 0.32 mmol) in EtOH (5 mL) at room temperature. The mixture is under hydrogen pressure (40 psi) at room temperature for 10 hours. The mixture is filtered to remove Pd/C. The solvent is removed to give 108 mg of crude product and unreacted starting material. This crude mixture is used for next step without further purification.

Step 3. Synthesis of 4-[5-(2,6-diethyl-phenyl)-1H-pyrrolo[2,3-c]pyridine-3-yl]-cyclohexane-carboxylic acid methyl ester $MeSO_3H$ is added to a solution of crude mixture acid (108 mg) in MeOH (3 mL). The mixture is heated to reflux for 10 hours. The solvent is removed dryness in vacuo. This crude product is purified by prep-TLC and eluted with 50% EtOAc in hexane to give 47 mg of ester.

Step 4. Synthesis of 4-[5(2,6-diethyl-phenyl)-1-indan-1-yl-1H-pyrrolo[2,3-c]pyridine-3-yl]cyclohexanecarboxylic acid methyl ester NaH is added to a solution of ester (47 mg, 0.12 mmol) in DMF (1.5 mL) at room temperature and stirred for 1 hour. The chloride is added. The mixture is heated to 50° C. for 14 hours. The solvent is removed to dryness in vacuo. This crude product is purified by prep-TLC and eluted with 15% EtOAc in hexane to give 25 mg of product.

Step 5. Synthesis of 4-[5-(2,6-diethylphenyl)-1-indan-1-yl)-1H-pyrrolo[2,3-c]pyridin-3-yl]cyclohexanecarboxylic acid LiOH (5 mg, excess) is added to a solution of ester (25 mg, 0.05 mmol) in $THF/H_2O$ (1 mL/0.2 mL) at room temperature. The mixture is stirred at room temperature for 24 hours. The solvent is removed to dryness in vacuo. Water is added and pH is adjusted to 3, then neutralized to pH 7. The mixture is extracted with DCM (3×5 mL). The mixture is purified by prep-TLC to give 7.5 mg of less polar (major) product and 4.3 mg of polar (minor) product. $^1$H NMR ($CD_3OD$) less polar (major) 8.5 (s, 1H), 7.52-7.06 (m, 9H), 6.22 (t, 1H), 3.35-2.73 (m, 3H), 2.43-2.05 (m, 8H), 1.92-1.76 (m, 4H), 1.71-1.56 (m, 2H), 1.10-0.91.10 (t, 6H); polar (minor) 8.54 (s, 1H), 7.69 (s, 1H), 7.48-7.05 (m, 8H), 6.28 (t, 1H), 3.28-3.04 (m, 2H), 2.93-2.79 (m, 2H), 2.43-2.20 (m, 6H), 2.18-2.02 (m, 4H), 1.68-1.43 (m, 4H), 1.08-0.98 (t, 6H).

Example 22

Synthesis of (5-tert-butyl-2-methoxy-phenyl)-[5-(2,6-diethyl-phenyl)-pyrrolo-[2,3-C]pyridin-1-YL]-methanone

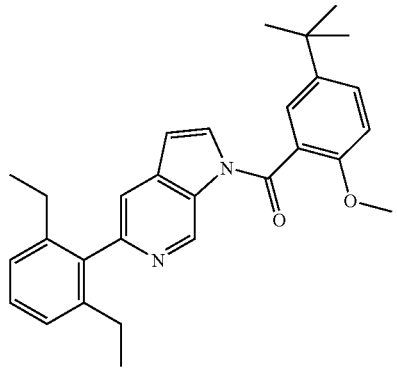

Thionyl chloride (0.3 mL, excess) is added dropwise to a solution of 5-tert-butyl-2-methoxy-benzoic acid (30 mg, 0.2 mmol) in $CH_2Cl_2$ (1 mL) at room temperature. The mixture is heated to 60° C. for 1.5 hours. The solvent is removed to dryness. A solution of 5-(2,6-diethyl-phenyl)-1H-pyrrolo[2,3-c]pyridine (10 mg, 0.04 mmol) and N,N-diisopropylethylamine (0.2 mL, excess) in THF (1 mL) is added to the residue. The mixture is stirred at room temperature for 16 hours. The solvent is removed to dryness in vacuo. The crude product is purified by PTLC and eluted with 20% EtOAc in hexane to give 12 mg of (5-tert-butyl-2-methoxy-phenyl)-[5-(2,6-diethyl-phenyl)-pyrrolo-[2,3-c]pyridine-1-yl]-methanone. $^1$H NMR (CDCl$_3$) 7.56-6.98 (m, 9H), 6.60-6.58 (d, 1H), 3.81 (s, 3H), 2.41-2.24 (q, 4H), 1.31 (s, 9H), 1.08-1.00 (t, 3H).

Example 23

Additional Pyrrolo-Pyridine and Pyrrolo-Pyrimidine Compounds

The compounds shown in Table I are prepared according to the procedures given in the above Schemes and further illustrated in the above Examples.

Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

LC/MS data is provided in the tables, along with retention time in minutes and a number (1, 2 or 3) indicating the method used. The LC/MS methods are as follows:

Method 1:

Analytical HPLC/MS instrumentation: Analyses are performed using a Waters 600 series pump (Waters Corporation, Milford, Mass.), a Waters 996 Diode Array Detector and a Gilson 215 auto-sampler (Gilson Inc, Middleton, Wis.), Micromass® LCT time-of-flight electrospray ionization mass analyzer. Data are acquired using MassLynx™ 4.0 software, with OpenLynx Global Server™, OpenLynx™, and AutoLynx™ processing.

Analytical HPLC conditions: 4.6×50 mm, Chromolith™ SpeedROD RP-18e column (Merck KGaA, Darmstadt, Germany); UV 10 spectra/sec, 220-340 nm summed; flow rate 6.0 mL/min; injection volume 1 µl;

Gradient conditions—mobile phase A is 95% water, 5% methanol with 0.05% TFA; mobile phase B is 95% methanol, 5% water with 0.025% TFA, and the gradient is 0-0.5 minutes 10-100% B, hold at 100% B to 1.2 minutes, return to 10% B at 1.21 minutes inject-to-inject cycle time is 2.15 minutes.

Analytical MS conditions: capillary voltage 3.5 kV; cone voltage 30V; desolvation and source temperature are 350° C. and 120° C., respectively; mass range 181-750 with a scan time of 0.22 seconds and an inter scan delay of 0.05 minutes.

Method 2:

HPLC instrumentation: Analyses are performed using a Waters 600 series pump (Waters Corporation, Milford, Mass.), a Waters 996 Diode Array Detector and a Gilson 215 autosampler (Gilson Inc, Middleton, Wis.). Data are acquired using MassLynx 4.0 software, with OpenLynx processing.

HPLC conditions: 4.6×50 mm, Chromolith SpeedRod column (Merck AEG); UV 5 spectra/sec, 220, 254 nm; flow rate 6.0 mL/min; injection volume 1-10 µl;

Gradient conditions—Mobile phase A 95% Water, 5% Methanol with 0.05% Formic acid;

Mobile phase B 95% Methanol, 5% Water with 0.025% Formic acid;

|  | Time(mins) | % B |
| --- | --- | --- |
| Gradient: | 0 | 5 |
|  | 0.01 | 5 |
|  | 1.0 | 100 |
|  | 2 | 100 |
|  | 2.1 | 5 |

MS instrumentation: LC-MS experiments are performed using a Waters ZMD II Mass Spectrometer.

MS conditions: Electrospray positive ionization; capillary voltage 3.5 kV; cone voltage 30V; desolvation and source temperature 250° C. and 100° C. respectively; mass range 120-800 with a scan time of 0.5 seconds and an inter scan delay of 0.1 mins.

Method 3:

HPLC instrumentation: Analyses are performed using a Waters 600 series pump (Waters Corp.), a Waters 996 Diode Array Detector and a Gilson 215 autosampler (Gilson Inc.). Data are acquired using MassLynx 4.0 software, with OpenLynx processing.

HPLC conditions: 4.6×50 mm, XTerra MS C18, 5 µm column (Waters Corp.); UV 10 spectra/sec, 220, 254 nm; flow rate 4.0 mL/min; injection volume 1-10 µl;

Gradient conditions—Mobile phase A 95% Water, 5% Methanol with 0.05% Formic acid;

Mobile phase B 95% Methanol, 5% Water with 0.025% Formic acid;

|  | Time(mins) | % B |
| --- | --- | --- |
| Gradient: | 0 | 5 |
|  | 0.01 | 5 |
|  | 2.0 | 100 |
|  | 3.50 | 100 |
|  | 3.51 | 5 |

MS instrumentation: LC-MS experiments are performed using a Waters ZMD II Mass Spectrometer.

MS conditions: Electrospray positive ionization; capillary voltage 3.5 kV; cone voltage 30V; desolvation and source temperature 250° C. and 100° C. respectively; mass range 120-800 with a scan time of 0.5 seconds and an inter scan delay of 0.1 mins.

The chemical groups shown in TABLE I contain letters $X_n$. These letters indicate a point of attachment of the group in the structure shown at the top of each table. In some instances the variables used to designate the positions of groups in the structures at the top of TABLE I may differ from the variables used to describe these positions in similar structures shown elsewhere in the application.

TABLE I

| Cmpd # | Name | Ar | Q | W | $R_1$ | $R_9$ | LC/MS Ret. Time (min.) | LC/MS M+1 | LC/MS Mass | LC/MS Method |
|---|---|---|---|---|---|---|---|---|---|---|
| 101 | 5-(2,6-diethylphenyl)-1-(1-ethylpropyl)-1H-pyrrolo[2,3-c]pyridine | 2,6-diethylphenyl ($X_1$) | 1-ethylpropyl ($X_2$) | H | H | H | 1.18 | 321.2 | 320.5 | 1 |
| 102 | 5-(2,6-diethylphenyl)-1-(1-phenylethyl)-1H-pyrrolo[2,3-c]pyridine | 2,6-diethylphenyl ($X_1$) | 1-phenylethyl ($X_2$) | H | H | H | 1.18 | 355.2 | 354.5 | 1 |
| 103 | 5-(2,6-diethylphenyl)-1-(4-methylbenzyl)-1H-pyrrolo[2,3-c]pyridine | 2,6-diethylphenyl ($X_1$) | 4-methylbenzyl ($X_2$) | H | H | H | 1.2 | 355.2 | 354.5 | 1 |
| 104 | 5-(2,6-diethylphenyl)-1-(2-methoxybenzyl)-1H-pyrrolo[2,3-c]pyridine | 2,6-diethylphenyl ($X_1$) | 2-methoxybenzyl ($X_2$) | H | H | H | 1.17 | 371.2 | 370.5 | 1 |
| 105 | 5-(2,6-diethylphenyl)-1-(3-methoxybenzyl)-1H-pyrrolo[2,3-c]pyridine | 2,6-diethylphenyl ($X_1$) | 3-methoxybenzyl ($X_2$) | H | H | H | 1.19 | 371.2 | 370.5 | 1 |
| 106 | 5-(2,6-diethylphenyl)-1-(4-methoxybenzyl)-1H-pyrrolo[2,3-c]pyridine | 2,6-diethylphenyl ($X_1$) | 4-methoxybenzyl ($X_2$) | H | H | H | 1.17 | 371.2 | 370.5 | 1 |

TABLE I-continued

| Cmpd # | Name | Ar | Q | W | $R_1$ | $R_9$ | LC/MS Ret. Time (min.) | LC/MS M + 1 | LC/MS Mass | LC/MS Method |
|---|---|---|---|---|---|---|---|---|---|---|
| 107 | 5-(2,6-diethylphenyl)-1-(1,2,3,4-tetrahydronaphthalen-1-yl)-1H-pyrrolo[2,3-c]pyridine | 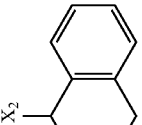 | 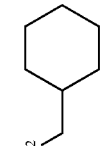 | H | H | H | 1.21 | 381.2 | 380.5 | 1 |
| 108 | 1-(cyclohexylmethyl)-5-(2,6-diethylphenyl)-1H-pyrrolo[2,3-c]pyridine | 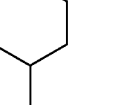 | 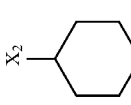 | H | H | H | 1.23 | 693.6 | 346.5 | 1 |
| 109 | 1-cyclohexyl-5-(2,6-diethylphenyl)-1H-pyrrolo[2,3-c]pyridine | 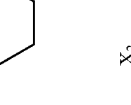 | 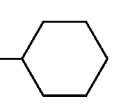 | H | H | H | 1.52 | 333.5 | 332.5 | 2 |
| 110 | 5-(2,6-diethylphenyl)-1-(7-methoxy-1,2,3,4-tetrahydronaphthalen-1-yl)-1H-pyrrolo[2,3-c]pyridine | 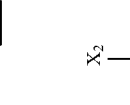 | 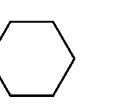 | H | H | H | 1.21 | 411.2 | 410.6 | 1 |
| 111 | 5-(2,6-diethylphenyl)-1-(2,3-dihydro-1H-inden-1-yl)-1H-pyrrolo[2,3-c]pyridine | 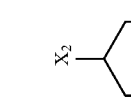 | 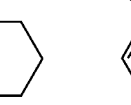 | H | H | H | 1.19 | 367.2 | 366.5 | 1 |
| 112 | 5-(2,6-diethylphenyl)-1-(6,7,8,9-tetrahydro-5H-benzo[7]annulen-5-yl)-1H-pyrrolo[2,3-c]pyridine | 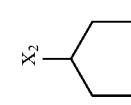 | 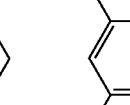 | H | H | H | 1.22 | 396.3 | 394.6 | 1 |

TABLE I-continued

| Cmpd # | Name | Ar | Q | W | R₁ | R₉ | LC/MS Ret. Time (min.) | LC/MS M+1 | LC/MS Mass | LC/MS Method |
|---|---|---|---|---|---|---|---|---|---|---|
| 113 | 5-(2,6-diethylphenyl)-1-(6-methoxy-2,3-dihydro-1H-inden-1-yl)-1H-pyrrolo[2,3-c]pyridine | 2,6-diethylphenyl (X₁) | 6-methoxy-2,3-dihydro-1H-inden-1-yl (X₂) | H | H | H | 1.55 | 397.4 | 396.5 | 2 |
| 114 | 5-(2,6-diethylphenyl)-1-(5-fluoro-2,3-dihydro-1H-inden-1-yl)-1H-pyrrolo[2,3-c]pyridine | 2,6-diethylphenyl (X₁) | 5-fluoro-2,3-dihydro-1H-inden-1-yl (X₂) | H | H | H | 1.54 | 385.4 | 384.5 | 2 |
| 115 | 5-(2,6-diethylphenyl)-1-[3-(trifluoromethyl)pyridin-2-yl]-1H-pyrrolo[2,3-c]pyridine | 2,6-diethylphenyl (X₁) | 3-(trifluoromethyl)pyridin-2-yl (X₂) | H | H | H | 1.18 | 396.2 | 395.5 | 1 |
| 116 | 2-[5-(2,6-diethylphenyl)-1H-pyrrolo[2,3-c]pyridin-1-yl]nicotinonitrile | 2,6-diethylphenyl (X₁) | 3-cyanopyridin-2-yl (X₂) | H | H | H | 1.14 | 353.2 | 352.4 | 1 |
| 117 | 1-(3-chloropyridin-2-yl)-5-(2,6-diethylphenyl)-1H-pyrrolo[2,3-c]pyridine | 2,6-diethylphenyl (X₁) | 3-chloropyridin-2-yl (X₂) | H | H | H | 1.16 | 362.2 | 361.9 | 1 |
| 118 | 5-(2,6-diethylphenyl)-1-[5-(trifluoromethyl)pyridin-2-yl]-1H-pyrrolo[2,3-c]pyridine | 2,6-diethylphenyl (X₁) | 5-(trifluoromethyl)pyridin-2-yl (X₂) | H | H | H | 1.19 | 396.2 | 395.4 | 1 |

TABLE I-continued

| Cmpd # | Name | Ar | Q | W | $R_1$ | $R_9$ | LC/MS Ret. Time (min.) | LC/MS M+1 | LC/MS Mass | LC/MS Method |
|---|---|---|---|---|---|---|---|---|---|---|
| 119 | 3-bromo-5-(2,6-diethylphenyl)-1-(1-propylbutyl)-1H-pyrrolo[2,3-c]pyridine | 2,6-diethylphenyl with $X_1$ | 1-propylbutyl with $X_2$ | Br | H | H | 1.28 | 427.2 | 427.4 | 1 |
| 120 | 5-(2,6-diethylphenyl)-1-(1-propylbutyl)-1H-pyrrolo[2,3-c]pyridine 6-oxide | 2,6-diethylphenyl with $X_1$ | 1-propylbutyl with $X_2$ | H | H | H | 1.29 | 365.3 | 364.5 | 1 |
| 121 | 3-[5-(2,6-diethylphenyl)-1H-pyrrolo[2,3-c]pyridin-1-yl]benzonitrile | 2,6-diethylphenyl with $X_1$ | 3-CN-phenyl with $X_2$ | H | H | H | | | 351.5 | |
| 122 | 4-[5-(2,6-diethylphenyl)-1H-pyrrolo[2,3-c]pyridin-1-yl]benzonitrile | 2,6-diethylphenyl with $X_1$ | 4-CN-phenyl with $X_2$ | H | H | H | 1.14 | 352.2 | 351.5 | 1 |
| 123 | 5-(2,6-diethylphenyl)-1-[4-(trifluoromethyl)phenyl]-1H-pyrrolo[2,3-c]pyridine | 2,6-diethylphenyl with $X_1$ | 4-CF$_3$-phenyl with $X_2$ | H | H | H | 1.19 | 395.2 | 394.4 | 1 |
| 124 | 1-{4-[5-(2,6-diethylphenyl)-1H-pyrrolo[2,3-c]pyridin-1-yl]phenyl}ethanone | 2,6-diethylphenyl with $X_1$ | 4-acetyl-phenyl with $X_2$ | H | H | H | 1.15 | 369.2 | 368.5 | 1 |

TABLE I-continued

| Cmpd # | Name | Ar | Q | W | R₁ | R₉ | LC/MS Ret. Time (min.) | LC/MS M + 1 | LC/MS Mass | LC/MS Method |
|---|---|---|---|---|---|---|---|---|---|---|
| 125 | 5-(2,6-diethylphenyl)-1-(4-methoxyphenyl)-1H-pyrrolo[2,3-c]pyridine | 2,6-diethylphenyl (X₁) | 4-methoxyphenyl (X₂) | H | H | H | 1.18 | 357.1 | 356.5 | 1 |
| 126 | 5-(2,6-diethylphenyl)-1-(3-methoxyphenyl)-1H-pyrrolo[2,3-c]pyridine | 2,6-diethylphenyl (X₁) | 3-methoxyphenyl (X₂) | H | H | H | 1.18 | 357.2 | 356.5 | 1 |
| 127 | 5-(2,6-diethylphenyl)-1-(3-isopropylphenyl)-1H-pyrrolo[2,3-c]pyridine | 2,6-diethylphenyl (X₁) | 3-isopropylphenyl (X₂) | H | H | H | 1.18 | 369.2 | 368.5 | 1 |
| 128 | 1-(4-tert-butylphenyl)-5-(2,6-diethylphenyl)-1H-pyrrolo[2,3-c]pyridine | 2,6-diethylphenyl (X₁) | 4-tert-butylphenyl (X₂) | H | H | H | 1.24 | 383.2 | 385.5 | 1 |
| 129 | 5-(2,6-diethylphenyl)-1-[4-(trifluoromethoxy)phenyl]-1H-pyrrolo[2,3-c]pyridine | 2,6-diethylphenyl (X₁) | 4-(trifluoromethoxy)phenyl (X₂) | H | H | H | 1.57 | 411.4 | 410.4 | 2 |
| 130 | 1-(1,3-benzodioxol-5-yl)-5-(2,6-diethylphenyl)-1H-pyrrolo[2,3-c]pyridine | 2,6-diethylphenyl (X₁) | 1,3-benzodioxol-5-yl (X₂) | H | H | H | 1.18 | 371.2 | 370.5 | 1 |

TABLE I-continued

| Cmpd # | Name | Ar | Q | W | R$_1$ | R$_9$ | LC/MS Ret. Time (min.) | LC/MS M+1 | LC/MS Mass | LC/MS Method |
|---|---|---|---|---|---|---|---|---|---|---|
| 131 | 5-(2,6-diethylphenyl)-1-(2-ethylphenyl)-1H-pyrrolo[2,3-c]pyridine | 2,6-diethylphenyl (X$_1$) | 2-ethylphenyl (X$_2$) | H | H | H | 1.53 | 355.5 | 354.5 | 2 |
| 132 | 5-(2,6-diethylphenyl)-1-(2,4-dimethylphenyl)-1H-pyrrolo[2,3-c]pyridine | 2,6-diethylphenyl (X$_1$) | 2,4-dimethylphenyl (X$_2$) | H | H | H | 1.54 | 355.5 | 354.5 | 2 |
| 133 | 5-(2,6-diethylphenyl)-1-(2,3-dimethylphenyl)-1H-pyrrolo[2,3-c]pyridine | 2,6-diethylphenyl (X$_1$) | 2,3-dimethylphenyl (X$_2$) | H | H | H | 1.19 | 355.2 | 354.5 | 1 |
| 134 | 5-(2,6-diethylphenyl)-3-methyl-1-(1-propylbutyl)-1H-pyrrolo[2,3-c]pyridine | 2,6-diethylphenyl (X$_1$) | 1-propylbutyl (X$_2$) | CH$_3$ | H | H | 1.24 | 363.2 | 362.6 | 1 |
| 135 | 5-(2,6-diethylphenyl)-1-(4-ethoxyphenyl)-1H-pyrrolo[2,3-c]pyridine | 2,6-diethylphenyl (X$_1$) | 4-ethoxyphenyl (X$_2$) | H | H | H | 1.53 | 371.4 | 370.5 | 2 |
| 136 | 5-(2,6-diethylphenyl)-1-(4-methyl-2,3-dihydro-1H-inden-1-yl)-1H-pyrrolo[2,3-c]pyridine | 2,6-diethylphenyl (X$_1$) | 4-methyl-2,3-dihydro-1H-inden-1-yl (X$_2$) | H | H | H | 1.23 | 381.2 | 380.5 | 1 |

TABLE I-continued

| Cmpd # | Name | Ar | Q | W | R1 | R9 | LC/MS Ret. Time (min.) | LC/MS M+1 | LC/MS Mass | LC/MS Method |
|---|---|---|---|---|---|---|---|---|---|---|
| 137 | 1-benzoyl-5-(2,6-diethylphenyl)-1H-pyrrolo[2,3-c]pyridine | 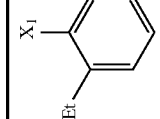 | 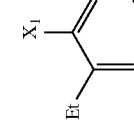 | H | H | H | 1.17 | 355.2 | 354.5 | 1 |
| 138 | 5-(2,6-diethylphenyl)-3-(1-methylpiperidin-4-yl)-1-(1-propylbutyl)-1H-pyrrolo[2,3-c]pyridine | 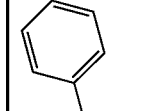 | 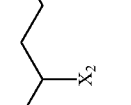 |  | H | H | 1.09 | 446.4 | 445.7 | 1 |
| 139 | 5-(2,6-diethylphenyl)-3-(1,4-dioxaspiro[4.5]dec-8-yl)-1-(1-propylbutyl)-1H-pyrrolo[2,3-c]pyridine | 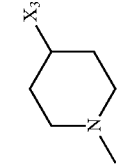 | |  | H | H | 1.27 | 489.4 | 488.7 | 1 |
| 140 | 5-(2,6-diethylphenyl)-1-(2,3-dihydro-1H-inden-2-yl)-1H-pyrrolo[2,3-c]pyridine |  |  | H | H | H | 1.55 | 367.4 | 366.5 | 2 |
| 141 | 3-(1-acetylpiperidin-4-yl)-5-(2,6-diethylphenyl)-1-(1-propylbutyl)-1H-pyrrolo[2,3-c]pyridine |  | |  | H | H | 1.19 | 474.3 | 473.7 | 1 |
| 142 | 5-(2,6-diethylphenyl)-3-[1-(methylsulfonyl)piperidin-4-yl]-1-(1-propylbutyl)-1H-pyrrolo[2,3-c]pyridine |  | | | H | H | 1.19 | 510.3 | 509.8 | 1 |

TABLE 1-continued

| Cmpd # | Name | Ar | Q | W | R₁ | R₉ | LC/MS Ret. Time (min.) | LC/MS M + 1 | LC/MS Mass | LC/MS Method |
|---|---|---|---|---|---|---|---|---|---|---|
| 143 | 4-[5-(2,6-diethylphenyl)-1-(1-propylbutyl)-1H-pyrrolo[2,3-c]pyridin-3-yl]benzoic acid | 2,6-diethylphenyl with X₁ | 1-propylbutyl with X₂ | 4-X₃-benzoic acid | H | H | 2.47 | 469.3 | 468.6 | 2 |
| 144 | 3-[5-(2,6-diethylphenyl)-1-(1-propylbutyl)-1H-pyrrolo[2,3-c]pyridin-3-yl]benzoic acid | 2,6-diethylphenyl with X₁ | 1-propylbutyl with X₂ | 3-X₃-benzoic acid | H | H | 2.48 | 469.3 | 468.6 | 2 |
| 145 | methyl 5-(2,6-diethylphenyl)-1-(1-propylbutyl)-1H-pyrrolo[2,3-c]pyridine-3-carboxylate | 2,6-diethylphenyl with X₁ | 1-propylbutyl with X₂ | methyl ester with X₃ | H | H | 1.24 | 408.4 | 406.6 | 1 |
| 146 | tert-butyl 3-[5-(2,6-diethylphenyl)-1-(1-propylbutyl)-1H-pyrrolo[2,3-c]pyridin-3-yl]propanoate | 2,6-diethylphenyl with X₁ | 1-propylbutyl with X₂ | tert-butyl propanoate with X₃ | H | H | 1.28 | 478.5 | 476.7 | 1 |
| 147 | 1-(4-tert-butylbenzoyl)-5-(2,6-diethylphenyl)-1H-pyrrolo[2,3-c]pyridine | 2,6-diethylphenyl with X₁ | 4-tert-butylbenzoyl with X₂ | H | H | H | 1.25 | 411.3 | 410.6 | 1 |
| 148 | 5-(2,6-diethylphenyl)-1-(6-methoxypyridin-3-yl)-1H-pyrrolo[2,3-c]pyridine | 2,6-diethylphenyl with X₁ | 6-methoxypyridin-3-yl with X₂ | H | H | H | 1.46 | 358.4 | 357.5 | 2 |

TABLE I-continued

| Cmpd # | Name | Ar | Q | W | $R_1$ | $R_9$ | LC/MS Ret. Time (min.) | LC/MS M+1 | LC/MS Mass | LC/MS Method |
|---|---|---|---|---|---|---|---|---|---|---|
| 149 | 3-[5-(2,6-diethylphenyl)-1-(1-propylbutyl)-1H-pyrrolo[2,3-c]pyridin-3-yl]propanoic acid | 2,6-diethylphenyl ($X_1$) | 1-propylbutyl ($X_2$) | -CH$_2$CH$_2$C(O)OH ($X_3$) | H | H | 1.19 | 421.4 | 420.6 | 1 |
| 150 | 5-(2,6-diethylphenyl)-1-[2-methyl-5-(trifluoromethyl)benzyl]-1H-pyrrolo[2,3-c]pyridine | 2,6-diethylphenyl ($X_1$) | 2-methyl-5-(trifluoromethyl)benzyl ($X_2$) | H | H | H | 1.59 | 423.4 | 422.5 | 2 |
| 151 | 5-(2,6-diethylphenyl)-1-[2-fluoro-5-(trifluoromethyl)benzyl]-1H-pyrrolo[2,3-c]pyridine | 2,6-diethylphenyl ($X_1$) | 2-fluoro-5-(trifluoromethyl)benzyl ($X_2$) | H | H | H | 1.2 | 428.3 | 426.5 | 1 |
| 152 | 5-(2,6-diethylphenyl)-1-(1-propylbutyl)-1H-pyrrolo[2,3-c]pyridine-3-carboxylic acid | 2,6-diethylphenyl ($X_1$) | 1-propylbutyl ($X_2$) | -C(O)OH ($X_3$) | H | H | 2.36 | 393.3 | 392.5 | 2 |
| 153 | 5-(2,6-diethylphenyl)-N-isobutyl-1-(1-propylbutyl)-1H-pyrrolo[2,3-c]pyridine-3-carboxamide | 2,6-diethylphenyl ($X_1$) | 1-propylbutyl ($X_2$) | -C(O)NH-isobutyl ($X_3$) | H | H | 2.48 | 448.4 | 447.7 | 2 |
| 154 | 3-[5-(2,6-diethylphenyl)-1-(1-propylbutyl)-1H-pyrrolo[2,3-c]pyridin-3-yl]-N,N-diethylpropanamide | 2,6-diethylphenyl ($X_1$) | 1-propylbutyl ($X_2$) | -CH$_2$CH$_2$C(O)N(Et)$_2$ ($X_3$) | H | H | 2.3 | 476.4 | 475.7 | 2 |

TABLE I-continued

| Cmpd # | Name | Ar | Q | W | R₁ | R₉ | LC/MS Ret. Time (min.) | LC/MS M+1 | LC/MS Mass | LC/MS Method |
|---|---|---|---|---|---|---|---|---|---|---|
| 155 | 3-[5-(2,6-diethylphenyl)-1-(1-propylbutyl)-1H-pyrrolo[2,3-c]pyridin-3-yl]-N-isobutylpropanamide | 2,6-diethylphenyl (X₁) | 1-propylbutyl (X₂) | isobutylamide propanoyl | H | H | 2.3 | 476.4 | 475.7 | 2 |
| 156 | 5-(2,6-diethylphenyl)-1-(5-ethylpyrimidin-2-yl)-1H-pyrrolo[2,3-c]pyridine | 2,6-diethylphenyl (X₁) | 5-ethylpyrimidin-2-yl (X₂) | H | H | H | 1.2 | 358.3 | 356.5 | 1 |
| 157 | 5-(2,6-diethylphenyl)-1-(3,5-dimethylphenyl)-1H-pyrrolo[2,3-c]pyridine | 2,6-diethylphenyl (X₁) | 3,5-dimethylphenyl (X₂) | H | H | H | 1.19 | 355.3 | 354.5 | 1 |
| 158 | 5-(2,6-diethylphenyl)-1-(4-propylphenyl)-1H-pyrrolo[2,3-c]pyridine | 2,6-diethylphenyl (X₁) | 4-propylphenyl (X₂) | H | H | H | 1.22 | 370.3 | 368.5 | 1 |
| 159 | 5-(2,6-diethylphenyl)-1-(6-methoxypyridazin-3-yl)-1H-pyrrolo[2,3-c]pyridine | 2,6-diethylphenyl (X₁) | 6-methoxypyridazin-3-yl (X₂) | H | H | H | 1.13 | 359.3 | 358.4 | 1 |
| 160 | 5-(2,6-diethylphenyl)-1-[4-(difluoromethoxy)phenyl]-1H-pyrrolo[2,3-c]pyridine | 2,6-diethylphenyl (X₁) | 4-(difluoromethoxy)phenyl (X₂) | H | H | H | 1.16 | 393.3 | 392.4 | 1 |

TABLE I-continued

| Cmpd # | Name | Ar | Q | W | $R_1$ | $R_9$ | LC/MS Ret. Time (min.) | LC/MS M+1 | LC/MS Mass | LC/MS Method |
|---|---|---|---|---|---|---|---|---|---|---|
| 161 | 1-(3-chlorophenyl)-5-(2,6-diethylphenyl)-1H-pyrrolo[2,3-c]pyridine | 2,6-diethylphenyl ($X_1$) | 3-chlorophenyl ($X_2$) | H | H | H | 1.18 | 361.2 | 360.9 | 1 |
| 162 | 5-(2,6-diethylphenyl)-1-[4-(methylsulfonyl)phenyl]-1H-pyrrolo[2,3-c]pyridine | 2,6-diethylphenyl ($X_1$) | 4-(methylsulfonyl)phenyl ($X_2$) | H | H | H | | 405.3 | 404.5 | 1 |
| 163 | 5-(2,6-diethylphenyl)-1-[(2-methyl-1-naphthyl)methyl]-1H-pyrrolo[2,3-c]pyridine | 2,6-diethylphenyl ($X_1$) | (2-methyl-1-naphthyl)methyl ($X_2$) | H | H | H | 1.23 | 405.3 | 404.6 | 1 |
| 164 | 1-(3-bromobenzyl)-5-(2,6-diethylphenyl)-1H-pyrrolo[2,3-c]pyridine | 2,6-diethylphenyl ($X_1$) | 3-bromobenzyl ($X_2$) | H | H | H | 1.21 | 419.2 | 419.4 | 1 |
| 165 | 1-(2-chloro-6-fluorobenzyl)-5-(2,6-diethylphenyl)-1H-pyrrolo[2,3-c]pyridine | 2,6-diethylphenyl ($X_1$) | 2-chloro-6-fluorobenzyl ($X_2$) | H | H | H | 1.19 | 395.3 | 392.9 | 1 |
| 166 | 5-(2,6-diethylphenyl)-1-(4-isopropylbenzyl)-1H-pyrrolo[2,3-c]pyridine | 2,6-diethylphenyl ($X_1$) | 4-isopropylbenzyl ($X_2$) | H | H | H | 1.23 | 384.4 | 382.5 | 1 |

TABLE I-continued

| Cmpd # | Name | Ar | Q | W | R₁ | R₉ | LC/MS Ret. Time (min.) | LC/MS M+1 | LC/MS Mass | LC/MS Method |
|---|---|---|---|---|---|---|---|---|---|---|
| 167 | 1-[(5-chloro-1,3-benzodioxol-4-yl)methyl]-5-(2,6-diethylphenyl)-1H-pyrrolo[2,3-c]pyridine | 2,6-diethylphenyl (X₁) | 5-chloro-1,3-benzodioxol-4-ylmethyl (X₂) | H | H | H | 1.2 | 421.3 | 418.9 | 1 |
| 168 | 5-(2,6-diethylphenyl)-1-(2,5-dimethylbenzyl)-1H-pyrrolo[2,3-c]pyridine | 2,6-diethylphenyl (X₁) | 2,5-dimethylbenzyl (X₂) | H | H | H | 1.21 | 369.3 | 368.5 | 1 |
| 169 | 5-(2,6-diethylphenyl)-1-(3,5-dimethylbenzyl)-1H-pyrrolo[2,3-c]pyridine | 2,6-diethylphenyl (X₁) | 3,5-dimethylbenzyl (X₂) | H | H | H | 1.22 | 369.3 | 368.5 | 1 |
| 170 | 5-(2,6-diethylphenyl)-1-(mesitylmethyl)-1H-pyrrolo[2,3-c]pyridine | 2,6-diethylphenyl (X₁) | mesitylmethyl (X₂) | H | H | H | 1.25 | 383.3 | 382.5 | 1 |
| 171 | 5-(2,6-diethylphenyl)-1-[4-(trifluoromethoxy)benzyl]-1H-pyrrolo[2,3-c]pyridine | 2,6-diethylphenyl (X₁) | 4-(trifluoromethoxy)benzyl (X₂) | H | H | H | 1.22 | 425.3 | 424.5 | 1 |
| 172 | 5-(2,6-diethylphenyl)-1-[3-(trifluoromethyl)benzyl]-1H-pyrrolo[2,3-c]pyridine | 2,6-diethylphenyl (X₁) | 3-(trifluoromethyl)benzyl (X₂) | H | H | H | 1.2 | 409.3 | 408.5 | 1 |

TABLE I-continued

| Cmpd # | Name | Ar | Q | W | $R_1$ | $R_9$ | LC/MS Ret. Time (min.) | LC/MS M+1 | LC/MS Mass | LC/MS Method |
|---|---|---|---|---|---|---|---|---|---|---|
| 173 | 5-(2,6-diethylphenyl)-1-[4-(trifluoromethyl)benzyl]-1H-pyrrolo[2,3-c]pyridine | 2,6-diethylphenyl ($X_1$) | 4-(trifluoromethyl)benzyl ($X_2$) | H | H | H | 1.22 | 409.3 | 408.5 | 1 |
| 174 | 5-(2,6-diethylphenyl)-1-[2-(trifluoromethyl)benzyl]-1H-pyrrolo[2,3-c]pyridine | 2,6-diethylphenyl ($X_1$) | 2-(trifluoromethyl)benzyl ($X_2$) | H | H | H | 1.2 | 409.3 | 408.5 | 1 |
| 175 | 2-{4-[5-(2,6-diethylphenyl)-1H-pyrrolo[2,3-c]pyridin-1-yl]phenyl}propan-2-ol | 2,6-diethylphenyl ($X_1$) | 4-(2-hydroxypropan-2-yl)phenyl ($X_2$) | H | H | H | 1.16 | 385.3 | 384.5 | 1 |
| 176 | methyl 2-{4-[5-(2,6-diethylphenyl)-1H-pyrrolo[2,3-c]pyridin-1-yl]phenyl}-2-methylpropanoate | 2,6-diethylphenyl ($X_1$) | methyl 2-methylpropanoate-phenyl ($X_2$) | H | H | H | 1.18 | 427.3 | 426.6 | 1 |
| 177 | 2-{4-[5-(2,6-diethylphenyl)-1H-pyrrolo[2,3-c]pyridin-1-yl]phenyl}-2-methylpropanoic acid | 2,6-diethylphenyl ($X_1$) | 2-methylpropanoic acid-phenyl ($X_2$) | H | H | H | 1.18 | 413.3 | 412.5 | 1 |
| 178 | 1-(4-cyclohexylphenyl)-5-(2,6-diethylphenyl)-1H-pyrrolo[2,3-c]pyridine | 2,6-diethylphenyl ($X_1$) | 4-cyclohexylphenyl ($X_2$) | H | H | H | 1.27 | 410.3 | 408.6 | 1 |

TABLE I-continued

| Cmpd # | Name | Ar | Q | W | R$_1$ | R$_9$ | LC/MS Ret. Time (min.) | LC/MS M + 1 | LC/MS Mass | LC/MS Method |
|---|---|---|---|---|---|---|---|---|---|---|
| 179 | 1-(4-bromophenyl)-5-(2,6-diethylphenyl)-1H-pyrrolo[2,3-c]pyridine | 2,6-diethylphenyl (X$_1$) | 4-bromophenyl (X$_2$) | H | H | H | 1.18 | 405.2 | 405.3 | 1 |
| 180 | 1-(2,5-dichlorobenzyl)-5-(2,6-diethylphenyl)-1H-pyrrolo[2,3-c]pyridine | 2,6-diethylphenyl (X$_1$) | 2,5-dichlorobenzyl (X$_2$) | H | H | H | 1.21 | 411.2 | 409.4 | 1 |
| 181 | 1-(2,4-dichlorobenzyl)-5-(2,6-diethylphenyl)-1H-pyrrolo[2,3-c]pyridine | 2,6-diethylphenyl (X$_1$) | 2,4-dichlorobenzyl (X$_2$) | H | H | H | 1.22 | 409.2 | 409.4 | 1 |
| 182 | 1-(3-{[5-(2,6-diethylphenyl)-1H-pyrrolo[2,3-c]pyridin-1-yl]methyl}-4-methoxyphenyl)ethanone | 2,6-diethylphenyl (X$_1$) | 3-(methyl)-4-methoxyphenyl acetyl (X$_2$) | H | H | H | 1.17 | 413.3 | 412.5 | 1 |
| 183 | (2E)-3-[5-(2,6-diethylphenyl)-1-(4-isopropylphenyl)-1H-pyrrolo[2,3-c]pyridin-3-yl]prop-2-en-1-ol | 2,6-diethylphenyl (X$_1$) | 4-isopropylphenyl (X$_2$) | HO-CH=CH-CH$_2$ (X$_3$) | H | H | 2.4 | 425.3 | 424.6 | 2 |

TABLE I-continued

| Cmpd # | Name | Ar | Q | W | $R_1$ | $R_9$ | LC/MS Ret. Time (min.) | LC/MS M + 1 | LC/MS Mass | LC/MS Method |
|---|---|---|---|---|---|---|---|---|---|---|
| 184 | 4-{[5-(2,6-diethylphenyl)-1H-pyrrolo[2,3-c]pyridin-1-yl]carbonyl}-3-methoxy-2-phenylquinoline | 2,6-diethylphenyl ($X_1$) | 2-methoxy-3-phenylnaphthalene-1-carbonyl ($X_1$) | H | H | H | 1.29 | 512.3 | 511.6 | 1 |
| 185 | 1-(3-bromo-2,6-dimethoxybenzoyl)-5-(2,6-diethylphenyl)-1H-pyrrolo[2,3-c]pyridine | 2,6-diethylphenyl ($X_1$) | 3-bromo-2,6-dimethoxybenzoyl ($X_1$) | H | H | H | 1.68 | 493.1 | 493.4 | |
| 186 | 5-(2,6-diethylphenyl)-1-(2,5-dimethoxybenzoyl)-1H-pyrrolo[2,3-c]pyridine | 2,6-diethylphenyl ($X_1$) | 2,5-dimethoxybenzoyl ($X_1$) | H | H | H | 1.18 | 415.2 | 414.5 | 1 |
| 187 | 5-(2,6-diethylphenyl)-1-(2,5-dimethylbenzoyl)-1H-pyrrolo[2,3-c]pyridine | 2,6-diethylphenyl ($X_1$) | 2,5-dimethylbenzoyl ($X_1$) | H | H | H | 1.21 | 383.2 | 382.5 | 1 |
| 188 | 1-[2,5-bis(trifluoromethyl)benzyl]-5-(2,6-diethylphenyl)-1H-pyrrolo[2,3-c]pyridine | 2,6-diethylphenyl ($X_1$) | 2,5-bis(trifluoromethyl)benzyl ($X_2$) | H | H | H | 1.22 | 477.2 | 476.5 | 1 |

TABLE I-continued

| Cmpd # | Name | Ar | Q | W | $R_1$ | $R_9$ | LC/MS Ret. Time (min.) | LC/MS M+1 | LC/MS Mass | LC/MS Method |
|---|---|---|---|---|---|---|---|---|---|---|
| 189 | 1-[5-chloro-2-(trifluoromethyl)benzyl]-5-(2,6-diethylphenyl)-1H-pyrrolo[2,3-c]pyridine | 2,6-diethylphenyl ($X_1$) | 5-CF$_3$, 2-Cl benzyl ($X_2$) | H | H | H | 1.21 | 445.2 | 442.9 | 1 |
| 190 | 5-(2,6-diethylphenyl)-1-(2,3-dimethoxybenzyl)-1H-pyrrolo[2,3-c]pyridine | 2,6-diethylphenyl ($X_1$) | 2,3-dimethoxybenzyl ($X_2$) | Br | H | H | 1.18 | 401.3 | 400.5 | 1 |
| 191 | 3-bromo-5-(2,6-diethylphenyl)-1-(4-isopropylphenyl)-1H-pyrrolo[2,3-c]pyridine | 2,6-diethylphenyl ($X_1$) | 4-isopropylphenyl ($X_2$) | H | H | H | 1.29 | 449.2 | 447.4 | 1 |
| 192 | 5-(2,6-diethylphenyl)-1-[5-fluoro-2-(trifluoromethyl)benzyl]-1H-pyrrolo[2,3-c]pyridine | 2,6-diethylphenyl ($X_1$) | 5-F, 2-CF$_3$ benzyl ($X_2$) | H | H | H | 1.19 | 427.3 | 426.5 | 1 |
| 193 | 5-(2,6-diethylphenyl)-1-(2-phenylethyl)-1H-pyrrolo[2,3-c]pyridine | 2,6-diethylphenyl ($X_1$) | 2-phenylethyl ($X_2$) | H | H | H | 1.19 | 356.3 | 354.5 | 1 |
| 194 | 4-[5-(2,6-diethylphenyl)-1H-pyrrolo[2,3-c]pyridin-1-yl]phenol | 2,6-diethylphenyl ($X_1$) | 4-hydroxyphenyl ($X_2$) | H | H | H | 1.15 | 343.3 | 342.4 | 1 |

TABLE I-continued

| Cmpd # | Name | Ar | Q | W | $R_1$ | $R_9$ | LC/MS Ret. Time (min.) | LC/MS M + 1 | LC/MS Mass | LC/MS Method |
|---|---|---|---|---|---|---|---|---|---|---|
| 195 | 1-[4-(benzyloxy)phenyl]-5-(2,6-diethylphenyl)-1H-pyrrolo[2,3-c]pyridine | 2,6-diethylphenyl ($X_1$) | 4-(benzyloxy)phenyl ($X_2$) | H | H | H | 1.23 | 434.4 | 432.6 | 1 |
| 196 | 2-{4-[5-(2,6-diethylphenyl)-1H-pyrrolo[2,3-c]pyridin-1-yl]phenoxy}-N,N-dimethylethanamine | 2,6-diethylphenyl ($X_1$) | 4-(2-dimethylaminoethoxy)phenyl ($X_2$) | H | H | H | 1.09 | 414.4 | 413.6 | 1 |
| 197 | 5-(2,6-diethylphenyl)-1-[4-(2-morpholin-4-ylethoxy)phenyl]-1H-pyrrolo[2,3-c]pyridine | 2,6-diethylphenyl ($X_1$) | 4-(2-morpholinoethoxy)phenyl ($X_2$) | H | H | H | 1.09 | 456.4 | 455.6 | 1 |
| 198 | 5-(2,6-diethylphenyl)-1-(4-isopropoxyphenyl)-1H-pyrrolo[2,3-c]pyridine | 2,6-diethylphenyl ($X_1$) | 4-isopropoxyphenyl ($X_2$) | H | H | H | 1.2 | 386.3 | 384.5 | 1 |
| 199 | 5-(2,6-diethylphenyl)-1-(5-isopropyl-2-methylphenyl)-1H-pyrrolo[2,3-c]pyridine | 2,6-diethylphenyl ($X_1$) | 5-isopropyl-2-methylphenyl ($X_2$) | H | H | H | 1.22 | 384.4 | 382.5 | 1 |
| 200 | 1-[5-(2,6-diethylphenyl)-1-(4-isopropylphenyl)-1H-pyrrolo[2,3-c]pyridin-3-yl]butan-1-ol | 2,6-diethylphenyl ($X_1$) | 4-isopropylphenyl ($X_2$) | 1-hydroxybutyl ($X_3$, OH) | H | H | 1.24 | 442.4 | 440.6 | 1 |

TABLE I-continued

| Cmpd # | Name | Ar | Q | W | R₁ | R₉ | LC/MS Ret. Time (min.) | LC/MS M+1 | LC/MS Mass | LC/MS Method |
|---|---|---|---|---|---|---|---|---|---|---|
| 201 | 1-[5-(2,6-diethylphenyl)-1-(4-isopropylphenyl)-1H-pyrrolo[2,3-c]pyridin-3-yl]ethanol | 2,6-diethylphenyl (X₁) | 4-isopropylphenyl (X₂) | CH(CH₃)OH (X₃) | H | H | 2.33 | 413.3 | 412.6 | 2 |
| 202 | 2-{[5-(2,6-diethylphenyl)-1H-pyrrolo[2,3-c]pyridin-1-yl]methyl}-3-ethyl-3H-imidazo[4,5-b]pyridine | 2,6-diethylphenyl (X₁) | 1-ethyl-imidazo[4,5-b]pyridin-2-ylmethyl (X₂) | H | H | H | 1.15 | 410.3 | 409.5 | 1 |
| 203 | 1-[5-(2,6-diethylphenyl)-1-(4-isopropylphenyl)-1H-pyrrolo[2,3-c]pyridin-3-yl]-2-methylpropan-1-ol | 2,6-diethylphenyl (X₁) | 4-isopropylphenyl (X₂) | CH(OH)CH(CH₃)₂ (X₃) | H | H | 1.24 | 441.4 | 440.6 | 1 |
| 204 | 7-chloro-5-(2,6-diethylphenyl)-1-(4-isopropylphenyl)-3,4-dimethyl-1H-pyrrolo[2,3-c]pyridine | 2,6-diethylphenyl (X₁) | 4-isopropylphenyl (X₂) | CH₃ (X₃) | Cl | CH₃ | 1.52 | 431.3 | 431.0 | 1 |
| 205 | 1-(4-tert-butylphenyl)-7-chloro-5-(2,6-diethylphenyl)-3,4-dimethyl-1H-pyrrolo[2,3-c]pyridine | 2,6-diethylphenyl (X₁) | 4-tert-butylphenyl (X₂) | CH₃ (X₃) | Cl | CH₃ | 1.53 | 445.3 | 445.0 | 1 |
| 206 | tert-butyl 2-[5-(2,6-diethylphenyl)-1-(4-isopropylphenyl)-1H-pyrrolo[2,3-c]pyridin-3-yl]-1H-pyrrole-1-carboxylate | 2,6-diethylphenyl (X₁) | 4-isopropylphenyl (X₂) | N-Boc-pyrrol-2-yl (X₃) | H | H | 1.33 | 534.4 | 533.7 | 1 |

TABLE I-continued

| Cmpd # | Name | Ar | Q | W | R₁ | R₉ | LC/MS Ret. Time (min.) | LC/MS M + 1 | LC/MS Mass | LC/MS Method |
|---|---|---|---|---|---|---|---|---|---|---|
| 207 | 3-butyl-5-(2,6-diethylphenyl)-1-(4-isopropylphenyl)-1H-pyrrolo[2,3-c]pyridine | 2,6-diethylphenyl (X₁) | 4-isopropylphenyl (X₂) | n-pentyl (X₃) | H | H | 1.3 | 425.4 | 424.6 | 1 |
| 208 | 3-((1Z)-but-1-en-1-yl]-5-(2,6-diethylphenyl)-1-(4-isopropylphenyl)-1H-pyrrolo[2,3-c]pyridine | 2,6-diethylphenyl (X₁) | 4-isopropylphenyl (X₂) | (Z)-but-1-enyl (X₃) | H | H | 2.83 | 423.4 | 422.6 | 2 |
| 209 | 1-[5-(2,6-diethylphenyl)-1-(4-isopropylphenyl)-1H-pyrrolo[2,3-c]pyridin-3-yl]-2-methylbutan-1-ol | 2,6-diethylphenyl (X₁) | 4-isopropylphenyl (X₂) | 2-methyl-1-hydroxybutyl (X₃) | H | H | 1.26 | 455.4 | 454.7 | 1 |
| 210 | 1-[5-(2,6-diethylphenyl)-1-(4-isopropylphenyl)-1H-pyrrolo[2,3-c]pyridin-3-yl]-3-methylbutan-1-one | 2,6-diethylphenyl (X₁) | 4-isopropylphenyl (X₂) | 3-methylbutanoyl (X₃) | H | H | 1.29 | 453.4 | 452.6 | 1 |
| 211 | cyclopentyl[5-(2,6-diethylphenyl)-1-(4-isopropylphenyl)-1H-pyrrolo[2,3-c]pyridin-3-yl]methanone | 2,6-diethylphenyl (X₁) | 4-isopropylphenyl (X₂) | cyclopentylcarbonyl (X₃) | H | H | 1.32 | 465.3 | 464.6 | 1 |
| 212 | 1-[5-(2,6-diethylphenyl)-1-(4-isopropylphenyl)-1H-pyrrolo[2,3-c]pyridin-3-yl]-2-methylbutan-1-one | 2,6-diethylphenyl (X₁) | 4-isopropylphenyl (X₂) | 2-methyl-1-hydroxybutyl (X₃) | H | H | 2.96 | 453.3 | 452.6 | 2 |

TABLE 1-continued

| Cmpd # | Name | Ar | Q | W | R₁ | R₉ | LC/MS Ret. Time (min.) | LC/MS M+1 | LC/MS Mass | LC/MS Method |
|---|---|---|---|---|---|---|---|---|---|---|
| 213 | cyclopentyl[5-(2,6-diethylphenyl)-1-(4-isopropylphenyl)-1H-pyrrolo[2,3-c]pyridin-3-yl]methanol | 2,6-diethylphenyl (X₁) | 4-isopropylphenyl (X₂) | cyclopentyl-CH(OH)- (X₃) | H | H | 2.96 | 467.3 | 466.7 | 2 |
| 214 | 1-[5-(2,6-diethylphenyl)-1-(5-ethylpyrimidin-2-yl)-1H-pyrrolo[2,3-c]pyridin-3-yl]-2-methylbutan-1-ol | 2,6-diethylphenyl (X₁) | 5-ethylpyrimidin-2-yl (X₂) | sec-butyl-CH(OH)- (X₃) | H | H | | | 442.6 | 1 |
| 215 | 5,7-bis(2,6-diethylphenyl)-3,4-dimethyl-1H-pyrrolo[2,3-c]pyridine | 2,6-diethylphenyl (X₁) | Me (X₃) | CH₃ (X₃) | (X₄, Et substituted) | CH₃ | 1.26 | 411.3 | 410.6 | 1 |
| 216 | 5-(2,6-diethylphenyl)-1-(2,5-dimethylbenzyl)-3,4-dimethyl-1H-pyrrolo[2,3-c]pyridine | 2,6-diethylphenyl (X₁) | 2,5-dimethylbenzyl (X₂) | CH₃ (X₃) | H | CH₃ | 1.26 | 397.3 | 396.6 | 1 |
| 217 | 5-(2,6-diethylphenyl)-1-(4,6-dimethoxypyrimidin-2-yl)-1H-pyrrolo[2,3-c]pyridine | 2,6-diethylphenyl (X₁) | 4,6-dimethoxypyrimidin-2-yl (X₂) | H | H | H | 1.2 | 389.3 | 388.5 | 1 |
| 218 | 1-[5-(2,6-diethylphenyl)-1-(4,6-dimethylpyrimidin-2-yl)-1H-pyrrolo[2,3-c]pyridin-3-yl]-2-methylbutan-1-ol | 2,6-diethylphenyl (X₁) | 4,6-dimethylpyrimidin-2-yl (X₂) | sec-butyl-CH(OH)- (X₃) | H | H | 1.26 | 443.4 | 442.6 | 1 |

TABLE I-continued

| Cmpd # | Name | Ar | Q | W | $R_1$ | $R_9$ | LC/MS Ret. Time (min.) | LC/MS M + 1 | LC/MS Mass | LC/MS Method |
|---|---|---|---|---|---|---|---|---|---|---|
| 219 | 5-(2,6-diethylphenyl)-1-(4,6-dimethyl pyrimidin-2-yl)-3-(1-ethoxy-2-methylbutyl)-1H-pyrrolo[2,3-c]pyridine | 2,6-diethylphenyl (X₁) | 4,6-dimethylpyrimidin-2-yl (X₂) | 1-ethoxy-2-methylbutyl (X₃) | H | H | 1.34 | 471.4 | 470.7 | 1 |
| 220 | 5-(2,6-diethylphenyl)-1-(5-isopropyl pyridin-2-yl)-1H-pyrrolo[2,3-c]pyridine | 2,6-diethylphenyl (X₁) | 5-isopropylpyridin-2-yl (X₂) | H | H | H | 1.2 | 370.3 | 369.5 | 1 |
| 221 | 5-(2,6-diethylphenyl)-1-pyridin-2-yl-1H-pyrrolo[2,3-c]pyridine | 2,6-diethylphenyl (X₁) | pyridin-2-yl (X₂) | H | H | H | 1.15 | 328.3 | 327.4 | 1 |
| 222 | 5-(2,6-diethylphenyl)-1-(4,6-diethylpyrimidin-2-yl)-1H-pyrrolo[2,3-c]pyridine | 2,6-diethylphenyl (X₁) | 4,6-diethylpyrimidin-2-yl (X₂) | H | H | H | 1.24 | 385.3 | 384.5 | 1 |
| 223 | 1-(5-bromo-4,6-diethylpyrimidin-2-yl)-5-(2,6-diethylphenyl)-1H-pyrrolo[2,3-c]pyridine | 2,6-diethylphenyl (X₁) | 5-bromo-4,6-diethylpyrimidin-2-yl (X₂) | H | H | H | 1.28 | 463.3 | 463.4 | 1 |

TABLE I-continued

| Cmpd # | Name | Ar | Q | W | R₁ | R₉ | LC/MS Ret. Time (min.) | LC/MS M+1 | LC/MS Mass | LC/MS Method |
|---|---|---|---|---|---|---|---|---|---|---|
| 224 | [5-(2,6-diethylphenyl)-1-(4-isopropylphenyl)-1H-pyrrolo[2,3-c]pyridin-3-yl]acetonitrile | | | | H | H | 2.45 | 408.2 | 407.6 | 1 |
| 225 | 2-[5-(2,6-diethylphenyl)-1-(4-isopropylphenyl)-1H-pyrrolo[2,3-c]pyridin-3-yl]-2-isobutyl-4-methylpentanenitrile | | | | H | H | 1.33 | 520.5 | 519.8 | 1 |
| 226 | 2-[5-(2,6-diethylphenyl)-1-(4-isopropylphenyl)-1H-pyrrolo[2,3-c]pyridin-3-yl]-4-methylpentanenitrile | | | | H | H | 1.27 | 464.4 | 463.7 | 1 |
| 227 | 2-[5-(2,6-diethylphenyl)-1-(4-isopropylphenyl)-1H-pyrrolo[2,3-c]pyridin-3-yl]-4-methylpentan-1-amine | | | | H | H | 1.18 | 468.4 | 467.7 | 1 |
| 228 | 5-(2,6-diethylphenyl)-1-(4-isopropylphenyl)-3-(4-propyl-1H-pyrazol-5-yl)-1H-pyrrolo[2,3-c]pyridine | | | | H | H | | | 476.7 | |
| 229 | 2-[5-(2,6-diethylphenyl)-1-(4-isopropylphenyl)-1H-pyrrolo[2,3-c]pyridin-3-yl]pentan-2-ol | | | | H | H | 2.53 | 455.3 | 454.7 | 2 |

TABLE I-continued

| Cmpd # | Name | Ar | Q | W | R$_1$ | R$_9$ | LC/MS Ret. Time (min.) | LC/MS M + 1 | LC/MS Mass | LC/MS Method |
|---|---|---|---|---|---|---|---|---|---|---|
| 230 | 2-[5-(2,6-diethylphenyl)-1-(4-isopropyl)phenyl)-1H-pyrrolo[2,3-c]pyridin-3-yl]-2-methylpropan-1-ol | 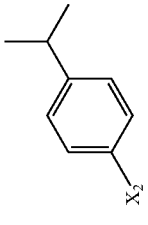 | 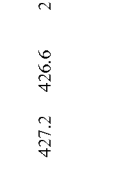 | 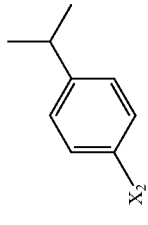 | H | H | 2.45 | 441.2 | 440.6 | 1 |
| 231 | 2-[5-(2,6-diethylphenyl)-1-(4-isopropyl)phenyl)-1H-pyrrolo[2,3-c]pyridin-3-yl]-4-methylpentan-1-ol | 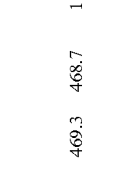 | 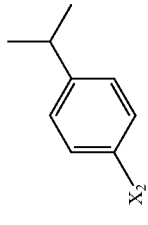 | 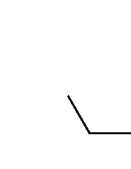 | H | H | 1.28 | 469.3 | 468.7 | 1 |
| 232 | 2-[5-(2,6-diethylphenyl)-1-(4-isopropyl)phenyl)-1H-pyrrolo[2,3-c]pyridin-3-yl]-propan-1-ol | 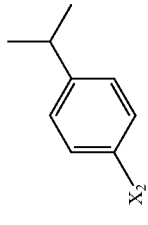 | | 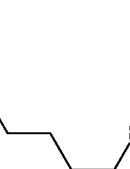 | H | H | 2.38 | 427.2 | 426.6 | 2 |
| 233 | 2-{5-(2,6-diethylphenyl)-1-(4-isopropyl)phenyl)-1H-pyrrolo[2,3-c]pyridin-3-yl]methyl}pentan-1-ol | | | 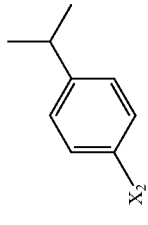 | H | H | 1.27 | 469.3 | 468.7 | 1 |
| 234 | 5-(2,6-diethylphenyl)-1-(4-isopropyl)phenyl)-3-(1-methylbutyl)-1H-pyrrolo[2,3-c]pyridine |  | | 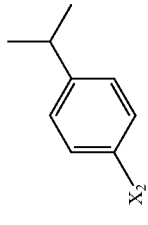 | H | H | 1.33 | 439.3 | 438.7 | 1 |
| 235 | 5-(2,6-diethylphenyl)-1-(4-isopropyl)phenyl)-4-methyl-1H-pyrrolo[2,3-c]pyridine |  | | H | H | CH$_3$ | 1.24 | 383.2 | 382.5 | 1 |

TABLE I-continued

| Cmpd # | Name | Ar | Q | W | R₁ | R₉ | LC/MS Ret. Time (min.) | LC/MS M + 1 | LC/MS Mass | LC/MS Method |
|---|---|---|---|---|---|---|---|---|---|---|
| 236 | 5-(2,6-diethylphenyl)-1-(4-isopropylphenyl)-3-(4-propylisoxazol-5-yl)-1H-pyrrolo[2,3-c]pyridine | 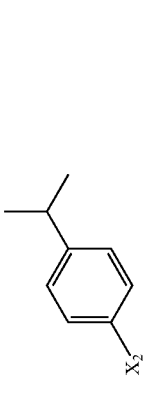 | 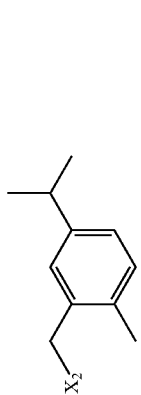 | 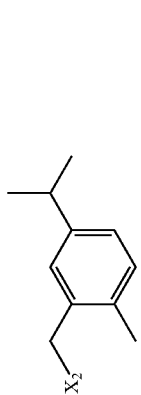 | H | H | 1.31 | 478.3 | 477.6 | 1 |
| 237 | 3-ethyl-4-[1-(5-isopropyl-2-methylbenzyl)-1H-pyrrolo[2,3-c]pyridin-5-yl]-1H-indazole | 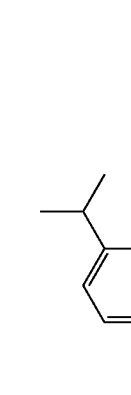 | 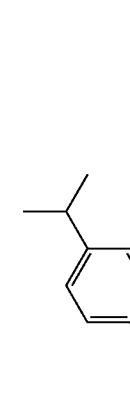 | H | H | H | 1.21 | 409.3 | 408.5 | 1 |
| 238 | methyl 2-[5-(2,6-diethylphenyl)-1-(4-isopropylphenyl)-1H-pyrrolo[2,3-c]pyridin-3-yl]-2-methylpropanoate | 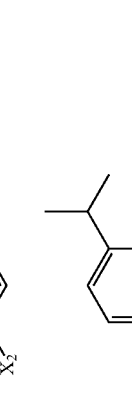 | 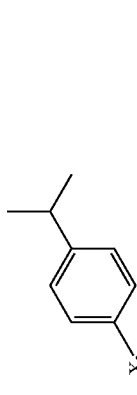 | 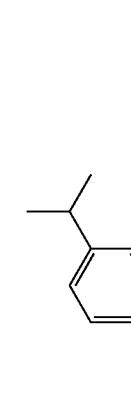 | H | H | 1.27 | 455.3 | 468.6 | 1 |
| 239 | methyl 1-[5-(2,6-diethylphenyl)-1-(4-isopropylphenyl)-1H-pyrrolo[2,3-c]pyridin-3-yl]cyclopropanecarboxylate | 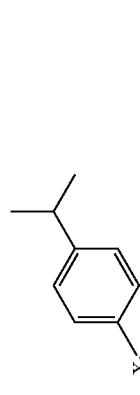 | 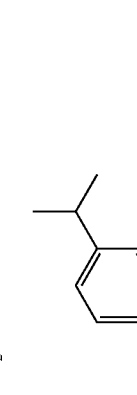 | 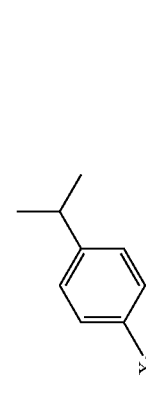 | H | H | 2.55 | 467.2 | 466.6 | 2 |
| 240 | 2-[5-(2,6-diethylphenyl)-1-(4-isopropylphenyl)-1H-pyrrolo[2,3-c]pyridin-3-yl]-2,5-dimethylhexan-3-ol | | | 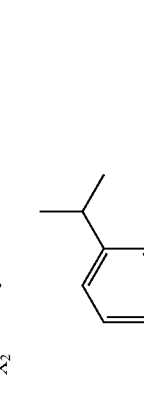 | H | H | 2.67 | 497.3 | 496.7 | 2 |
| 241 | 1-{1-[5-(2,6-diethylphenyl)-1-(4-isopropylphenyl)-1H-pyrrolo[2,3-c]pyridin-3-yl]cyclopropyl}-3-methylbutan-1-ol | | | | H | H | 2.63 | 495.3 | 494.7 | 2 |

TABLE I-continued

| Cmpd # | Name | Ar | Q | W | R₁ | R₉ | LC/MS Ret. Time (min.) | LC/MS M + 1 | LC/MS Mass | LC/MS Method |
|---|---|---|---|---|---|---|---|---|---|---|
| 242 | 2-[5-(2,6-diethylphenyl)-1-(4-isopropylphenyl)-1H-pyrrolo[2,3-c]pyridin-3-yl]-2-methylpropanoic acid | 2,6-diethylphenyl with X₁ | 4-isopropylphenyl with X₂ | 2-methylpropanoic acid with X₃ (HO-C(O)-C(CH₃)₂-) | H | H | 1.24 | 455.3 | 454.6 | 1 |
| 243 | [5-(2,6-diethylphenyl)-1-(4-isopropylphenyl)-1H-pyrrolo[2,3-c]pyridin-3-yl]acetic acid | 2,6-diethylphenyl with X₁ | 4-isopropylphenyl with X₂ | acetic acid with X₃ (HO-C(O)-CH₂-) | H | H | 1.21 | 427.3 | 426.6 | 1 |
| 244 | 1-[5-(2,6-diethylphenyl)-1-(3,4-difluorophenyl)-1H-pyrrolo[2,3-c]pyridin-3-yl]-3-methylbutan-1-one | 2,6-diethylphenyl with X₁ | 3,4-difluorophenyl with X₂ | 3-methylbutan-1-one with X₃ | H | H | 2.88 | 447.0 | 446.5 | 2 |
| 245 | 1-{5-(2,6-diethylphenyl)-1-[4-(trifluoromethoxy)phenyl]-1H-pyrrolo[2,3-c]pyridin-3-yl}-3-methylbutan-1-one | 2,6-diethylphenyl with X₁ | 4-(trifluoromethoxy)phenyl with X₂ | 3-methylbutan-1-one with X₃ | H | H | 2.96 | 495.1 | 494.6 | 2 |
| 246 | 1-[5-(2,6-diethylphenyl)-1-(3-fluoro-4-methylphenyl)-1H-pyrrolo[2,3-c]pyridin-3-yl]-3-methylbutan-1-one | 2,6-diethylphenyl with X₁ | 3-fluoro-4-methylphenyl with X₂ | 3-methylbutan-1-one with X₃ | H | H | 2.94 | 443.1 | 442.6 | 2 |
| 247 | 1-[5-(2,6-diethylphenyl)-1-(3,4-difluorophenyl)-1H-pyrrolo[2,3-c]pyridin-3-yl]-3-methylbutan-1-ol | 2,6-diethylphenyl with X₁ | 3,4-difluorophenyl with X₂ | 3-methylbutan-1-ol with X₃ | H | H | 1.24 | 449.3 | 448.6 | 1 |

TABLE I-continued

| Cmpd # | Name | Ar | Q | W | R$_1$ | R$_9$ | LC/MS Ret. Time (min.) | LC/MS M + 1 | LC/MS Mass | LC/MS Method |
|---|---|---|---|---|---|---|---|---|---|---|
| 248 | 1-{5-(2,6-diethylphenyl)-1-[4-(trifluoromethoxy)phenyl]-1H-pyrrolo[2,3-c]pyridin-3-yl}-3-methylbutan-1-ol | 2,6-diethylphenyl (X$_1$) | 4-OCF$_3$-phenyl (X$_2$) | CH(OH)CH$_2$CH(CH$_3$)$_2$ with X$_3$ | H | H | 1.27 | 497.3 | 496.6 | 1 |
| 249 | 1-{5-(2,6-diethylphenyl)-1-(3-fluoro-4-methylphenyl)-1H-pyrrolo[2,3-c]pyridin-3-yl]-3-methylbutan-1-ol | 2,6-diethylphenyl (X$_1$) | 3-F-4-methylphenyl (X$_2$) | CH(OH)CH$_2$CH(CH$_3$)$_2$ with X$_3$ | H | H | 1.26 | 445.3 | 444.6 | 1 |
| 250 | 2-{[5-(2,6-diethylphenyl)-1-(4-isopropylphenyl)-1H-pyrrolo[2,3-c]pyridin-3-yl]methyl}pentyl butylcarbamate | 2,6-diethylphenyl (X$_1$) | 4-isopropylphenyl (X$_2$) | n-Bu-NHC(O)O-CH$_2$CH(propyl)CH$_2$X$_3$ | H | H | | | 567.8 | |
| 251 | 2-{[5-(2,6-diethylphenyl)-1-(4-isopropylphenyl)-1H-pyrrolo[2,3-c]pyridin-3-yl]methyl}pentyl cyclopentylcarbamate | 2,6-diethylphenyl (X$_1$) | 4-isopropylphenyl (X$_2$) | cyclopentyl-NHC(O)O-CH$_2$CH(propyl)CH$_2$X$_3$ | H | H | 2.78 | 580.2 | 579.8 | 2 |
| 252 | 2-{[5-(2,6-diethylphenyl)-1-(4-isopropylphenyl)-1H-pyrrolo[2,3-c]pyridin-3-yl]methyl}pentyl benzylcarbamate | 2,6-diethylphenyl (X$_1$) | 4-isopropylphenyl (X$_2$) | benzyl-NHC(O)O-CH$_2$CH(propyl)CH$_2$X$_3$ | H | H | | | 601.8 | |

TABLE I-continued

| Cmpd # | Name | Ar | Q | W | $R_1$ | $R_9$ | LC/MS Ret. Time (min.) | LC/MS M + 1 | LC/MS Mass | LC/MS Method |
|---|---|---|---|---|---|---|---|---|---|---|
| 253 | 1-[1-(2-chloro-6-methyl-pyrimidin-4-yl)-5-(2,6-diethyl-phenyl)-1H-pyrrolo[2,3-c]pyridin-3-yl]-3-methylbutan-1-ol | 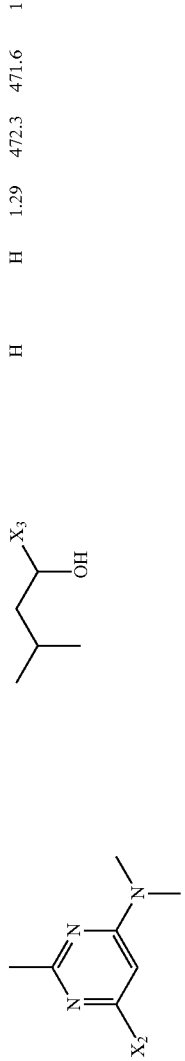 | 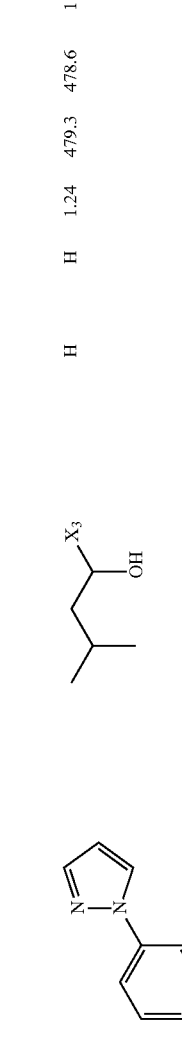 | 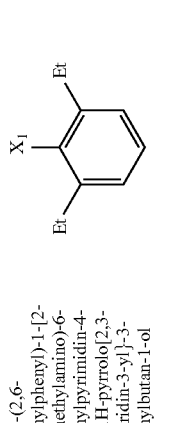 | H | H | 2.72 | 463.1 | 463.0 | 2 |
| 254 | 1-{5-(2,6-diethylphenyl)-1-[2-(dimethylamino)-6-methylpyrimidin-4-yl]-1H-pyrrolo[2,3-c]pyridin-3-yl}-3-methylbutan-1-ol | | 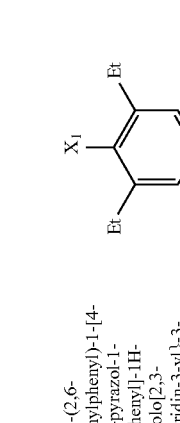 | | H | H | 1.29 | 472.3 | 471.6 | 1 |
| 255 | 1-{5-(2,6-diethylphenyl)-1-[4-(1H-pyrazol-1-yl)phenyl]-1H-pyrrolo[2,3-c]pyridin-3-yl}-3-methylbutan-1-ol | |  | | H | H | 1.24 | 479.3 | 478.6 | 1 |
| 256 | 1-{5-(2,6-diethylphenyl)-1-[4-(trifluoromethyl)phenyl]-1H-pyrrolo[2,3-c]pyridin-3-yl}-3-methylbutan-1-ol | | 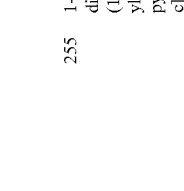 | | H | H | 1.25 | 481.2 | 480.6 | 1 |
| 257 | 1-{5-(2,6-diethylphenyl)-1-[4-(2,3-dihydroisoxazol-5-yl)phenyl]-1H-pyrrolo[2,3-c]pyridin-3-yl}-3-methylbutan-1-ol | | | | H | H | 1.22 | 482.3 | 481.6 | 1 |

TABLE I-continued

| Cmpd # | Name | Ar | Q | W | R₁ | R₉ | LC/MS Ret. Time (min.) | LC/MS M+1 | LC/MS Mass | LC/MS Method |
|---|---|---|---|---|---|---|---|---|---|---|
| 258 | methyl 2-{[5-(2,6-diethylphenyl)-1-(4-isopropylphenyl)-1H-pyrrolo[2,3-c]pyridin-3-yl]methyl}-2-ethylbutanoate | 2,6-diethylphenyl | 4-isopropylphenyl | methyl 2-ethyl-2-ethylbutanoate ester | H | H | | 510.7 | | 2 |
| 259 | 1-[5-(2,6-diethylphenyl)-1-(2-methoxy-6-methylpyrimidin-4-yl)-1H-pyrrolo[2,3-c]pyridin-3-yl]-3-methylbutan-1-ol | 2,6-diethylphenyl | 2-methoxy-6-methylpyrimidin-4-yl | 3-methylbutan-1-ol | H | H | 2.64 | 459.2 | 458.6 | 2 |
| 260 | 1-[5-(2,6-diethylphenyl)-1-(6-methoxy-5-methylpyrimidin-4-yl)-1H-pyrrolo[2,3-c]pyridin-3-yl]-3-methylbutan-1-ol | 2,6-diethylphenyl | 6-methoxy-5-methylpyrimidin-4-yl | 3-methylbutan-1-ol | H | H | 2.52 | 459.1 | 458.6 | 2 |
| 261 | 1-{5-(2,6-dimethylphenyl)-1-[4-(methoxymethyl)phenyl]-1H-pyrrolo[2,3-c]pyridin-3-yl}-2-ethylbutan-1-ol | 2,6-dimethylphenyl | 4-(methoxymethyl)phenyl | 2-ethylbutan-1-ol | H | H | 2.4 | 443.1 | 442.6 | 2 |
| 262 | 1-[5-(2,6-dimethylphenyl)-1-(4-isopropylphenyl)-1H-pyrrolo[2,3-c]pyridin-3-yl]-2-ethylbutan-1-ol | 2,6-dimethylphenyl | 4-isopropylphenyl | 2-ethylbutan-1-ol | H | H | 2.57 | 441.2 | 440.6 | 2 |
| 263 | 1-[5-(2,6-dimethylphenyl)-1-(4-isopropoxyphenyl)-1H-pyrrolo[2,3-c]pyridin-3-yl]-2-ethylbutan-1-ol | 2,6-dimethylphenyl | 4-isopropoxyphenyl | 2-ethylbutan-1-ol | H | H | 2.49 | 457.2 | 456.6 | 2 |

TABLE I-continued

| Cmpd # | Name | Ar | Q | W | R$_1$ | R$_9$ | LC/MS Ret. Time (min.) | LC/MS M+1 | LC/MS Mass | LC/MS Method |
|---|---|---|---|---|---|---|---|---|---|---|
| 264 | 1-[1-(2,6-dimethoxypyrimidin-4-yl)-5-(2,6-dimethylphenyl)-1H-pyrrolo[2,3-c]pyridin-3-yl]-2-ethylbutan-1-ol | | | | H | H | 1.26 | 461.2 | 460.6 | 1 |
| 265 | 1-[5-(2,6-dimethylphenyl)-1-(6-isopropoxypyridazin-3-yl)-1H-pyrrolo[2,3-c]pyridin-3-yl]-2-ethylbutan-1-one | | | | H | H | 1.28 | 457.3 | 456.6 | 1 |
| 266 | 1-[1-(2,6-dimethoxypyrimidin-4-yl)-5-(2,6-dimethylphenyl)-1H-pyrrolo[2,3-c]pyridin-3-yl]-2-ethylbutan-1-one | | | | H | H | 2.9 | 459.1 | 458.6 | 2 |
| 267 | 1-[1-(2-chloro-6-ethylpyrimidin-4-yl)-5-(2,6-dimethylphenyl)-1H-pyrrolo[2,3-c]pyridin-3-yl]-2-ethylbutan-1-one | | | | H | H | 3.14 | 461.1 | 461.0 | 2 |
| 268 | 1-[5-(2,6-dimethylphenyl)-1-(4-isopropoxyphenyl)-6-oxido-1H-pyrrolo[2,3-c]pyridin-3-yl]-2-ethylbutan-1-ol | | | | H | H | 1.67 | 473.1 | 472.6 | 2 |

TABLE I-continued

| Cmpd # | Name | Ar | Q | W | R₁ | R₉ | LC/MS Ret. Time (min.) | LC/MS M + 1 | LC/MS Mass | LC/MS Method |
|---|---|---|---|---|---|---|---|---|---|---|
| 269 | 1-[5-(2,6-dimethylphenyl)-1-(6-isopropoxypyradazin-3-yl)-1H-pyrrolo[2,3-c]pyridin-3-yl]-3,3-dimethylbutan-1-ol | 2,6-dimethylphenyl with X₁ | 6-isopropoxypyridazin-3-yl with X₂ | X₃-CH(OH)-CH₂-C(CH₃)₃ | H | H | 2.48 | 459.1 | 458.6 | 2 |
| 270 | 1-[5-(2,6-dimethylphenyl)-1-(6-isopropoxypyradazin-3-yl)-1H-pyrrolo[2,3-c]pyridin-3-yl]-3,3-dimethylbutan-1-one | 2,6-dimethylphenyl with X₁ | 6-isopropoxypyridazin-3-yl with X₂ | X₃-C(O)-CH₂-C(CH₃)₃ | H | H | 2.84 | 457.1 | 456.6 | 2 |
| 271 | 1-[5-(2,6-dimethylphenyl)-1-(6-isopropoxypyradazin-3-yl)-1H-pyrrolo[2,3-c]pyridin-3-yl]ethanone | 2,6-dimethylphenyl with X₁ | 6-isopropoxypyridazin-3-yl with X₂ | X₃-C(O)-CH₃ | H | H | 1.42 | 401.1 | 400.5 | 3 |
| 272 | 5-(2,6-dimethylphenyl)-1-(4-isopropoxyphenyl)-1H-pyrrolo[2,3-c]pyridine | 2,6-dimethylphenyl with X₁ | 4-isopropoxyphenyl with X₂ | H | H | H | 1.18 | 357.2 | 356.5 | 1 |
| 273 | 1-[5-(2,6-dimethylphenyl)-1-(6-isopropoxypyradazin-3-yl)-1H-pyrrolo[2,3-c]pyridin-3-yl]ethanol | 2,6-dimethylphenyl with X₁ | 6-isopropoxypyridazin-3-yl with X₂ | X₃-CH(OH)-CH₃ | H | H | 1.34 | 403.1 | 402.5 | 3 |
| 274 | 1-[5-(2,6-dimethylphenyl)-1-(2-isopropoxypyrimidin-4-yl)-1H-pyrrolo[2,3-c]pyridin-3-yl]-2-ethylbutan-1-ol | 2,6-dimethylphenyl with X₁ | 2-isopropoxypyrimidin-4-yl with X₂ | X₃-CH(OH)-CH(CH₂CH₃)₂ | H | H | 2.67 | 459.2 | 458.6 | 2 |

TABLE I-continued

| Cmpd # | Name | Ar | Q | W | $R_1$ | $R_9$ | LC/MS Ret. Time (min.) | LC/MS M + 1 | LC/MS Mass | LC/MS Method |
|---|---|---|---|---|---|---|---|---|---|---|
| 275 | 1-[5-(2,6-dimethylphenyl)-1-(2-ethoxy-6-methylpyrimidin-4-yl)-1H-pyrrolo[2,3-c]pyridin-3-yl]-2-ethylbutan-1-ol |  | 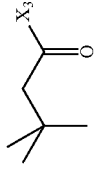 |  | H | H | 2.66 | 459.1 | 458.6 | 2 |
| 276 | 1-[1-(2-chloropyrimidin-4-yl)-5-(2,6-dimethylphenyl)-1H-pyrrolo[2,3-c]pyridin-3-yl]-3,3-dimethylbutan-1-one | 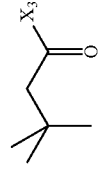 |  | 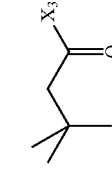 | H | H | 2.98 | 433.1 | 433.0 | 2 |
| 277 | 1-[1-(2-chloro-6-ethylpyrimidin-4-yl)-5-(2,6-dimethylphenyl)-1H-pyrrolo[2,3-c]pyridin-3-yl]-3,3-dimethylbutan-1-one |  |  | 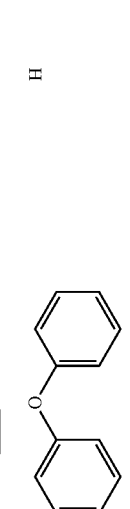 | H | H | 3.13 | 461.1 | 461.0 | 2 |
| 278 | 1-[5-(2,6-dimethylphenyl)-1-(6-isopropoxy pyrimidin-4-yl)-1H-pyrrolo[2,3-c]pyridin-3-yl]-3,3-dimethylbutan-1-one | 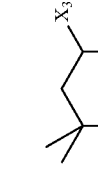 | | | H | H | 1.34 | 457.3 | 456.6 | 1 |
| 279 | 5-(2,6-dimethylphenyl)-1-(4-phenoxyphenyl)-1H-pyrrolo[2,3-c]pyridine | |  | H | H | H | 1.22 | 391.2 | 390.5 | 1 |
| 280 | 1-[5-(2,6-dimethylphenyl)-1-(6-isopropoxy pyrimidin-4-yl)-1H-pyrrolo[2,3-c]pyridin-3-yl]-3,3-dimethylbutan-1-ol | |  | | H | H | 1.29 | 459.3 | 458.6 | 1 |

TABLE I-continued

| Cmpd # | Name | Ar | Q | W | $R_1$ | $R_9$ | LC/MS Ret. Time (min.) | LC/MS M + 1 | LC/MS Mass | LC/MS Method |
|---|---|---|---|---|---|---|---|---|---|---|
| 281 | 1-[5-(2,6-dimethylphenyl)-1-(6-isopropoxy pyrimidin-4-yl)-1H-pyrrolo[2,3-c]pyridin-3-yl]-4,4,4-trifluorobutan-1-ol | 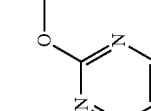 | 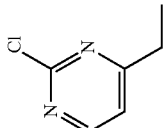 | 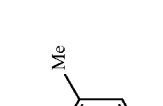 | H | H | 1.25 | 485.3 | 484.5 | 1 |
| 282 | 1-[1-(2-chloro-6-ethylpyrimidin-4-yl)-5-(2,6-dimethylphenyl)-1H-pyrrolo[2,3-c]pyridin-3-yl]-4,4,4-trifluorobutan-1-one | 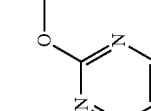 | 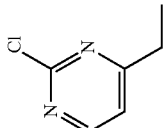 | 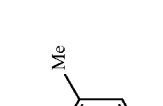 | H | H | 1.52 | 487.0 | 486.9 | 3 |
| 283 | 1-[1-(2-chloro-6-ethylpyrimidin-4-yl)-5-(2,6-dimethylphenyl)-1H-pyrrolo[2,3-c]pyridin-3-yl]-4,4,4-trifluorobutan-1-ol | 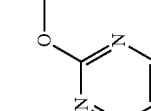 | 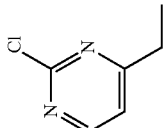 | 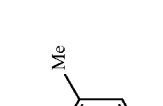 | H | H | 1.55 | 489.0 | 488.9 | 3 |
| 284 | 1-[5-(2,6-dimethylphenyl)-1-(6-isopropoxypyrimidin-4-yl)-1H-pyrrolo[2,3-c]pyridin-3-yl]-4,4,4-trifluorobutan-1-one | 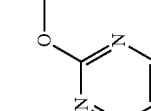 | 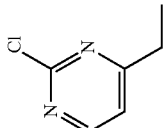 | 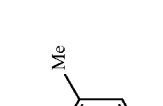 | H | H | 2.64 | 483.6 | 482.5 | 2 |

TABLE I-continued

| Cmpd # | Name | Ar | Q | W | R₁ | R₉ | LC/MS Ret. Time (min.) | LC/MS M + 1 | LC/MS Mass | LC/MS Method |
|---|---|---|---|---|---|---|---|---|---|---|
| 285 | 1-[5-(2,6-dimethylphenyl)-1-(6-ethyl-2-methoxypyrimidin-4-yl)-1H-pyrrolo[2,3-c]pyridin-3-yl]-3,3-dimethylbutan-1-ol | 2,6-dimethylphenyl with X₁ | 6-ethyl-2-methoxypyrimidin-4-yl with X₂ | 3,3-dimethylbutan-1-ol with X₃ | H | H | 2.67 | 459.3 | 458.6 | 2 |
| 286 | 1-[1-(2-chloro-6-ethylpyrimidin-4-yl)-5-(2,6-dimethylphenyl)-1H-pyrrolo[2,3-c]pyridin-3-yl]-3,3-dimethylbutan-1-ol | 2,6-dimethylphenyl with X₁ | 2-chloro-6-ethylpyrimidin-4-yl with X₂ | 3,3-dimethylbutan-1-ol with X₃ | H | H | 2.76 | 463.3 | 463.0 | 2 |
| 287 | 1-[5-(2,6-dimethylphenyl)-1-(6-ethyl-2-methoxypyrimidin-4-yl)-1H-pyrrolo[2,3-c]pyridin-3-yl]-4,4,4-trifluorobutan-1-ol | 2,6-dimethylphenyl with X₁ | 6-ethyl-2-methoxypyrimidin-4-yl with X₂ | 4,4,4-trifluorobutan-1-ol with X₃ | H | H | 1.27 | 485.2 | 484.5 | 1 |

Example 24

Pharmaceutical Preparations of Oral and Intravenous Administration

A. Tablets containing a C5a antagonist and an anti-arthritic agent that is not a C5a receptor antagonist can be prepared as illustrated below:

| Ingredient | Amount |
|---|---|
| C5a receptor antagonist | 5 mg-500 mg |
| C5a receptor-inactive therapeutic agent | 1 mg-500 mg |
| diluent, binder, disintigrant, lubricant, excipients | q.s. 200-400 mg. |

B. Tablets containing a C5a receptor antagonist as the only active ingredient can be prepared as illustrated below:

| Ingredient | mg | mg |
|---|---|---|
| C5a receptor antagonist | 10 | 50 |
| Microcrystalline Cellulose | 70.4 | 352 |
| Granular Mannitol | 15.1 | 75.5 |
| Croscarmellose Sodium | 3.0 | 15.0 |
| Colloidal Silicon Dioxide | 0.5 | 2.5 |
| Magnesium Stearate (Impalpable Powder) | 1.0 | 5.0 |
| Total (mg) | 100 | 500 |

C. Tablets containing a C5a receptor antagonist and a C5a receptor inactive agent may be prepared as follows:

| Ingredient | mg | mg |
|---|---|---|
| C5a receptor antagonist | 10 | 25 |
| C5a receptor inactive therapeutic agent | 10 | 25 |
| Microcrystalline Cellulose | 40 | 100 |
| Modified food corn starch | 1.05 | 4.25 |
| Magnesium stearate | 1.25 | 0.5 |

D. Intravenous formulations containing a C5a receptor antagonist and a C5a receptor inactive agent may be prepared as follows:

| Ingredient | Amount |
|---|---|
| C5a receptor antagonist | 0.5-10 mg |
| C5a receptor inactive therapeutic agent | 0.5-10 mg |
| Sodium Citrate | 5-50 mg |
| Citric Acid | 1-15 mg |
| Sodium Chloride | 1-8 mg |
| Water for Injection | to 1.0 liter |

E. Oral suspensions containing a C5a receptor antagonist and a C5a receptor inactive agent may be prepared as follows:

| Ingredient | Amount per 5 mL dose |
|---|---|
| C5a receptor antagonist | 5-100 mg |
| C5a receptor inactive therapeutic agent | 5-100 mg |
| Polyvinylpyrrolidone | 150 mg |
| Poly oxyethylene sorbitan monolaurate | 25 mg |
| Benzoic Acid | 10 mg to 5 mL with sorbitol solution (70%) |

Example 25

Preparation of Radiolabeled Probes

Compounds provided herein are prepared as radiolabeled probes by carrying out their synthesis using precursors comprising at least one atom that is a radioisotope. The radioisotope is preferably at least one of carbon (preferably $^{14}C$), hydrogen (preferably $^{3}H$), sulfur (preferably $^{35}S$), or iodine (preferably $^{125}I$. Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using a compound provided herein as substrate. In addition, certain precursors may be subjected to tritium-halogen exchange with tritium gas, tritium gas reduction of unsaturated bonds, or reduction using sodium borotritide, as appropriate.

Example 26

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds prepared as described herein.

Example 27

Assay for C5A Receptor Mediated Chemotaxis

This Example provides a standard assay of C5a receptor-mediated chemotaxis.

Human promonocytic U937 cells (or purified human or non-human neutrophils) are treated with dibutyryl cAMP for 48 hours prior to performing the assay. Human neutrophils or those from another mammalian species are used directly after isolation. The cells are pelleted and resuspended in culture media containing 0.1% fetal bovine serum (FBS) and 10 µg/mL calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately $3 \times 10^6$ cells/mL. Aliquots of this cell suspension are transferred to clean test tubes, which contain vehicle (1% DMSO in culture media containing 0.1% FBS) or varying concentrations of a compound of interest, and are incubated at room temperature for at least 30 minutes. The chemotaxis assay is performed in CHEMO TX 101-8, 96 well plates (Neuro Probe, Inc.; Gaithersburg, Md.). The bottom wells of the plate are filled with medium containing 0-10 nM of C5a, preferably derived from the same species of mammal as are the neutrophils or other cells (e.g., human C5a for human U937 cells). The top wells of the plate are filled with cell suspensions (compound- or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an $EC_{50}$ value.

As a control to ensure that cells retain chemotactic ability in the presence of the compound of interest, the bottom wells of the plate may be filled with varying concentrations chemoattractants that do not mediate chemotaxis via the C5a receptor, such as zymosan-activated serum (ZAS), N-formylmethionyl-leucyl-phenylalanine (FMLP) or leukotriene B4 (LTB4), rather than C5a, under which conditions compounds provided herein preferably do not detectably inhibit chemotaxis. Preferred C5a receptor modulators exhibit $EC_{50}$ values of less than 1 μM in the above assay for C5a mediated chemotaxis.

Example 28

Expression of a C5A Receptor

A human C5a receptor cDNA is obtained by PCR using 1) a forward primer adding a Kozak ribosome binding site and 2) a reverse primer that adds no additional sequence, and 3) an aliquot of a Stratagene Human Fetal Brain cDNA library as template. The sequence of the resulting PCR product is described in PCT International Application WO 02/49993 as SEQ ID NO: 1. The PCR product is subcloned into the cloning vector pCR-Script AMP (STRATAGENE, La Jolla, Calif.) at the Srf I site. It is then excised using the restriction enzymes EcoRI and NotI and subcloned in the appropriate orientation for expression into the baculoviral expression vector pBacPAK 9 (CLONTECH, Palo Alto, Calif.) that has been digested with EcoRI and NotI.

Example 29

Baculoviral Preparations for C5A Expression

The human C5a (hC5a) receptor baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 mL of insect medium for amplification. Each 1 mL volume of recombinant baculovirus (at passage 0) is used to infect a separate T25 flask containing $2\times10^6$ Sf9 cells in 5 mL of insect medium. After five days of incubation at 27° C., supernatant medium is harvested from each of the T25 infections for use as passage 1 inoculum.

Two of seven recombinant baculoviral clones are then chosen for a second round of amplification, using 1 mL of passage 1 stock to infect $1\times10^8$ cells in 100 mL of insect medium divided into 2 T175 flasks. Forty-eight hours post infection, passage 2 medium from each 100 mL prep is harvested and plaque assayed for titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post-infection the supernatant medium is harvested to yield passage 3 baculoviral stock.

The remaining cell pellet is assayed for affinity binding using the protocol of DeMartino et al. (1994) *J. Biol. Chem.* 269(20):14446-14450 (which is incorporated herein by reference for its teaching of binding assays at page 14447), adapted as follows. Radioligand is 0.005-0.500 nM [$^{125}$I]C5a (human recombinant) (New England Nuclear Corp., Boston, Mass.); the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/mL aprotinin; filtration is carried out using GF/C WHATMAN filters (presoaked in 1.0% polyethyeneimine for 2 hours prior to use); and the filters are washed twice with 5 mL cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression.

A multiplicity of infection of 0.1 and a 72-hour incubation period were the best infection parameters found for hC5a receptor expression in up to 1-liter Sf9 cell infection cultures.

Example 30

Baculoviral Infections

Log-phase SF9 cells (INVITROGEN Corp., Carlsbad Calif.), are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $G\square_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V6B003), which may be obtained from BIOSIGNAL Inc., Montreal.

The infections are conveniently carried out at a multiplicity of infection of 0.1:1.0:0.5:0.5. At 72 hours post-infection, a sample of cell suspension is analyzed for viability by trypan blue dye exclusion, and the remaining Sf9 cells are harvested via centrifugation (3000 rpm/10 minutes/4° C.).

Example 31

Purified Recombinant Insect Cell Membranes

Sf9 cell pellets are resuspended in homogenization buffer (10 mM HEPES, 250 mM sucrose, 0.5 μg/mL leupeptin, 2 μg/mL Aprotinin, 200 μM PMSF, and 2.5 mM EDTA, pH 7.4) and homogenized using a POLYTRON homogenizer (setting 5 for 30 seconds). The homogenate is centrifuged (536×g/10 minutes/4° C.) to pellet the nuclei. The supernatant containing isolated membranes is decanted to a clean centrifuge tube, centrifuged (48,000×g/30 minutes, 4° C.) and the resulting pellet resuspended in 30 mL homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100-150 mg of total membrane protein.

Example 32

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, 0.1% BSA, pH 7.4, 0.1 mM bacitracin, 100 KIU/mL aprotinin).

For saturation binding analysis, membranes (5-50 µg) are added to polypropylene tubes containing 0.005-0.500 nM [$^{125}$I]C5a (human (recombinant), New England Nuclear Corp., Boston, Mass.) with a final assay volume of 0.25 ml. Nonspecific binding is determined in the presence of 300 nM hC5a (Sigma Chemical Co., St. Louis, Mo.) and accounted for less than 10% of total binding. For evaluation of guanine nucleotide effects on receptor affinity, GTPγS is added to duplicate tubes at the final concentration of 50 µM.

For competition analysis, membranes (5-50 µg) are added to polypropylene tubes containing 0.030 nM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounted for less than 10% of total binding. Following a 2-hour incubation at room temperature, the reaction is terminated by rapid vacuum filtration. Samples are filtered over presoaked (in 1.0% polyethyleneimine for 2 hours prior to use) GF/C WHATMAN filters and rinsed 2 times with 5 mL cold binding buffer without BSA, bacitracin, or aprotinin. Remaining bound radioactivity is quantified by gamma counting. $K_I$ and Hill coefficient ("nH") are determined by fitting the Hill equation to the measured values with the aid of SIGMAPLOT software.

Example 33

Agonist-Induced GTP Binding

Agonist-stimulated GTP-gamma$^{35}$S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the hC5a receptor and three directing the expression of each of the three subunits of a heterotrimeric G-protein) are used to infect a culture of Sf9 cells as described above.

Agonist-stimulated GTP binding on purified membranes (prepared as described above) is assessed using hC5a (Sigma Chemical Co., St. Louis, Mo., USA) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pH 7.0, 120 mM NaCl, 2 mM MgCl2, 2 mM EGTA, 0.1% BSA, 0.1 mM bacitracin, 100 KIU/mL aprotinin, 5 µM GDP) and added to reaction tubes at a concentration of 30 µg protein/reaction tube. After adding increasing doses of the agonist hC5a at concentrations ranging from $10^{-12}$ M to $10^{-6}$ M, reactions are initiated by the addition of 100 pM GTP gamma$^{35}$S with a final assay volume of 0.25 ml. In competition experiments, non-radiolabeled test compounds (e.g., compounds of Formula I) are added to separate assays at concentrations ranging from $10^{-10}$ M to $10^{-5}$ M along with 10 nM hC5a to yield a final volume of 0.25 mL.

Neutral antagonists are those test compounds that reduce the C5a-stimulated GTP binding activity towards, but not below, baseline (the level of GTP bound by membranes in this assay in the absence of added C5a or other agonist and in the further absence of any test compound).

In contrast, in the absence of added C5a, certain preferred compounds reduce the GTP binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound that elevates GTP binding activity above baseline in the absence of added hC5a in this assay is characterized as having partial agonist activity. Preferred antagonist compounds provided herein do not elevate GTP binding activity under such conditions more than 10% above baseline, preferably not more than 5% above baseline, and most preferably not more than 2% above baseline.

Following a 60-minute incubation at room temperature, the reactions are terminated by vacuum filtration over GF/C filters (pre-soaked in wash buffer, 0.1% BSA) followed by washing with ice-cold wash buffer (50 mM Tris pH 7.0, 120 mM NaCl). The amount of receptor-bound (and thereby membrane-bound) GTPgamma$^{35}$S is determined by measuring the bound radioactivity, preferably by liquid scintillation spectrometry of the washed filters. Non-specific binding is determined using 10 mM GTPgammaS and typically represents less than 5 percent of total binding. Data is expressed as percent above basal (baseline). The results of these GTP binding experiments is analyzed using SIGMAPLOT software (SPSS Inc., Chicago, Ill.).

Example 34

Calcium Mobilization Assays

A. Response to C5a

U937 cells are grown in differentiation media (1 mM dibutyryl cAMP in RPMI 1640 medium containing 10% fetal bovine serum) for 48 hours at 37° C. then reseeded onto 96-well plates suitable for use in a FLIPR™ Plate Reader (Molecular Devices Corp., Sunnyvale Calif.). Cells are grown an additional 24 hours (to 70-90% confluence) before the assay. The cells are then washed once with Krebs Ringer solution. FLUO-3 calcium sensitive dye (Molecular Probes, Inc. Eugene, Oreg.) is added to 10 µg/mL and incubated with the cells in Krebs Ringer solution at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01-30.0 nM, using the FLIPR™ device (Molecular Devices). Differentiated U937 cells typically exhibit signals of 5,000-50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 μM. This stimulation typically triggers a signal of 1,000 to 12,000 arbitrary fluorescence light units. Certain preferred compounds produce less than a 10%, preferably less than a 5%, and most preferably less than a 2% alteration of this calcium mobilization signal when this control assay is carried out in the presence or absence of the compounds.

C. Assays for the Identification of Receptor Modulatory Agents: Antagonists and Agonists Those of skill in the art will recognize that the calcium mobilization assay described above may be readily adapted for identifying test compounds as having agonist or antagonist activity at the human C5a receptor.

For example, in order to identify antagonist compounds, differentiated U937 cells are washed and incubated with Fluo-3 dye as described above. One hour prior to measuring the fluorescence signal, a subset of the cells is incubated with a 1 μM concentration of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

Example 35

Assays to Evaluate Agonist Activity of Small Molecule C5A Receptor Antagonists

Certain preferred compounds of Formula I are C5a receptor antagonists that do not possess significant (e.g., greater than 5%) agonist activity in any of the C5a mediated functional assays discussed herein. Such agonist activity can be evaluated, for example, in the assay of C5a induced GTP binding given above, by measuring small molecule mediated GTP binding in the absence of the natural agonist, C5a. Similarly, in a calcium mobilization assay such as the assay described above a small molecule compound can be directly assayed for the ability of the compound to stimulate calcium levels in the absence of the natural agonist, C5a. The preferred extent of C5a agonist activity exhibited by certain compounds provided herein is less than 10%, more preferably less than 5% and most preferably less than 2% of the response elicited by the natural agonist, C5a.

Example 36

MDCK Toxicity Assay

This Example illustrates the evaluation of compound toxicity using a Madin Darby canine kidney (MDCK) cell cytotoxicity assay.

1 μL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog #30-2003). 100 μL of diluted cells is added to each well, except for five standard curve control wells that contain 100 μL of warm medium without cells. The plate is then incubated at 37° C. under 95% $O_2$, 5% $CO_2$ for 2 hours with constant shaking. After incubation, 50 μL of mammalian cell lysis solution" (available as a component of the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 μL of serially diluted PACKARD standard is added to each of the standard curve control wells to yield a final concentration in each subsequent well of 200 nM, 100 nM, 50 nM, 25 nM and 12.5 nM. PACKARD substrate solution (50 μL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 μM of a preferred test compound exhibit ATP levels that are at least 80%, preferably at least 90%, of the untreated cells. When a 100 μM concentration of the test compound is used, cells treated with preferred test compounds exhibit ATP levels that are at least 50%, preferably at least 80%, of the ATP levels detected in untreated cells.

What is claimed is:
1. A compound of the formula:

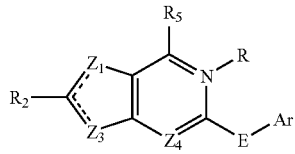

or a pharmaceutically acceptable salt thereof, wherein:
E is a single bond, O, S(O)$_m$, or CR$_6$R$_7$;
R$_6$ and R$_7$ are independently hydrogen or C$_1$-C$_4$ alkyl;
m is 0, 1, or 2;
Ar is chosen from:
phenyl which is mono-, di-, or tri-substituted, 1-naphthyl and 2-naphthyl, each of which is optionally mono-, di-, or tri-substituted, and optionally mono-, di-, or tri-substituted heteroaryl, said heteroaryl having from 1 to 3 rings, 5 to 7 ring members in each ring and, in at least one of said rings, from 1 to about 3 heteroatoms selected from the group consisting of N, O, and S;
the group:

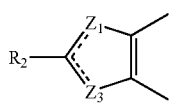

represents an aromatic 5-membered ring system containing exactly one heteroatom, wherein:
Z$_1$ is CR$_1$ or NR$_1$";
Z$_3$ is CR$_3$ or NR$_3$";
R$_1$ and R$_1$" are chosen from C$_1$-C$_{10}$alkyl, C$_2$-C$_{10}$alkenyl, C$_2$-C$_{10}$alkynyl, C$_3$-C$_7$cycloalkyl, (C$_3$-C$_7$cycloalkyl)C$_1$-C$_4$alkyl, three to nine membered heterocycloalkyl, (three to nine membered heterocycloalkyl)C$_1$-C$_4$alkyl, aryl, (aryl)C$_1$-C$_4$alkyl, heteroaryl, (heteroaryl)C$_1$-C$_4$alkyl, each of which is substituted with 0 or more substituents independently chosen from halogen, hydroxy, amino, oxo, cyano, C$_1$-C$_6$alkyl, C$_1$-C$_6$alkoxy, C$_1$-C$_6$hydroxyalkyl, C$_1$-C$_6$alkoxyC$_1$-C$_6$alkyl, C$_1$-C$_6$haloalkoxy, C$_5$-C$_7$heteroaryl, mono- and di-(C$_1$-C$_6$)alkylamino, and —XR$_C$;
R$_2$ is chosen from hydrogen, halogen, hydroxy, amino, cyano, nitro, C$_1$-C$_6$alkyl, halo(C$_1$-C$_6$)alkyl, C$_1$-C$_6$alkoxy, amino(C$_1$-C$_6$)alkyl, and mono and di(C$_1$-C$_6$)alkylamino;
R$_3$ and R$_3$" are independently chosen from C$_4$-C$_{10}$alkyl, halo(C$_4$-C$_{10}$)alkyl, C$_4$-C$_{10}$alkoxy, amino(C$_4$-C$_{10}$)alkyl, hydroxy(C$_4$-C$_{10}$)alkyl, mono and di(C$_4$-C$_{10}$)alkylamino, C$_3$-C$_7$cycloalkyl, (C$_3$-C$_7$cycloalkyl)C$_1$-C$_4$alkyl, three to nine membered heterocycloalkyl, (three to nine membered heterocycloalkyl)C$_1$-C$_4$alkyl, aryl, and heteroaryl, each of which is substituted with 0 or more substituents independently chosen from halogen, hydroxy, amino, oxo, cyano, C$_1$-C$_6$alkyl, C$_1$-C$_6$alkoxy, C$_1$-C$_6$hydroxyalkyl, C$_1$-C$_6$alkoxyC$_1$-C$_6$alkyl, C$_1$-C$_6$haloalkoxy, C$_5$-C$_7$heteroaryl, mono- and di-(C$_1$-C$_6$)alkylamino, —XR$_C$, and Y;
Z$_4$ is CR$_4$;
R is absent or oxygen;
R$_4$ is chosen from hydrogen, halogen, hydroxy, amino, cyano, C$_1$-C$_{10}$alkyl, C$_2$-C$_{10}$alkenyl, C$_2$-C$_{10}$alkynyl, halo(C$_1$-C$_{10}$)alkyl, C$_1$-C$_{10}$alkoxy, amino(C$_1$-C$_{10}$)alkyl, hydroxy(C$_1$-C$_{10}$)alkyl, (C$_2$-C$_{10}$)alkoxyalkyl mono and di(C$_1$-C$_{10}$)alkylamino, C$_3$-C$_7$cycloakyl, (C$_3$-C$_7$cycloakyl)C$_1$-C$_4$alkyl, three to nine membered heterocycloalkyl, (three to nine membered heterocycloalkyl)C$_1$-C$_4$alkyl, (CH$_2$)$_p$COOH, (CH$_2$)$_p$COOR$_A$, (CH$_2$)$_p$CONR$_A$R$_B$, (CH$_2$)$_p$S(O)$_m$R$_A$, S(O)$_m$NR$_A$R$_B$, aryl, and heteroaryl, each of which is substituted with 0 or more substituents independently chosen from halogen, hydroxy, amino, oxo, cyano, C$_1$-C$_6$alkyl, C$_1$-C$_6$alkoxy, C$_1$-C$_6$hydroxyalkyl, C$_1$-C$_6$alkoxyC$_1$-C$_6$alkyl, C$_1$-C$_6$haloalkoxy, C$_5$-C$_7$heteroaryl, mono- and di-(C$_1$-C$_6$)alkylamino, —XR$_C$, and Y;
R$_5$ is chosen from hydrogen, halogen, amino, cyano, C$_1$-C$_{10}$alkyl, C$_2$-C$_{10}$alkenyl, C$_2$-C$_{10}$alkynyl, halo(C$_1$-C$_{10}$)alkyl, C$_1$-C$_{10}$alkoxy, amino(C$_1$-C$_{10}$)alkyl, hydroxy(C$_1$-C$_{10}$)alkyl, (C$_2$-C$_{10}$)alkoxyalkyl mono and di(C$_1$-C$_{10}$)alkylamino, C$_3$-C$_7$cycloakyl, (C$_3$-C$_7$cycloakyl)C$_1$-C$_4$alkyl, three to nine membered heterocycloalkyl, (three to nine membered heterocycloalkyl)C$_1$-C$_4$alkyl, (CH$_2$)$_p$COOH, (CH$_2$)$_p$COOR$_A$, (CH$_2$)$_p$CONR$_A$R$_B$, (CH$_2$)$_p$S(O)$_m$R$_A$, S(O)$_m$NR$_A$R$_B$, aryl, and heteroaryl, each of which is substituted with 0 or more substituents independently chosen from halogen, amino, oxo, cyano, C$_1$-C$_6$alkyl, C$_1$-C$_6$alkoxy, C$_1$-C$_6$hydroxyalkyl, C$_1$-C$_6$alkoxyC$_1$-C$_6$alkyl, C$_1$-C$_6$haloalkoxy, C$_5$-C$_7$heteroaryl, mono- and di-(C$_1$-C$_6$)alkylamino, —XR$_C$, and Y;
R$_A$ is independently selected at each occurrence from halogen, cyano, nitro, halo(C$_1$-C$_6$)alkyl, halo(C$_1$-C$_6$)alkoxy, hydroxy, amino, C$_1$-C$_6$alkyl substituted with 0-2 R$_B$, C$_2$-C$_6$alkenyl substituted with 0-2 R$_B$, C$_2$-C$_6$alkynyl substituted with 0-2 R$_B$, C$_3$-C$_7$cycloalkyl substituted with 0-2 R$_B$, (C$_3$-C$_7$cycloalkyl) C$_1$-C$_4$alkyl substituted with 0-2 R$_B$, C$_1$-C$_6$alkoxy substituted with 0-2 R$_B$, —NH(C$_1$-C$_6$alkyl) substituted with 0-2 R$_B$, —N(C$_1$-C$_6$alkyl)(C$_1$-C$_6$alkyl) each C$_1$-C$_6$alkyl independently substituted with 0-2 R$_B$, —XR$_C$, and Y;
R$_B$ is independently selected at each occurrence from the group consisting of halogen, hydroxy, cyano, amino, C$_1$-C$_4$alkyl, —O(C$_1$-C$_4$alkyl), —NH(C$_1$-C$_4$alkyl), —N(C$_1$-C$_4$alkyl)(C$_1$-C$_4$alkyl), —S(O)$_n$(alkyl), halo (C$_1$-C$_4$)alkyl, halo(C$_1$-C$_4$)alkoxy, CO(C$_1$-C$_4$alkyl), CONH(C$_1$-C$_4$alkyl), CON(C$_1$-C$_4$alkyl)(C$_1$-C$_4$alkyl), —XR$_C$, and Y;
R$_C$ and R$_D$, which may be the same or different, are independently selected at each occurrence from:
hydrogen, and
straight, branched, or cyclic alkyl groups, including (cycloalkyl)alkyl groups consisting of 1 to 8 carbon atoms, which straight, branched, or cyclic alkyl groups contain zero or one or more double or triple bonds, each of which 1 to 8 carbon atoms may be further substituted with one or more substituent(s) independently selected from oxo, hydroxy, halogen, cyano, amino, C$_1$-C$_6$alkoxy, —NH(C$_1$-C$_6$alkyl), —N(C$_1$-C$_6$alkyl)(C$_1$-C$_6$alkyl), —NHC(═O)(C$_1$-C$_6$alkyl), —N(C$_1$-C$_6$alkyl)C(═O)(C$_1$-C$_6$alkyl), —NHS(O)$_n$(C$_1$-C$_6$alkyl), —S(O)$_n$(C$_1$-C$_6$alkyl), —S(O)$_n$NH(C$_1$-C$_6$alkyl), —S(O)$_n$N(C$_1$-C$_6$alkyl) (C$_1$-C$_6$alkyl), and Z;
X is independently selected at each occurrence from the group consisting of —CH$_2$—, —CHR$_D$—, —O—, —C(═O)—, —C(═O)O—, —S(O)$_n$—, —NH—, —NR$_D$—, —C(═O)NH—, —C(═O)NR$_D$—, —S(O)$_n$ —NH—, —S(O)$_n$NR$_D$—, —OC(=S)S—, —NHC(=O)—, —NR$_D$C(=O)—, —NHS(O)$_n$—, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, C$_1$-C$_4$alkyl, —O(C$_1$-C$_4$alkyl), —NH(C$_1$-C$_4$alkyl), —N(C$_1$-C$_4$alkyl)(C$_1$-C$_4$alkyl), and —S(O)$_n$(alkyl), wherein said 3- to 7-membered heterocyclic groups contain one or more heteroatom(s) independently selected from N, O, and S, with the point of attachment being either carbon or nitrogen; and n is independently selected at each occurrence from 0, 1, and 2.

2. The compound or salt of claim 1, wherein Z$_1$=NR$_1$", Z$_3$=CR$_3$, Z$_4$=CR$_4$, and R is absent at each occurrence.

3. The compound or salt of claim 1, wherein Z$_1$=CR$_1$, Z$_3$=CR$_3$", Z$_4$=CR$_4$, and R is absent.

4. The compound or salt of claim 1, wherein R$_1$ and R$_1$" are selected from C$_1$-C$_{10}$alkyl, C$_2$-C$_{10}$alkenyl, C$_3$-C$_7$cycloalkyl, (C$_3$-C$_7$cycloalkyl)C$_1$-C$_4$alkyl, phenyl, 1-naphthyl, 2-naphthyl, pyridinyl, pyrazinyl, pyrimidinyl, benzyl, pyridinyl-methyl, pyrazinyl-methyl, pyrimidinyl-methyl, each of which is substituted with between 0 and 2 substituents independently chosen from halogen, hydroxy, amino, oxo, cyano, C$_1$-C$_6$alkyl, C$_1$-C$_6$alkoxy, C$_1$-C$_6$hydroxyalkyl, C$_1$-C$_6$alkoxyC$_1$-C$_6$alkyl, C$_1$-C$_6$haloalkoxy, C$_5$-C$_7$heteroaryl, mono- and di-(C$_1$-C$_6$)alkylamino, and —XR$_C$.

5. The compound or salt of claim 1, wherein R$_1$ and R$_1$" are selected from C$_1$-C$_{10}$alkyl, phenyl, 1-naphthyl, 2-naphthyl, pyridinyl, pyrazinyl, pyrimidinyl, benzyl, pyridinyl-methyl, pyrazinyl-methyl, pyrimidinyl-methyl, cyclohexane, indanyl, chromanyl, benzocycloheptenyl, and tetrahydronaphthyl, each of which is substituted with between 0 and 2 substituents independently selected from halogen, hydroxy, amino, oxo, cyano, C$_1$-C$_3$alkyl, C$_1$-C$_3$alkoxy, C$_1$-C$_3$hydroxyalkyl, C$_2$-C$_4$alkoxyalkyl, C$_1$-C$_2$haloalkoxy, C$_5$-C$_6$heteroaryl, mono- and di-(C$_1$-C$_2$)alkylamino, COOH, COO(C$_1$-C$_4$alkyl), CONH(C$_1$-C$_4$alkyl), and CON(C$_1$-C$_4$alkyl)$_2$.

6. The compound or salt of claim 1, wherein Ar is selected from the group consisting of phenyl, pyridyl and pyrimidinyl each of which is mono- di- or trisubstituted with substituents independently chosen from halogen, cyano, nitro, halo(C$_1$-C$_6$)alkyl, halo(C$_1$-C$_6$)alkoxy, hydroxy, amino, C$_1$-C$_6$alkyl, C$_2$-C$_6$alkenyl, C$_2$-C$_6$alkynyl, C$_3$-C$_7$cycloalkyl, (C$_3$-C$_7$cycloalkyl)C$_1$-C$_4$alkyl, C$_1$-C$_6$alkoxy, mono- and di(C$_1$-C$_6$alkyl)amino, amino(C$_1$-C$_6$)alkyl, and mono- and di(C$_1$-C$_6$alkyl)amino, wherein, in Ar, at least one of the positions ortho to the point of attachment is substituted.

7. The compound or salt of claim 1, wherein R$_2$ is hydrogen, methyl, or ethyl.

8. The compound or salt of claim 1, wherein R$_4$ and R$_5$ are independently selected from hydrogen, halogen, hydroxy, amino, cyano, C$_1$-C$_6$alkyl, halo(C$_1$-C$_4$)alkyl, C$_1$-C$_6$alkoxy, (C$_2$-C$_6$)alkoxyalkyl mono and di(C$_1$-C$_6$)alkylamino, phenyl, 5 to 6 membered heterocycloalkyl and 5 to 6 member heteroaryl, each of which is substituted with 0 or more substituents independently chosen from halogen, hydroxy, amino, oxo, cyano, C$_1$-C$_6$alkyl, C$_1$-C$_6$alkoxy, C$_1$-C$_6$hydroxyalkyl, C$_1$-C$_6$alkoxyC$_1$-C$_6$alkyl, C$_1$-C$_6$haloalkoxy, C$_5$-C$_7$heteroaryl, mono- and di-(C$_1$-C$_6$)alkylamino, —XR$_C$, and Y.

9. The compound or salt of claim 1, wherein R$_4$ and R$_5$ are independently selected from hydrogen, halogen, hydroxy, amino, cyano, C$_1$-C$_6$alkyl, C$_1$-C$_6$alkoxy, mono- and di-(C$_1$-C$_6$alkyl)amino.

10. The compound or salt of claim 1, wherein

Z$_1$ is NR$_1$", wherein R$_1$" is selected from C$_3$-C$_{10}$alkyl, C$_5$-C$_7$cycloalkyl, (benzo)C$_5$-C$_7$cycloalkyl, (C$_5$-C$_7$cycloalkyl)methyl, each of which is substituted with between 0 and 2 substituents selected from halogen, C$_1$-C$_2$alkyl, haloC$_1$-C$_2$alkyl, C$_1$-C$_2$alkoxy, and mono- and di-( C$_1$-C$_2$alkyl)amino;

Z$_3$ is CR$_3$, wherein R$_3$ is selected from phenyl substituted with 0-2 independently selected R$_B$ groups, five to seven membered heterocycloalkyl substituted with 0-2 independently selected R$_A$, —(CH$_2$)$_p$C(O)R$_A$, and —(CH$_2$)$_p$S(O)$_2$R$_C$; and p is 0, 1, 2, or 3.

11. A compound of the formula:

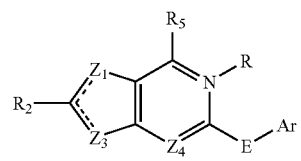

or a pharmaceutically acceptable salt thereof, wherein:

E is a single bond, O, S(O)$_m$, or CR$_6$R$_7$;

R$_6$ and R$_7$ are independently hydrogen or C$_1$-C$_4$ alkyl;

m is 0, 1, or 2;

Ar is chosen from:

phenyl which is mono-, di-, or tri-substituted, 1-naphthyl and 2-naphthyl, each of which is optionally mono-, di-, or tri-substituted, and optionally mono-, di-, or tri-substituted heteroaryl, said heteroaryl having from 1 to 3 rings, 5 to 7 ring members in each ring and, in at least one of said rings, from 1 to about 3 heteroatoms selected from the group consisting of N, O, and S;

the group:

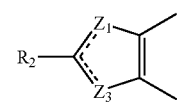

represents an aromatic 5-membered ring system containing exactly one heteroatom, wherein:

Z$_1$ is CR$_1$ or NR$_1$";

Z$_3$ is CR$_3$ or NR$_3$";

R$_1$ and R$_1$" are chosen from (aryl)C$_0$-C$_4$alkyl and (heteroaryl)C$_0$-C$_4$alkyl, each of which is substituted with 0 or more substituents independently chosen from halogen, hydroxy, amino, oxo, cyano, C$_1$-C$_6$alkyl, C$_1$-C$_6$alkoxy, phenoxy, benzyloxy, C$_1$-C$_6$hydroxyalkyl, C$_2$-C$_6$alkoxyalkyl, C$_1$-C$_6$haloalkoxy, C$_3$-C$_7$cycloalkyl, three to seven membered heterocycloalkyl, C$_5$-C$_7$heteroaryl, phenyl, mono- and di-(C$_1$-C$_6$)alkylamino, mono- and di-(C$_1$-C$_6$)alkylamino(C$_1$-C$_6$)alkoxy, —(C(R$_x$)$_2$)$_p$C(O)R$_A$, and —(C(R$_x$)$_2$)$_p$S(O)$_2$R$_C$ and —XR$_C$;

R$_2$ is chosen from hydrogen, halogen, hydroxy, amino, cyano, nitro, C$_1$-C$_6$alkyl, halo(C$_1$-C$_6$)alkyl, C$_1$-C$_6$alkoxy, amino(C$_1$-C$_6$)alkyl, and mono and di(C$_1$-C$_6$)alkylamino;

$R_3$ is chosen from hydrogen, halogen, hydroxy, amino, cyano, $(CH_2)_pC(O)R_A$, $(CH_2)_pS(O)_mR_A$, $C_1$-$C_{10}$alkyl, halo($C_1$-$C_{10}$)alkyl, $C_1$-$C_{10}$alkoxy, amino($C_1$-$C_{10}$)alkyl, hydroxy($C_1$-$C_{10}$)alkyl, ($C_2$-$C_{10}$)alkoxyalkyl mono and di($C_1$-$C_{10}$)alkylamino, $C_3$-$C_7$cycloakyl, ($C_3$-$C_7$cycloakyl)$C_1$-$C_4$alkyl, three to nine membered heterocycloalkyl, (three to nine membered heterocycloalkyl)$C_1$-$C_4$alkyl, aryl, and heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$)alkylamino, —$XR_C$, and Y;

$R_3''$ is chosen from hydrogen, $C_1$-$C_{10}$alkyl, halo($C_1$-$C_{10}$)alkyl, $C_1$-$C_{10}$alkoxy, amino($C_1$-$C_{10}$)alkyl, hydroxy($C_1$-$C_{10}$)alkyl, ($C_2$-$C_{10}$)alkoxyalkyl, $(CH_2)_pC(O)R_A$, $(CH_2)_p S(O)_mR_A$, mono and di($C_1$-$C_{10}$)alkylamino, $C_3$-$C_7$cycloakyl, ($C_3$-$C_7$cycloakyl)$C_1$-$C_4$alkyl, three to nine membered heterocycloalkyl, (three to nine membered heterocycloalkyl)$C_1$-$C_4$alkyl, aryl, and heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$)alkylamino, —$XR_C$, and Y;

p is 0, 1, 2, 3, or 4;

$Z_4$ is $CR_4$;

R is absent or oxygen;

$R_4$ and $R_5$ are independently chosen from hydrogen, halogen, cyano, nitro, amino, mono or di($C_1$-$C_6$alkyl)amino, $C_1$-$C_6$alkyl, $C_2$-$C_6$alkenyl, $C_2$-$C_6$alkynyl, ($C_3$-$C_7$cycloalkyl)$C_0$-$C_4$alkyl, $C_3$-$C_7$cycloalkoxy, halo$C_1$-$C_6$alkyl, halo($C_1$-$C_6$)alkoxy, $C_1$-$C_6$alkoxy, $S(O)_n(C_1$-$C_6$alkyl), phenyl, 5-7 membered heteroaryl, and three to seven membered heterocycloalkyl, each of which is substituted with between 0 and 4 groups selected halogen, hydroxy, amino, oxo, cyano, $C_1$-$C_4$alkyl, $C_1$-$C_4$alkoxy, and mono- and di($C_1$-$C_4$)alkylamino;

Rx is independently selected at each occurrence from hydrogen or $C_1$-$C_4$alkyl;

$R_A$ is independently selected at each occurrence from halogen, cyano, nitro, halo($C_1$-$C_6$)alkyl, halo($C_1$-$C_6$)alkoxy, hydroxy, amino, $C_1$-$C_6$alkyl substituted with 0-2 $R_B$, $C_2$-$C_6$alkenyl substituted with 0-2 $R_B$, $C_2$-$C_6$alkynyl substituted with 0-2 $R_B$, $C_3$-$C_7$cycloalkyl substituted with 0-2 $R_B$, ($C_3$-$C_7$cycloalkyl) $C_1$-$C_4$alkyl substituted with 0-2 $R_B$, $C_1$-$C_6$alkoxy substituted with 0-2 $R_B$, —NH($C_1$-$C_6$alkyl) substituted with 0-2 $R_B$, —N($C_1$-$C_6$alkyl)($C_1$-$C_6$alkyl) each $C_1$-$C_6$alkyl independently substituted with 0-2 $R_B$, —$XR_C$, and Y;

$R_B$ is independently selected at each occurrence from the group consisting of halogen, hydroxy, cyano, amino, $C_1$-$C_4$alkyl, —O($C_1$-$C_4$alkyl), —NH($C_1$-$C_4$alkyl), —N($C_1$-$C_4$alkyl)($C_1$-$C_4$alkyl), —S(O)$_n$(alkyl), halo($C_1$-$C_4$)alkyl, halo($C_1$-$C_4$)alkoxy, CO($C_1$-$C_4$alkyl), CONH($C_1$-$C_4$alkyl), CON($C_1$-$C_4$alkyl)($C_1$-$C_4$alkyl), —$XR_C$, and Y;

$R_C$ and $R_D$, which may be the same or different, are independently selected at each occurrence from:
hydrogen, and
straight, branched, or cyclic alkyl groups, including (cycloalkyl)alkyl groups consisting of 1 to 8 carbon atoms, which straight, branched, or cyclic alkyl groups contain zero or one or more double or triple bonds, each of which 1 to 8 carbon atoms may be further substituted with one or more substituent(s) independently selected from oxo, hydroxy, halogen, cyano, amino, $C_1$-$C_6$alkoxy, —NH($C_1$-$C_6$alkyl), —N($C_1$-$C_6$alkyl)($C_1$-$C_6$alkyl), —NHC(=O)($C_1$-$C_6$alkyl), —N($C_1$-$C_6$alkyl)C(=O)($C_1$-$C_6$alkyl), —NHS(O)$_n$($C_1$-$C_6$alkyl), —S(O)$_n$($C_1$-$C_6$alkyl), —S(O)$_n$NH($C_1$-$C_6$alkyl), —S(O)$_n$N($C_1$-$C_6$alkyl)($C_1$-$C_6$alkyl), and Z;

X is independently selected at each occurrence from the group consisting of —$CH_2$—, —$CHR_D$—, —O—, —C(=O)—, —C(=O)O—, —S(O)$_n$—, —NH—, —$NR_D$—, —C(=O)NH—, —C(=O)$NR_D$—, —S(O)$_n$NH—, —S(O)$_n NR_D$—, —OC(=S)S—, —NHC (=O)—, —$NR_DC$(=O)—, —NHS(O)$_n$—, and —$NR_DS$(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, $C_1$-$C_4$alkyl, —O($C_1$-$C_4$alkyl), —NH($C_1$-$C_4$alkyl), —N($C_1$-$C_4$alkyl)($C_1$-$C_4$alkyl), and —S(O)$_n$(alkyl), wherein said 3- to 7-membered heterocyclic groups contain one or more heteroatom(s) independently selected from N, O, and S, with the point of attachment being either carbon or nitrogen;

p is independently selected at each occurrence from 0, 1, 2, and 3; and n is independently selected at each occurrence from 0, 1, and 2.

12. The compound or salt of claim 11, wherein $Z_1$=$NR_1''$, $Z_3$=$CR_3$, $Z_4$=$CR_4$, and R is absent at each occurrence.

13. The compound or salt of claim 11, wherein $Z_1$=$CR_1$, $Z_3$=$CR_3''$, $Z_4$=$CR_4$, and R is absent.

14. The compound or salt of claim 11, wherein $R_1$ and $R_1''$ are selected from phenyl, 1-naphthyl, 2-naphthyl, pyridinyl, pyrazinyl, pyrimidinyl, benzyl, pyridinyl-methyl, pyrazinyl-methyl, and pyrimidinyl-methyl, each of which is substituted with between 0 and 2 substituents independently selected from halogen, hydroxy, amino, oxo, cyano, $C_1$-$C_3$alkyl, $C_1$-$C_3$alkoxy, $C_1$-$C_3$hydroxyalkyl, $C_2$-$C_4$alkoxyalkyl, $C_1$-$C_2$haloalkoxy, $C_5$-$C_6$heteroaryl, mono- and di-($C_1$-$C_2$) alkylamino, COOH, COO($C_1$-$C_4$alkyl), CONH($C_1$-$C_4$alkyl), and CON($C_1$-$C_4$alkyl)$_2$.

15. The compound or salt of claim 11, wherein Ar is selected from the group consisting of phenyl, pyridyl and pyrimidinyl each of which is mono- di- or trisubstituted with substituents independently chosen from halogen, cyano, nitro, halo($C_1$-$C_6$)alkyl, halo($C_1$-$C_6$)alkoxy, hydroxy, amino, $C_1$-$C_6$alkyl, $C_2$-$C_6$alkenyl, $C_2$-$C_6$alkynyl, $C_3$-$C_7$cycloalkyl, ($C_3$-$C_7$cycloalkyl)$C_1$-$C_4$alkyl, $C_1$-$C_6$alkoxy, mono- and di($C_1$-$C_6$alkyl)amino, amino($C_1$-$C_6$)alkyl, and mono- and di($C_1$-$C_6$alkyl)amino, wherein, in Ar, at least one of the positions ortho to the point of attachment is substituted.

16. The compound or salt of claim 11, wherein $R_2$ is hydrogen, methyl, or ethyl.

17. The compound or salt of claim 11, wherein $R_4$ and $R_5$ are independently selected from hydrogen, halogen, hydroxy, amino, cyano, $C_1$-$C_6$alkyl, halo($C_1$-$C_4$)alkyl, $C_1$-$C_6$alkoxy, ($C_2$-$C_6$)alkoxyalkyl mono and di($C_1$-$C_6$)alkylamino, phenyl, 5 to 6 membered heterocycloalkyl and 5 to 6 member heteroaryl, each of which is substituted with 0 or more substituents independently chosen from halogen, hydroxy, amino, oxo, cyano, $C_1$-$C_6$alkyl, $C_1$-$C_6$alkoxy, $C_1$-$C_6$hydroxyalkyl, $C_1$-$C_6$alkoxy$C_1$-$C_6$alkyl, $C_1$-$C_6$haloalkoxy, $C_5$-$C_7$heteroaryl, mono- and di-($C_1$-$C_6$)alkylamino, —$XR_C$, and Y.

18. The compound or salt of claim 11, wherein $R_4$ and $R_5$ are independently selected from hydrogen, halogen, hydroxy, amino, cyano, $C_1$-$C_6$alkyl, $C_1$-$C_6$alkoxy, mono- and di-($C_1$-$C_6$alkyl)amino.

19. A compound or salt according to claim 11, wherein:
$R_1$ or $R_1''$ is phenyl, 1-naphthyl, 2-naphthyl, pyridyl, pyrimidinyl, pyrazinyl, pyridazinyl, each of which is optionally substituted; or
$R_1$ or $R_1''$ is a group of the formula:

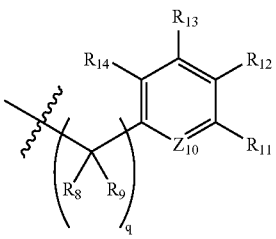

wherein
q is 1, 2, or 3;
$R_8$ and $R_9$ are independently chosen at each occurrence from hydrogen or $C_1$-$C_4$alkyl, or $CR_8R_9$ taken in combination form a keto group;
$Z_{10}$ is nitrogen or $CR_{10}$;
$R_{10}$, $R_{11}$, $R_{12}$, $R_{13}$, and $R_{14}$ are independently selected from the group consisting of hydrogen, halogen, hydroxy, amino, cyano, —COOH, —C(O)NH$_2$, $C_1$-$C_6$alkyl, $C_1$-$C_6$alkoxy, halo$C_1$-$C_6$alkyl, halo$C_1$-$C_6$alkoxy, $C_3$-$C_7$cycloalkyl, hydroxy$C_1$-$C_6$alkyl, amino$C_1$-$C_6$alkyl.

20. The compound of claim 19, wherein
$R_2$ is selected from hydrogen, $C_1$-$C_6$alkyl;
$R_3$ is hydrogen, halogen, hydroxy, amino, $C_1$-$C_6$alkyl, $C_1$-$C_6$alkoxy, halo$C_1$-$C_6$alkyl, halo$C_1$-$C_6$alkoxy, $C_3$-$C_7$cycloalkyl, phenyl substituted with 0-2 independently selected $R_B$ groups; five to seven membered heterocycloalkyl substituted with 0-2 independently selected $R_A$; —(CH$_2$)$_p$(CH(OH))R$_D$, —(CH$_2$)$_p$C(O)R$_A$, and —(CH$_2$)$_p$S(O)$_2$R$_C$;
$R_5$ is selected from hydrogen, halogen, cyano, amino, $C_1$-$C_6$alkyl, $C_1$-$C_6$alkoxy, $C_3$-$C_7$cycloalkyl, ($C_3$-$C_7$cycloalkyl)$C_1$-$C_4$alkyl, ($C_3$-$C_7$cycloalkyl)$C_1$-$C_4$alkoxy, mono and di($C_1$-$C_6$alkyl)amino, amino($C_1$-$C_6$)alkyl, mono and di($C_1$-$C_6$alkyl)amino($C_1$-$C_6$)alkyl, halo($C_1$-$C_6$)alkyl, and halo($C_1$-$C_6$)alkoxy; and
Ar is selected from the group consisting of phenyl, pyridyl and pyrimidinyl each of which is mono- di- or trisubstituted with substituents independently chosen from halogen, cyano, nitro, halo($C_1$-$C_6$)alkyl, halo($C_1$-$C_6$)alkoxy, hydroxy, amino, $C_1$-$C_6$alkyl, $C_2$-$C_6$alkenyl, $C_2$-$C_6$alkynyl, $C_3$-$C_7$cycloalkyl, ($C_3$-$C_7$cycloalkyl)$C_1$-$C_4$alkyl, $C_1$-$C_6$alkoxy, mono- and di($C_1$-$C_6$alkyl)amino, amino($C_1$-$C_6$)alkyl, and mono- and di($C_1$-$C_6$alkyl) amino, wherein, in Ar, at least one of the positions ortho to the point of attachment is substituted.

21. A compound or salt according to claim 11, wherein:
$R_1''$ is selected from mono-, di-, or tri-substituted phenyl, or 1-naphthyl, 2-naphthyl, pyridyl, pyrimidinyl, pyrazinyl, and pyridazinyl, each of which is optionally mono-, di-, or tri-substituted, or $R_1''$ is a group selected from:

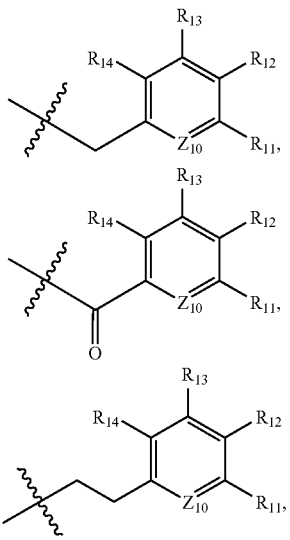

wherein $Z_{10}$ is N or $CR_{10}$;
$R_8$ and $R_9$ are independently chosen at each occurrence from hydrogen or $C_1$-$C_4$alkyl, or $CR_8R_9$ taken in combination form a keto group;
$R_{10}$, $R_{11}$, $R_{12}$, $R_{13}$, and $R_{14}$ are independently selected from the group consisting of hydrogen, halogen, hydroxy, amino, cyano, —COOH, —C(O)NH$_2$, $C_1$-$C_6$alkyl, $C_1$-$C_6$alkoxy, $C_2$-$C_6$alkenyl, $C_2$-$C_6$alkynyl, hydroxy$C_1$-$C_6$alkyl, amino$C_1$-$C_6$alkyl.

22. The compound or salt according to claim 11, wherein
$R_3$ is hydrogen, halogen, hydroxy, amino, $C_1$-$C_6$alkyl, $C_1$-$C_6$alkoxy, halo$C_1$-$C_6$alkyl, halo$C_1$-$C_6$alkoxy, $C_3$-$C_7$cycloalkyl, phenyl substituted with 0-2 independently selected $R_B$ groups; five to seven membered heterocycloalkyl substituted with 0-2 independently selected $R_A$; —(CH$_2$)$_p$(CH(OH))R$_D$, —(CH$_2$)$_p$C(O)R$_A$, and —(CH$_2$)$_p$S(O)$_2$R$_C$; or
$R_3''$ is hydrogen, $C_1$-$C_6$alkyl, halo$C_1$-$C_6$alkyl, $C_3$-$C_7$cycloalkyl, phenyl substituted with 0-2 independently selected $R_B$ groups; five to seven membered heterocycloalkyl substituted with 0-2 independently selected $R_A$; —(CH$_2$)$_p$(CH(OH))R$_D$, —(CH$_2$)$_p$C(O)R$_A$, and —(CH$_2$)$_p$S(O)$_2$R$_C$; and
p is 0, 1, 2, or 3.

23. The compound or salt according to claim 22, wherein
$R_3$ or $R_3''$ is hydrogen, $C_1$-$C_6$alkyl, $C_1$-$C_6$alkoxy, $C_3$-$C_7$cycloalkyl, —(CH$_2$)$_p$(CH(OH))R$_D$, —(CH$_2$)$_p$C(O)R$_A$, and —(CH$_2$)$_p$S(O)$_2$R$_C$; and
p is 0, 1, or 2.

24. A pharmaceutical composition comprising at least one compound or salt thereof according to claim 1 or claim 11, in combination with a physiologically acceptable carrier or excipient.

25. A pharmaceutical composition according to claim 24, wherein the pharmaceutical composition is formulated as an injectable fluid, an aerosol, a cream, a gel, a pill, a capsule, a syrup, or a transdermal patch.

* * * * *